US008815868B2

(12) United States Patent  (10) Patent No.: US 8,815,868 B2
Netz et al.  (45) Date of Patent: *Aug. 26, 2014

(54) SUBSTITUTED OXINDOLE DERIVATIVES AND THEIR USE AS VASOPRESSIN RECEPTOR LIGANDS

(75) Inventors: Astrid Netz, Ludwigshafen (DE); Thorsten Oost, Biberach an der Riss (DE); Herve Geneste, Ludwigshafen (DE); Wilfried Braje, Ludwigshafen (DE); Wolfgang Wernet, Ludwigshafen (DE); Andrea Hager-Wernet, legal representative, Neustadt (DE); Liliane Unger, Ludwigshafen (DE); Wilfried Hornberger, Ludwigshafen (DE); Wilfried Lubisch, Heldelberg (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 308 days.

This patent is subject to a terminal disclaimer.

(21) Appl. No.: 12/521,713

(22) PCT Filed: Dec. 28, 2007

(86) PCT No.: PCT/EP2007/064622

§ 371 (c)(1),
(2), (4) Date: Sep. 7, 2010

(87) PCT Pub. No.: WO2008/080973

PCT Pub. Date: Jul. 10, 2008

(65) Prior Publication Data

US 2011/0124658 A1 May 26, 2011

(30) Foreign Application Priority Data

Dec. 30, 2006 (DE) .......................... 10 2006 062 505
Dec. 30, 2006 (DE) .......................... 10 2006 062 506
Dec. 30, 2006 (DE) .......................... 10 2006 062 507
Dec. 30, 2006 (DE) .......................... 10 2006 062 508

(51) Int. Cl.
*A61K 31/496* (2006.01)
*A61K 31/4545* (2006.01)
*C07D 401/04* (2006.01)
*C07D 401/14* (2006.01)

(52) U.S. Cl.
CPC ................................. *C07D 401/14* (2013.01)
USPC ........ 514/253.09; 514/318; 544/364; 546/187

(58) Field of Classification Search
None
See application file for complete search history.

(56) References Cited

U.S. PATENT DOCUMENTS 3,964,896 A 6/1976 Brouwer et al.
4,022,901 A 5/1977 Narayanan et al.
4,122,257 A 10/1978 Prossel et al.
5,594,023 A 1/1997 Wagnon et al.
5,914,328 A 6/1999 Lin et al.
5,948,793 A 9/1999 Abreo et al.
5,977,144 A 11/1999 Meyer et al.
6,090,818 A 7/2000 Foulon et al.
6,130,217 A 10/2000 Arnold et al.
6,207,863 B1 3/2001 Berrier et al.
6,538,003 B1 3/2003 Galli et al.
6,579,880 B2 6/2003 Weidner-Wells et al.
6,596,732 B2 7/2003 Serradeil-Le Gal et al.
6,605,610 B1 8/2003 Coe et al.
6,624,164 B2 9/2003 Schoentjes et al.
6,809,105 B2 10/2004 Schrimpf et al.
6,833,370 B1 12/2004 Schrimpf et al.
6,864,277 B2 3/2005 Roux et al.
6,919,359 B2 7/2005 Piotrowski et al.
7,041,685 B2 5/2006 Cai et al.
7,119,086 B2 10/2006 Di Malta et al.

(Continued)

FOREIGN PATENT DOCUMENTS

CA 2107348 1/1992
CA 2593044 A1 7/2006

(Continued)

OTHER PUBLICATIONS

Banker et al. "Modern Pharmaceutics", 3rd Ed. p. 596 (1996).*

(Continued)

*Primary Examiner* — Emily Bernhardt
(74) *Attorney, Agent, or Firm* — Lisa V. Mueller; Michael Best & Friedrich LLP

(57) ABSTRACT

The present invention relates to novel oxindole derivatives of the general formula (I)

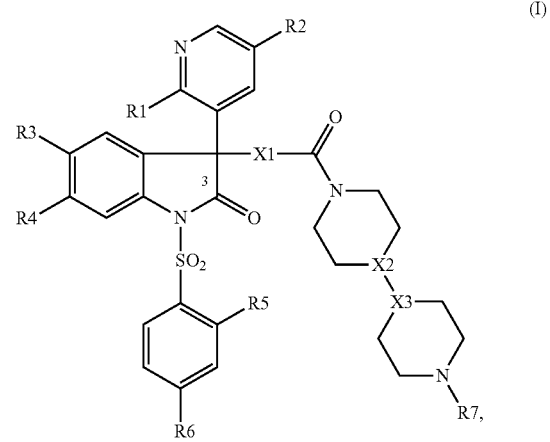

to medicaments comprising them and to their use for the prophylaxis and/or treatment of diseases.

55 Claims, No Drawings

(56) References Cited

U.S. PATENT DOCUMENTS

| | | |
|---|---|---|
| 7,902,379 B2 | 3/2011 | Lubisch et al. |
| 8,017,631 B2 | 9/2011 | Dahl et al. |
| 8,129,389 B2 | 3/2012 | Lubisch et al. |
| 8,350,055 B2 | 1/2013 | Oost et al. |
| 2003/0109545 A1 | 6/2003 | Serradeil-Le-Gal et al. |
| 2003/0114683 A1 | 6/2003 | Roux et al. |
| 2003/0139413 A1 | 7/2003 | Schoentjes et al. |
| 2003/0162767 A1 | 8/2003 | Roux et al. |
| 2004/0063601 A1 | 4/2004 | Denome et al. |
| 2004/0152724 A1 | 8/2004 | Dart et al. |
| 2004/0180878 A1* | 9/2004 | Di Malta et al. ............. 514/218 |
| 2004/0186107 A1 | 9/2004 | Schrimpf et al. |
| 2004/0204461 A1 | 10/2004 | Karp et al. |
| 2005/0070718 A1 | 3/2005 | Lubisch et al. |
| 2006/0019976 A1 | 1/2006 | Karp et al. |
| 2007/0021465 A1 | 1/2007 | Al-Abed et al. |
| 2007/0021607 A1 | 1/2007 | Lubisch et al. |
| 2007/0185126 A1 | 8/2007 | Lubisch et al. |
| 2008/0167286 A1 | 7/2008 | Gopalakrishnan et al. |
| 2008/0255203 A1 | 10/2008 | Lee et al. |
| 2008/0269236 A1 | 10/2008 | Ji et al. |
| 2008/0318923 A1 | 12/2008 | Sekiguchi et al. |
| 2009/0005397 A1 | 1/2009 | Lubisch |
| 2009/0163492 A1 | 6/2009 | Thorsten |
| 2009/0215790 A1 | 8/2009 | Lubisch |
| 2010/0305086 A1 | 12/2010 | Gopalakrishnan et al. |
| 2011/0077241 A1 | 3/2011 | Lubisch et al. |
| 2011/0124658 A1 | 5/2011 | Netz et al. |
| 2011/0190314 A1 | 8/2011 | Gopalakrishnan et al. |

FOREIGN PATENT DOCUMENTS

| | | |
|---|---|---|
| DE | 10148598 A1 | 10/2002 |
| EP | 0979814 B1 | 10/2003 |
| EP | 2226074 A2 | 9/2010 |
| EP | 2101763 B1 | 7/2012 |
| EP | 2114921 B1 | 12/2012 |
| EP | 2546250 A1 | 1/2013 |
| EP | 2546251 A1 | 1/2013 |
| EP | 2546252 A1 | 1/2013 |
| WO | 93/13083 A1 | 7/1993 |
| WO | 93/15051 A1 | 8/1993 |
| WO | 95/18105 A1 | 7/1995 |
| WO | WO 96/40682 | 12/1996 |
| WO | 98/25901 A1 | 6/1998 |
| WO | 99/10338 A2 | 3/1999 |
| WO | WO 99/32480 | 7/1999 |
| WO | WO 99/65876 | 12/1999 |
| WO | 0007600 A1 | 2/2000 |
| WO | 0045799 A2 | 8/2000 |
| WO | WO 00/71534 | 11/2000 |
| WO | WO 00/75110 | 12/2000 |
| WO | 01/55130 A2 | 8/2001 |
| WO | 01/55134 A2 | 8/2001 |
| WO | 0162736 A1 | 8/2001 |
| WO | 01/64668 A2 | 9/2001 |
| WO | 01/81347 A2 | 11/2001 |
| WO | 0181334 A2 | 11/2001 |
| WO | 0187295 A1 | 11/2001 |
| WO | 0198295 A1 | 12/2001 |
| WO | 02/068417 A2 | 9/2002 |
| WO | WO 02/100826 | 12/2002 |
| WO | 03/008407 A2 | 1/2003 |
| WO | 2004/018607 A2 | 3/2004 |
| WO | 2005/030755 A1 | 4/2005 |
| WO | 2006/005609 A2 | 1/2006 |
| WO | 2006/047392 A2 | 5/2006 |
| WO | 2006/071184 A1 | 7/2006 |
| WO | 2006072458 A2 | 7/2006 |
| WO | 2006/080574 A1 | 8/2006 |
| WO | 2006/086068 A1 | 8/2006 |
| WO | 2006/096358 A1 | 9/2006 |
| WO | 2006/100081 A2 | 9/2006 |
| WO | 2006/100082 A2 | 9/2006 |
| WO | 2006100080 A1 | 9/2006 |
| WO | 2006/114400 A1 | 11/2006 |
| WO | 2007/149395 A2 | 12/2007 |
| WO | 2008/028903 A2 | 3/2008 |
| WO | 2008/073942 A2 | 6/2008 |
| WO | 2008/080970 A1 | 7/2008 |
| WO | 2008/080971 A1 | 7/2008 |
| WO | 2008/080973 A1 | 7/2008 |
| WO | 2008080972 A1 | 7/2008 |
| WO | 2009/148452 A1 | 12/2009 |
| WO | 2010/138600 A2 | 12/2010 |
| WO | 2010148598 A1 | 12/2010 |

OTHER PUBLICATIONS

Wolff, Manfred E. Burger's Medicinal Chemistry, 5th Ed. Part 1, pp. 975-977 (1995).*

Hays, New England Journal of Medicine, vol. 355(20), p. 2146-2148 (2006).*

Barberis et al., "Structural bases of vasopressin/osytocin receptor function," J. Endocrinology, 1998, 223-229, vol. 156, France.

Hulme et al., "Quasternary Substituted PDE4 Inhibitors 1: The Synthesis and in Bitro Evaluation of a Novel Series of Oxindoles," Bioorg. & Med. Chem Lett, 1998, 175-178, vol. 8, United Kingdom.

Wersinger et al., "Vasopressin V 1b Receptor Knockout Reduces Aggressive Behavior in male mice," Molecular Psychiatry, 2002, 975-984, vol. 7, United Kingdom.

Griebel et al., "Anxiolytic-and Antidepressant-like Effects of the Non-peptide Vassopressin V 1b Receptor Antagonist, SSR 149415, Suggest as Innovative Approach for the Treatment of Stress-related Disorders," PNAS, 2002, 6370-6375, vol. 99, France.

Serradeil-Le Gal et al., J. Pharm. Exp. Ther., 2002, 1122-1130, vol. 300, France.

Office Action filed for U.S. Appl. No. 10/574,211 and mailed Jun. 5, 2009.

Office Action filed for U.S. Appl. No. 10/574,211 and mailed Sep. 11, 2008.

Office Action filed for U.S. Appl. No. 10/574,211 and mailed Jan. 22, 2009.

Office Action filed for U.S. Appl. No. 11/440,569 and mailed Aug. 4, 2009.

Office Action filed for U.S. Appl. No. 11/440,569 and mailed Dec. 9, 2008.

Thibonnier, M., Exp. Opin. Invest. Drugs, 1998, vol. 7, No. 5, pp. 729-740.

U.S. Appl. No. 61/058,735, dated Jun. 4, 2008, Ji et al.

Bitner R.S., et al., "Reduced Nicotinic Receptor-Mediated Antinociception Following in Vivo Antisense Knock-Down in Rat ," Brain Research , 2000, vol. 871, pp. 66-74.

Brain C.T., et al., "Novel Procedure for the Synthesis of 1,3,4-oxadiazoles from 1,2-diacylhydrazines Using Polymer-Supported Burgess Reagent Under Microwave Conditions," Tetrahedron Letters, 1999, vol. 40, pp. 3275-3278.

Bundgaard, E. et al., "Design of Prodrugs, Elsevier Science Publishers, Amsterdam, Table of Contents," 1986.

Bundgaard H., ed., in: Design of Prodrugs, Elsevier Science, 1985, Table of Contents.

Chaplan S.R., et al., "Quantitative Assessment of Tactile Allodynia in the Rat Paw," Journal of Neuroscience Methods, 1994, vol. 53 (1), pp. 55-63.

Cheung B.S., et al., "Etiologic Significance of Arginine Vasopressin in Motion Sickness," Journal of Clinical Pharmacology, 1994, vol. 34 (6), pp. 664-670.

Co-pending U.S. Appl. No. 11/953590, filed on Dec. 10, 2007.

Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.

Cucchiaro G., et al., "The Dorsal Raphe Nucleus as a Site of Action of the Antinociceptive and Behavioral Effects of the Alpha4 Nicotinic Receptor Agonist Epibatidine," Journal of Pharmacology and Experimental Therapeutics, 2005, vol. 313 (1), pp. 389-394.

(56) References Cited

OTHER PUBLICATIONS

Curtis L., et al., "Potentiation of Human Alpha4beta2 Neuronal Nicotinic Acetylcholine Receptor by Estradiol," Molecular Pharmacology, 2002, vol. 61 (1), pp. 127-135.
De Francesco R., et al., "Approaching a new era for Hepatitis C virus Therapy: Inhibitors of the NS3-4A Serine Protease and the NS5B RNA-Dependent RNA Polymerase," Antiviral Research, 2003, vol. 58 (1), pp. 1-16.
De Francesco R., et al., "Challenges and Successes in Developing New Therapies for Hepatitis C," Nature, 2005, vol. 436 (7053), pp. 953-960.
Decker M.W., et al., "Nicotinic Acetylcholine Receptor Agonists: a Potential New Class of Analgesics," Current Topics in Medicinal Chemistry, 2004, vol. 4 (3), pp. 369-384.
Decker M.W., et al., "The Therapeutic Potential of Nicotinic Acetylcholine Receptor Agonists for Pain Control," Expert Opinion on Investigational Drugs, 2001, vol. 10 (10), pp. 1819-1830.
Dunbar G.C., et al., "Effect of Ispronicline, a Neuronal Nicotinic Acetylcholine Receptor Partial Agonist, in Subjects with Age Associated Memory Impairment (AAMI).," Journal of Psychopharmacology, 2007, vol. 21 (2), pp. 171-178.
Emsley R.A., et al., "Vasopressin Secretion and Memory Impairment in Alcoholic Korsakoffs Syndrome," Alcohol and Alcoholism, 1995, vol. 30 (2), pp. 223-229.
Ersek K., et al., "The Cognitive Effects of Opioids," Pain Management Nursing, 2004, vol. 5 (2), pp. 75-93.
Ettmayer P., et al., "Lessons Learned from Marketed and Investigational Prodrugs," Journal Medicinal Chemistry, 2004, vol. 47 (10), pp. 2393-2404.
European Search Report for Application No. EP10163998, mailed on Jan. 28, 2011, 5 pages.
European Search Report for Application No. EP12177640, mailed on Dec. 12, 2012, 2 pages.
European Search Report for Application No. EP12177642, mailed on Dec. 12, 2012, 2 pages.
European Search Report for Application No. EP12177644, mailed on Dec. 12, 2012, 1 page.
Everts H.G., et al., "Differential Modulation of Lateral Septal Vasopressin Receptor Blockade in Spatial Learning, Social Recognition, and Anxiety-Related Behaviors in Rats," Behavioural Brain Research, 1999, vol. 99 (1), pp. 7-16.
Ex Parte Quayle Action mailed Sep. 11, 2008 for U.S. Appl. No. 10/574211 filed Jan. 22, 2007.
Ex Parte Quayle Action mailed Aug. 21, 2012 for U.S. Appl. No. 12/839612 filed Jul. 20, 2010.
Ex Parte Quayle Action mailed Aug. 22, 2012 for U.S. Appl. No. 12/134678 filed Jun. 6, 2008.
Ferreira M., et al., "Brainstem Nicotinic Receptor Subtypes That Influence Intragastric and Arterial Blood Pressures," Journal of Pharmacology and Experimental Therapeutics, 2000, vol. 294 (1), pp. 230-238.
Final Office Action mailed Sep. 27, 2012 for U.S. Appl. No. 13/080,071 filed Apr. 5, 2011.
Final Office Action mailed Sep. 29, 2011 for U.S. Appl. No. 12/787,937 filed May 26, 2010.
Franklin S. R., et al., "Positive Allosteric Modulation of Alpha $ Beta 2 Nicotinic Receptors Potrntiates Some CNS Effects of the Alpha 4 Beta 2 Agonist, ABT-594," Biochemical Pharmacology, 2009, vol. 78 (7), pp. 921.
Furniss B.S., et al., Vogel's Textbook of Practical Organic Chemistry, 5th Edition, Longman Scientific & Technical, 1989, Table of Contents.
Gopalakrishnan, M. et al., "Ion channels—Ligand gated. Comprehensive Medicinal Chemistry II, Edited by Triggle D.J. et al." Major Reference Works, 2006, Unit 2.22, pp. 877-918, Elsevier.
Grant P.J., et al., "Effects of Physiological Concentrations of Vasopressin on Haemostatic Function in Man," Clinical Science, 1985, vol. 69 (4), pp. 471-476.

Greene T.W., et al., in: Protective Groups in Organic Synthesis, 3rd Edition, John Wiley and Sons, Inc., 1999, Preface, Table of Contents, Abbreviations.
Greene T.W., et al., "Protection for the Amino group," Protective Groups in Organic Synthesis, 1999, Third Edition, pp. 494-653.
Higuchi T., et al., eds., Pro-drugs as Novels Delivery Systems, vol. 14, ACS Symposium Series, 1975, Table of Contents.
Humphrey G.R., et al., "A Novel Synthesis of 3-Bromo-1,2,4-oxadiazoles," Journal of Heterocyclic Chemistry, 1989, vol. 26 (1), pp. 23-24.
International Preliminary Report on Patentability and Written Opinion for Application No. PCT/US08/066002, mailed on Dec. 6, 2010, 8 pages.
International Preliminary Report on Patentability and Written Opinion for Application No. PCT/US2007/087090, mailed on Jun. 16, 2009, 11 pages.
International Preliminary Report on Patentability and Written Opinion for Application No. PCT/US2010/036213, mailed on Nov. 29, 2011, 14 pages.
International Search Report for Application No. PCT/US08/066002, mailed on Jan. 20, 2009, 3 pages.
International Search Report for Application No. PCT/US2007/087090, mailed on Oct. 20, 2008, 5 pages.
International Search Report for Application No. PCT/US2007/087091, mailed on May 8, 2008, 3 pages.
International Search Report for Application No. PCT/US2010/036213, mailed on Nov. 24, 2010, 8 pages.
Isobe T., et al., "2-Chloro-1,3-dimethylimidazolinium Chloride. 1. A Powerful Dehydrating Equivalent to DCC," The Journal of Organic Chemistry, 1999, vol. 64, pp. 6984-6988.
Itoh S., et al., "Attenuated Stress-induced Catecholamine Release in Mice Lacking the Vasopressin V1b Receptor," American Journal of Physiology. Endocrinology and Metabolism, 2006, vol. 291 (1), pp. E147-E151.
Japundzic-Zigon N., et al., "Effects of Nonpeptide and Selective V1 and V2 Antagonists on Blood Pressure Short-Term Variability in Spontaneously Hypertensive Rats," Journal of Pharmacological Sciences, 2004, vol. 95 (1), pp. 47-55.
Jonat S., et al., "Effect of DDAVP on Nocturnal Enuresis in a Patient with Nephrogenic Diabetes Insipidus," Archives of Disease in Childhood, 1999, vol. 81 (1), pp. 57-59.
Khan I.M., et al., "Ablation of Primary Afferent Terminals Reduces Nicotinic Receptor Expression and the Nociceptive Responses to Nicotinic Agonists in the Spinal Cord," Journal of Neurocytology, 2004, vol. 33 (5), pp. 543-556.
Khan M.T., et al., "Structure-Activity Relationships of Tyrosinase Inhibitory Combinatorial Library of 2,5-Disubstituted-1,3,4-Oxadiazole Analogues," Bioorganic & Medicinal Chemistry, 2005, vol. 13 (10), pp. 3385-3395.
Kim S.H., et al., "An Experimental Model for Peripheral Neuropathy Produced by Segmental Spinal Nerve Ligation in the Rat," Pain, 1992, vol. 50 (3), pp. 355-363.
Kirrane T., et al., "Effects of Amphetamine on Cognitive Impairment in Schizotypal Personality Disorder," Biological Psychiatry, 1996, vol. 39 (7), pp. 581.
Kocevar M., et al., "Ring Transformations of Some 4-Aminopteridine 3-Oxides and Derivatives," Tetrahedron, 1982, vol. 39 (5), pp. 823-829.
Koch Uwe et al., "2-(2-thienyl)-5,6-dihydroxy-4-carboxypyrimidines as inhibitors of the hepatitis C virus NS5B polymerase: Discovery, SAR, modeling, and mutagenesis," Journal of Medicinal Chemistry, vol. 49(5), pp. 1693-1705, 2006.
Kocsis J., et al., "Histochemical and Ultrastructural Study of Renal Cortical Necrosis in Rats Treated with Oestrone + Vasopressin, and its Prevention with a Vasopressin Antagonist," British Journal of Experimental Pathology, 1987, vol. 68 (1), pp. 35-43.
Lauretti G.R., "Highlights in Opioid Agonists and Antagonists," Neurotherapeutics, 2006, vol. 6 (4), pp. 613-622.
Lee C.R., et al., "Vasopressin: a New Target for the Treatment of Heart Failure," American Heart Journal, 2003, vol. 146 (1), pp. 9-18.
Lin Y., et al., "New Synthesis of 1,2,4-Triazoles and 1,2,4-Oxadiazoles," the Journal of Organic Chemistry, 1979, vol. 44 (23), pp. 4160-4164.

(56) References Cited

OTHER PUBLICATIONS

March J., "Advanced Organic Chemistry: Reactions, Mechanisms, and Structure" 3rd Edition, John Wilsey & Sons, 1985, Table of Contents.
Mark N. F., et al., "Kirk-Othmer Encyclopedia of Chemical Technology" Second Completely Revised Edition, John Wiley & Sons Inc., 1972, Table of Contents.
Marubio L.M., et al., "Reduced Antinociception in Mice Lacking Neuronal Nicotinic Receptor Subunits," Nature, 1999, vol. 398 (6730), pp. 805-810.
Maturi M.F., et al., "Coronary Vasoconstriction Induced by Vasopressin. Production of Myocardial Ischemia in Dogs by Constriction of Nondiseased Small Vessels," Circulation, 1991, vol. 83 (6), pp. 2111-2121.
McClelland R.A., "Kinetics and Mechanism of Amide Acetal Hydrolysis," Journal of the American Chemical Society, 1978, vol. 100 (6), pp. 1844-1849.
Narahashi T., et al., "Mechanisms of Action of Cognitive Enhancers on Neuroreceptors," Biological & Pharmaceutical Bulletin, 2004, vol. 27 (11), pp. 1701-1706.
Non-Final Office Action mailed Mar. 2, 2012 for U.S. Appl. No. 12/134678 filed Jun. 6, 2008.
Non-Final Office Action mailed Dec. 9, 2010 for U.S. Appl. No. 11/953,625 filed Dec. 10, 2007.
Non-Final Office Action mailed Jan. 10, 2012 for U.S. Appl. No. 12/839,612 filed Jul. 20, 2010.
Non-Final Office Action mailed Feb. 11, 2013 for U.S. Appl. No. 13/590,261 filed Aug. 21, 2012.
Non-Final Office Action mailed Apr. 15, 2011 for U.S. Appl. No. 12/134,678 filed Jun. 6, 2008.
Non-Final Office Action mailed Apr. 18, 2011 for U.S. Appl. No. 12/787,937 filed May 26, 2010.
Non-Final Office Action mailed Mar. 19, 2012 for U.S. Appl. No. 13/080,071 filed Apr. 5, 2011.
Non-Final Office Action mailed Feb. 24, 2012 for U.S. Appl. No. 12/839,595 filed Jul. 20, 2010.
Non-Final Office Action mailed Nov. 30, 2010 for U.S. Appl. No. 10/574,211 filed Jan. 22, 2007.
Non-Final Office Action mailed Sep. 30, 2011 for U.S. Appl. No. 12/134,678 filed Jun. 6, 2008.
Notice of Allowance mailed Oct. 1, 2010 for U.S. Appl. No. 11/440,569 filed May 25, 2006.
Notice of Allowance mailed Dec. 2, 2009 for U.S. Appl. No. 10/574,211 filed Jan. 22, 2007.
Notice of Allowance mailed Sep. 4, 2012 for U.S. Appl. No. 12/839,612 filed Jul. 20, 2010.
Notice of Allowance mailed May 5, 2010 for U.S. Appl. No. 10/574,211 filed Jan. 22, 2007.
Notice of Allowance mailed Dec. 10, 2012 for U.S. Appl. No. 12/134,678 filed Jun. 6, 2008.
Notice of Allowance mailed Jan. 10, 2011 for U.S. Appl. No. 10/574,211 filed Jan. 22, 2007.
Notice of Allowance mailed Mar. 12, 2010 for U.S. Appl. No. 11/440,569 filed May 25, 2006.
Notice of Allowance mailed Jun. 24, 2010 for U.S. Appl. No. 11/440,569 filed May 25, 2006.
Notice of Allowance mailed Jun. 26, 2012 for U.S. Appl. No. 12/839,595 filed Jul. 20, 2010.
Office action mailed Dec. 1, 2011 for European Application No. 08770247.8 filed Jun. 6, 2008.
Office action mailed Sep. 10, 2012 for European Application No. 10720520.5 filed May 26, 2010.
Office action mailed Nov. 17, 2011 for European Application No. 10163998.7 filed Dec. 12, 2007.
Office action mailed Jun. 18, 2012 for European Application No. 10163998.7 filed Dec. 12, 2007.
Office action mailed Mar. 29, 2012 for European Application No. 08770247.8 filed Jun. 6, 2008.
Oshikawa S., et al., "Vasopressin Stimulates Insulin Release from Islet Cells through V1b Receptors: a Combined Pharmacological/knockout Approach," Molecular Pharmacology, 2004, vol. 65 (3), pp. 623-629.
Pasternak G.W., "Pharmacological Mechanisms of Opioid Analgesics," Clinical Neuropharmacology, 1993, vol. 16 (1), pp. 1-18.
Pavo I., et al., "Vasopressin Deficiency Decreases the Frequency of Gastroduodenal Ulceration in Humans," Journal of Physiology, 2000, vol. 94 (1), pp. 63-66.
Poulain R.F., et al., "Parallel Synthesis of 1,2,4-oxadiazoles from carboxylic Acids Using an Improved, Uronium-based Activation," Tetrahedron Letters, 2001, vol. 42 (8), pp. 1495-1498.
Prescott D.M., "Methods in Cell Biology", Academic Press, 1976, Table of Contents.
Qian X., et al., "Syntheses and Insecticidal Activities of Novel 2,5-Disubstituted-1,3,4-Oxadiazoles," Journal of Chemical Technology and Biotechnology, 1996, vol. 67 (2), pp. 124-130.
Rashid M.H., et al., "Tonic Inhibitory Role of Alpha4beta2 Subtype of Nicotinic Acetylcholine Receptors on Nociceptive Transmission in the Spinal Cord in Mice," Pain, 2006, vol. 125 (1-2), pp. 125-135.
Reynaud P. et al., "A New Synthetic Route to 1,3,4-oxadiazoles. Pharmacological Study of Some New Derivatives", Journal of Heterocyclic Chemistry, 1992, vol. 29 (4), pp. 991-993.
Ring R.H., et al., "The Central Vasopressinergic System: Examining the Opportunities for Psychiatric Drug Development," Current Pharmaceutical Design, 2005, vol. 11 (2), pp. 205-225.
Roche E.B., ed., Bioreversible Carries in Drug Design Theory and Application, Pergamon Press, 1987, Table of Contents.
Rueter L.E., et al., "Abt-089: Pharmacological Properties of a Neuronal Nicotinic Acetylcholine Receptor Agonist for the Potential Treatment of Cognitive Disorders," CNS Drug Review, 2004, vol. 10 (2), pp. 167-182.
Ryckmans T., et al., "Modulation of the Vasopressin System for the Treatment of CNS Diseases," Current opinion in drug discovery & development, 2010, vol. 13 (5), pp. 538-547.
Scheurer M.A., et al., "Vasopressin to Attenuate Pulmonary Hypertension and Improve Systemic Blood Pressure after Correction of Obstructed Total Anomalous Pulmonary Venous Return," the Journal of Thoracic and Cardiovascular Surgery, 2005, vol. 129 (2), pp. 464-466.
Skoubis P.D., et al., "Mapping Brain Activity Following Administration of a Nicotinic Acetylcholine Receptor Agonist, ABT-594, Using Functional Magnetic Resonance Imaging in Awake Rats," Neuroscience, 2006, vol. 137 (2), pp. 583-591.
Sobol E., et al., "Tetramethylcyclopropyl Analogue of a Leading Antiepileptic Drug, Valproic Acid. Synthesis and Evaluation of Anticonvulsant Activity of Its Amide Derivatives," Journal of Medicinal Chemistry, 2004, vol. 47 (17), pp. 4316-4326.
Stella V.J., "Prodrugs as Therapeutics," Expert Opinion on Therapeutic Patents, 2004, vol. 14 (3), pp. 277-280.
Street L.J., et al., "Synthesis and Serotonergic Activity of 5-(Oxadiazolyl)tryptamines: Patent Agonists for 5-HT1D Receptors," Journal of Medicinal Chemistry, 1993, vol. 36 (11), pp. 1529-1538.
Supplementary Partial European Search Report for Application No. 08770247, mailed on Mar. 16, 2012, 4 pages.
Testa B., et al., "Prodrug Research: Futile or Fertile?," Biochemical Pharmacology, 2004, vol. 68, pp. 2097-2106.
Thibonnier M., et al., "Vasopressin Receptor Antagonists in Heart Failure," Current Opinion in Pharmacology, 2003, vol. 3 (6), pp. 683-687.
Venkatesh S., et al., "Role of the Development Scientist in Compound Lead Selection and Optimization," Journal of Pharmaceutical Sciences, 2000, vol. 89 (2), pp. 145-154.
Wang Y., et al., "A Simple and Effcient One Step Synthesis of 1,3,4-Oxadiazoles Utilizing Polymer-Supported Reagents and Microwave Heating," Tetrahedron Letters, 2006, vol. 47 (1), pp. 105-108.
Webster M., "Ninth New Collegiate Dictionary" Definition of Prevention, Springfield, Massachusetts, 2000, pp. 933.
Wiffen P.J., et al., Gabapentin for Acute and Chronic Pain (Review), Cochrane Database of Systematic Reviews, 2005, vol. 20 (3), pp. 1-23.

(56) References Cited

OTHER PUBLICATIONS

Wilens T.E., et al., "ABT-089, A Neuronal Nicotinic Receptor Partial Agonist, for the Treatment of Attention-Deficit/Hyperactivity Disorder in Adults: Results of a Pilot Study," Biological Psychiatry, 2006, vol. 59 (11), pp. 1065-1070.

Yatagai T., et al., "Close Association of Severe Hyponatremia with Exaggerated Release of Arginine Vasopressin in Elderly Subjects with Secondary Adrenal Insufficiency," European Journal of Endocrinology, 2003, vol. 148 (2), pp. 221-226.

Banfi L., et al., "Ugi Multicomponent Reaction Followed by an Intermolecular Nucleophilic Substitution: Convergent Multicomponent Synthesis of 1-sulfonyl 1,4-diazepan-5-ones and of their Benzo-Fuzed Derivatives," Journal of Organic Chemistry, 2007, vol. 72 (6), pp. 2151-2160.

Chattopadhyay S.K., et al., "Formation of Medium-Ring Heterocycles by Diene and Enyne Metathesis," Tetrahedron, 2007, vol. 63, pp. 3919-3952.

Diaz G.J., et al., "The [3H]dofetilide Binding Assay is a Predictive Screening Tool for hERG Blockade and Proarrhythmia: Comparison of Intact Cell and Membrane Preparations and Effects of Altering [K+]o," Journal of Pharmacological and Toxicological Methods, 2004, vol. 50 (3), pp. 187-199.

Dorwold F.Z., "Side Reactions in Organic Synthesis," Wiley-VCH, 2005, Preface.

Final Office Action mailed May 10, 2012 for U.S. Appl. No. 12/746,715 filed Dec. 7, 2010.

Final Office Action mailed Feb. 13, 2012 for U.S. Appl. No. 12/746,688 filed Nov. 29, 2010.

Final Office Action mailed Feb. 24, 2012 for U.S. Appl. No. 12/746,700 filed Nov. 29, 2010.

Final Office Action mailed Mar. 26, 2013 for U.S. Appl. No. 12/746,688 filed Nov. 29, 2010.

Final Office Action mailed Feb. 27, 2012 for U.S. Appl. No. 12/746,707 filed Dec. 7, 2010.

Freshney R.I., et al., Culture of Animal Cells, A Manual of Basic Technique, 1983, Wiley & Sons, Inc., pp. 7-9.

International Search Report for Application No. PCT/EP2008/066931, mailed on May 12, 2009, 6 pages.

International Search Report for Application No. PCT/EP2008/066934, mailed on Jun. 4, 2009, 6 pages.

International Search Report for Application No. PCT/EP2008/066935 (WO2009/071690), mailed on Jun. 4, 2009, 6 pages.

Kocsis J., et al., "Effect of a Vasopressin Antagonist d(CH2)5Tyr(Met)AVP on the Development of Renal Vasospasm Induced by Estrin Plus Vasopressin Administration in Rats," Investigative Radiology, 1987, vol. 22 (12), pp. 973-977.

Lynch J.J., et al., "ABT-594 (A Nicotinic Acetylcholine Agonist): Anti-allodynia in a Rat Chemotherapy-induced Pain Model," European Journal of Pharmacology, 2005, vol. 509 (1), pp. 43-48.

Nakamura I., et al., "Transition-Metal-Catalyzed Reactions in Heterocyclic Synthesis," Chemical Reviews, 2004, vol. 104 (5), pp. 2127-2198.

Non-Final Office Action mailed Oct. 1, 2012 for U.S. Appl. No. 12/746,700 filed Nov. 29, 2010.

Non-Final Office Action mailed Oct. 1, 2012 for U.S. Appl. No. 12/746,707 filed Dec. 7, 2010.

Non-Final Office Action mailed Oct. 12, 2012 for U.S. Appl. No. 12/746,688 filed Nov. 29, 2010.

Non-Final Office Action mailed Aug. 19, 2011 for U.S. Appl. No. 12/746,700 filed Nov. 29, 2010.

Non-Final Office Action mailed Jul. 22, 2011 for U.S. Appl. No. 12/746,688 filed Nov. 29, 2010.

Non-Final Office Action mailed Jul. 22, 2011 for U.S. Appl. No. 12/746,707 filed Dec. 7, 2010.

Non-Final Office Action mailed Aug. 30, 2011 for U.S. Appl. No. 12/746,715 filed Dec. 7, 2010.

Smalley S.L., "Genetic Influences in Childhood-Onset Psychiatric Disorders: Autism and Attention-Deficit/hyperactivity Disorder," American Journal of Human Genetics, 1997, vol. 60 (6), pp. 1276-1282.

Wakefield B., Fluorinated Pharmaceuticals, Innovations in Pharmaceutical Technology, 2000, pp. 74-78.

Bonte J.P., et al., "Acyl-6 Benzoxazolinones (1 er memoire)," European Journal of Medicinal Chemistry, 1974, vol. 9 (5), pp. 491-496.

Final Office Action mailed Apr. 19, 2013 for U.S. Appl. No. 12/746,707 filed Dec. 7, 2010.

Notice of Allowance mailed Jun. 11, 2013 for U.S. Appl. No. 12/839,595 filed Jul. 20, 2010.

Notice of Allowance mailed Apr. 15, 2013 for U.S. Appl. No. 12/746,688 filed Nov. 29, 2010.

Notice of Allowance mailed Apr. 15, 2013 for U.S. Appl. No. 12/746,700 filed Nov. 29, 2010.

Notice of Allowance mailed May 28, 2013 for U.S. Appl. No. 12/746,715 filed Dec. 7, 2010.

Final Office Action mailed Dec. 3, 2012 for U.S. Appl. No. 13/361,488 filed Jan. 30, 2012.

Final Rejection mailed Oct. 10, 2013 for U.S. Appl. No. 13/590,261 filed Aug. 21, 2012.

Griebel G., et al., "The Vasopressin V1b Receptor as a Therapeutic Target in Stress-Related Disorders," Current Drug Targets. CNS and Neurological Disorders, 2003, vol. 2 (3), pp. 191-200.

Non-Final Office Action mailed Aug. 20, 2013 for U.S. Appl. No. 12/746,700 filed Nov. 29, 2010.

Non-Final Office Action mailed Oct. 8, 2013 for U.S. Appl. No. 13/080,071 filed Apr. 5, 2011.

Non-Final Office Action mailed Jul. 20, 2012 for U.S. Appl. No. 13/361,488 filed Jan. 30, 2012.

Notice of Allowance mailed Aug. 20, 2013 for U.S. Appl. No. 12/746,700 filed Nov. 29, 2010.

Office action mailed Aug. 1, 2013 for European Application No. 10163998.7 filed Dec. 12, 2007.

Final Office Action mailed Nov. 22, 2013 for U.S. Appl. No. 12/746,707 filed Dec. 7, 2010.

Notice of Allowance mailed Nov. 25, 2013 for U.S. Appl. No. 12/746,688 filed Nov. 29, 2010.

Notice of Allowance mailed Nov. 27, 2013 for U.S. Appl. No. 12/746,700 filed Nov. 29, 2010.

Final Office Action mailed Mar. 6, 2014 for U.S. Appl. No. 13/080,071 filed Apr. 5, 2011.

* cited by examiner

SUBSTITUTED OXINDOLE DERIVATIVES AND THEIR USE AS VASOPRESSIN RECEPTOR LIGANDS

RELATED APPLICATIONS

This application is filed under 35 USC §371 from PCT Patent Application No. PCT/EP2007/064622, which claims the priority benefit of German application serial numbers DE 102006062505.6, filed on Dec. 30, 2006; DE 102006062508.0, filed on Dec. 30, 2006; DE 102006062507.2, filed on Dec. 30, 2006; and DE 102006062506.4, filed on Dec. 30, 2006, the teachings and content of which are hereby incorporated by reference herein.

The present invention relates to novel substituted oxindole derivatives, to medicaments comprising them and to their use for treating diseases.

Vasopressin is an endogenous hormone which exerts widely diverse effects on organs and tissues. It is suspected that the vasopressin system is involved in various pathological states such as, for example, heart failure and high blood pressure. At present three receptors (V1a, V1b or V3 and V2) via which vasopressin mediates its numerous effects are known. Antagonists of these receptors are therefore being investigated as possible novel therapeutic approaches to the treatment of diseases (M. Thibonnier, Exp.Opin. Invest. Drugs 1998, 7(5), 729-740).

The present application describes novel substituted oxindoles carrying an arylsulphonyl group in position 1. 1-1-Phenylsulphonyl-1,3-dihydro-2H-indol-2-ones have previously been described as ligands of vasopressin receptors. WO 93/15051, WO95/18105, WO 98/25901, WO 01/55130, WO 01/55134, WO 01/64668 and WO 01/98295 describe derivatives derived from the oxindole skeleton and having arylsulphonyl groups in position 1. These compounds differ essentially in the substitution in position 3.

In particular, WO 93/15051 and WO 98/25901 describe 1-phenylsulphonyl-1,3-dihydro-2H-indol-2-ones in which the oxindole structure is substituted in position 3 by two alkyl radicals which may also together form a cycloalkyl radical (spiro linkage) as ligands of vasopressin receptors. Alternatively, the spiro ring may comprise heteroatoms, such as oxygen and nitrogen (optionally with substituents).

WO 95/18105 describes 1-phenylsulphonyl-1,3-dihydro-2H-indol-2-ones having a nitrogen atom in position 3 as ligands of vasopressin receptors. In addition, radicals which are selected from the group consisting of alkyl, cycloalkyl, phenyl and benzyl are attached in position 3 (in each case optionally with substituents).

WO 03/008407 describes 1-phenylsulphonyloxindoles in which pyridylpiperazines are attached via an oxycarbonyl group to the oxindole in position 3.

WO 2005/030755 describes as Example 108, the carbamate compound 4-(1-methylpiperidin-4-yl)piperazine-1-carboxylic acid 5-cyano-1-(2,4-dimethoxy-phenylsulphonyl)-3-(2-methoxypyridin-3-yl)-2-oxo-2,3-dihydro-1H-indol-3-yl ester (according to IUPAC nomenclature: 5-cyano-1-[(2,4-dimethoxyphenyl)sulphonyl]-3-(2-methoxypyridin-3-yl)-2-oxo-2,3-dihydro-1H-indol-3-yl-4-(1-methylpiperidin-4-yl)piperazine-1-carboxylate).

WO 06/005609 describes the 2-ethoxyphenyl urea compounds N-[5-cyano-1-[(2,4-dimethoxyphenyl)sulphonyl]-3-(2-ethoxyphenyl)-2-oxo-2,3-dihydro-1H-indol-3-yl]-4-(1-methylpiperidin-4-yl)piperazine-1-carboxamide (as Example 119) and N-[5-cyano-1-[(2,4-dimethoxyphenyl) sulphonyl]-3-(2-ethoxyphenyl)-2-oxo-2,3-dihydro-1H-indol-3-yl)-4-(4-methylpiperazin-1-yl)piperidine-1-carboxamide (as Example 128).

In addition to the binding affinity to the vasopressin V1b receptor, further properties may be advantageous in the treatment and/or prophylaxis of vasopressin-dependent disorders, such as, for example:

1.) a selectivity for the vasopressin V1b receptor over the vasopressin V1a receptor, i.e. the quotient of the binding affinity to the V1a receptor (Ki(V1a) (determined in the unit "nanomolar (nM)") and the binding affinity to the V1b receptor (Ki(V1b)) (determined in the unit "nanomolar (nM)"). The greater the quotient Ki(V1a)/Ki(V1b), the greater the V1b selectivity;

2.) a selectivity for the vasopressin V1b receptor over the vasopressin V2 receptor, i.e. the quotient of the binding affinity to the V2 receptor (Ki(V2) (determined in the unit "nanomolar (nM)") and the binding affinity to the V1b receptor (Ki(V1b)) (determined in the unit "nanomolar (nM)"). The greater the quotient Ki(V2)/Ki(V1b), the greater the V1b selectivity;

3.) a selectivity for the vasopressin V1b receptor over the oxytocin OT receptor, i.e. the quotient of the binding affinity to the OT receptor (Ki(OT) (determined in the unit "nanomolar (nM)") and the binding affinity to the V1b receptor (Ki (V1b)) (determined in the unit "nanomolar (nM)"). The greater the quotient Ki(OT)/Ki(V1b), the greater the V1b selectivity;

4.) the metabolic stability, determined, for example, using the half-life determined in vitro in liver microsomes of various species (for example rat or human);

5.) only minor, if any, inhibition of cytochrom P450 (CYP) enzymes: cytochrom P450 (GYP) is the name for a superfamily of haem proteins having enzymatic activity (oxidases). They are also of particular importance for the degradation (metabolism) of foreign substances, such as pharmaceutics or xenobiotics, in mammalian organisms. The most important representatives of the types and subtypes of CYP in the human organism are: CYP 1A2, CYP 2C9, CYP 2D6 and CYP 3A4. When CYP 3A4 inhibitors (for example grapefruit juice, cimetidine, erythromycin) and medicaments which are degraded via this enzyme system and which thus compete for the same binding site at the enzyme are administered simultaneously, their degradation may be slowed down, and actions and side-effects of the medicament administered may be enhanced in an unwanted manner;

6.) suitable solubility in water (in mg/ml);

7.) suitable pharmacokinetics (temporal profile of the concentration of the compound according to the invention in the plasma or in tissues, for example brain). Pharmacokinetics may be described by the following parameters: half-life, distribution volume, plasma clearance, AUC ("area under the curve", area under the concentration-time curve), oral bioavailability, the brain/plasma ratio;

8.) a certain proportion of the active substance is present attached to plasma proteins (drug/plasma protein binding (PPB) value);

9.) no or only minor blockage of the hERG channel: compounds which block the hERG channel may prolong the QT interval, thus leading to serious irregularities of pulse (for example "torsade de pointes"). Using a displacement assay described in the literature with radioactively labelled dofetilide (G. J. Diaz et al., Journal of Pharmacological and Toxicological Methods, 50 (2004), 187-199), it is possible to determine the potential of compounds of blocking the hERG channels. The lower the IC50 in this "dofetilide assay", the more likely a potent hERG blockage. In addition, the blockage of the hERG channel may be measured by electrophysical experiments using cells transfected with the hERG channel, by "whole-cell patch clamping" (G. J. Diaz et al., Journal of Pharmacological and Toxicological Methods, 50 (2004), 187-199).

It is an object of the present invention to provide a compound with high and selective activity, preferably in particular for the vasopressin V1b receptor, for the treatment or prophylaxis of various vasopressin-dependent diseases. In addition, the substance according to the invention should have one or more of the advantages 1.) to 9.) mentioned above, in particular a suitable selectivity for the V1b receptor over the V1a receptor.

This object is achieved by compounds of the general formula (I)

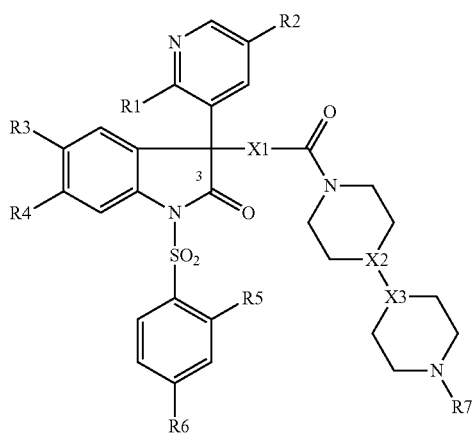

in which
R1 is ethoxy;
R2 is hydrogen;
R3 is cyano;
R4 is hydrogen;
R5 is hydrogen, methoxy or ethoxy;
R6 is hydrogen or methoxy;
R7 is hydrogen, methyl, ethyl, n-propyl or isopropyl;
X1 is —NH—;
X2 is N or CH;
X3 is N or CH;
where X2 and X3 are not simultaneously N (that is to say are a nitrogen atom); and by the pharmaceutically acceptable salts, tautomeric forms, and prodrugs thereof.

Accordingly, the present invention relates to compounds of the general formula (I) (also "compounds (I)" below), including the tautomeric forms thereof, and the pharmaceutically acceptable salts of the compounds (I) and the prodrugs of the compounds (I).

A preferred subject-matter of the invention are compounds of the general formula (I) in which
R1 is ethoxy;
R2 is hydrogen;
R3 is cyano;
R4 is hydrogen;
R5 is hydrogen or methoxy, in particular methoxy;
R6 is hydrogen or methoxy, in particular methoxy;
R7 is hydrogen, methyl, ethyl, n-propyl or isopropyl;
X1 is —NH—;
X2 is N or CH;
X3 is N or CH;
where X2 and X3 are not simultaneously a nitrogen atom; and the pharmaceutically acceptable salts, tautomeric forms, and prodrugs thereof.

A particularly preferred subject-matter of the invention are compounds of the general formula (I) in which
R1 is ethoxy;
R2 is hydrogen;
R3 is cyano;
R4 is hydrogen;
R5 is hydrogen or methoxy, in particular methoxy;
R6 is hydrogen or methoxy, in particular methoxy, in particular methyl or ethyl;
R7 is hydrogen, methyl or ethyl;
X1 is —NH—;
X2 is N;
X3 is CH;
and the pharmaceutically acceptable salts, tautomeric forms, and prodrugs thereof.

A further particularly preferred subject-matter of the invention are compounds of the general formula (I) in which
R1 is ethoxy;
R2 is hydrogen;
R3 is cyano;
R4 is hydrogen;
R5 is hydrogen or methoxy, in particular methoxy;
R6 is hydrogen or methoxy, in particular methoxy;
R7 is hydrogen, methyl or ethyl, in particular methyl or ethyl;
X1 is —NH—;
X2 is CH;
X3 is N;
and the pharmaceutically acceptable salts, tautomeric forms, and prodrugs thereof.

A further particularly preferred subject-matter of the invention are compounds of the general formula (I) in which
R1 is ethoxy;
R2 is hydrogen;
R3 is cyano;
R4 is hydrogen;
R5 is hydrogen or methoxy, in particular methoxy;
R6 is hydrogen or methoxy, in particular methoxy;
R7 is hydrogen, methyl or ethyl, in particular methyl or ethyl;
X1 is —NH—;
X2 is CH;
X3 is CH;
and the pharmaceutically acceptable salts, tautomeric forms, and prodrugs thereof.

A further particularly preferred subject-matter of the invention are compounds of the general formula (I) in which
R1 is ethoxy;
R2 is hydrogen;
R3 is cyano;
R4 is hydrogen;
R5 is methoxy;
R6 is methoxy;
R7 is methyl or ethyl;
X1 is —NH—;
X2 is CH and X3 is N; or
X2 is N and X3 is CH;
and the pharmaceutically acceptable salts, tautomeric forms, and prodrugs thereof.

Examples of preferred embodiments of the present invention are compounds according to the general formula (I), and the pharmaceutically acceptable salts, tautomeric forms, and prodrugs thereof, in which
R1 is ethoxy,
R2 is hydrogen,
R3 is cyano, R4 is hydrogen,
X1 is NH,
and in which the radicals X2, X3, R5, R6 and R7 have in each case the meanings listed in one of the rows of Table 1 below.

TABLE 1

| Example No. | X2 | X3 | R5 | R6 | R7 |
|---|---|---|---|---|---|
| 1 | N | CH | methoxy | methoxy | methyl |
| 2 | N | CH | methoxy | H | methyl |
| 3 | N | CH | ethoxy | H | methyl |
| 4 | N | CH | H | H | methyl |
| 5 | N | CH | H | methoxy | methyl |
| 6 | N | CH | ethoxy | methoxy | methyl |
| 7 | N | CH | methoxy | methoxy | ethyl |
| 8 | N | CH | methoxy | H | ethyl |
| 9 | N | CH | ethoxy | H | ethyl |
| 10 | N | CH | H | H | ethyl |
| 11 | N | CH | H | methoxy | ethyl |
| 12 | N | CH | ethoxy | methoxy | ethyl |
| 13 | N | CH | methoxy | methoxy | n-propyl |
| 14 | N | CH | methoxy | H | n-propyl |
| 15 | N | CH | ethoxy | H | n-propyl |
| 16 | N | CH | H | H | n-propyl |
| 17 | N | CH | H | methoxy | n-propyl |
| 18 | N | CH | ethoxy | methoxy | n-propyl |
| 19 | N | CH | methoxy | methoxy | isopropyl |
| 20 | N | CH | methoxy | H | isopropyl |
| 21 | N | CH | ethoxy | H | isopropyl |
| 22 | N | CH | H | H | isopropyl |
| 23 | N | CH | H | methoxy | isopropyl |
| 24 | N | CH | ethoxy | methoxy | isopropyl |
| 25 | N | CH | methoxy | methoxy | H |
| 26 | N | CH | methoxy | H | H |
| 27 | N | CH | ethoxy | H | H |
| 28 | N | CH | H | H | H |
| 29 | N | CH | H | methoxy | H |
| 30 | N | CH | ethoxy | methoxy | H |
| 31 | CH | N | methoxy | methoxy | methyl |
| 32 | CH | N | methoxy | H | methyl |
| 33 | CH | N | ethoxy | H | methyl |
| 34 | CH | N | H | H | methyl |
| 35 | CH | N | H | methoxy | methyl |
| 36 | CH | N | ethoxy | methoxy | methyl |
| 37 | CH | N | methoxy | methoxy | ethyl |
| 38 | CH | N | methoxy | H | ethyl |
| 39 | CH | N | ethoxy | H | ethyl |
| 40 | CH | N | H | H | ethyl |
| 41 | CH | N | H | methoxy | ethyl |
| 42 | CH | N | ethoxy | methoxy | ethyl |
| 43 | CH | N | methoxy | methoxy | n-propyl |
| 44 | CH | N | methoxy | H | n-propyl |
| 45 | CH | N | ethoxy | H | n-propyl |
| 46 | CH | N | H | H | n-propyl |
| 47 | CH | N | H | methoxy | n-propyl |
| 48 | CH | N | ethoxy | methoxy | n-propyl |
| 49 | CH | N | methoxy | methoxy | isopropyl |
| 50 | CH | N | methoxy | H | isopropyl |
| 51 | CH | N | ethoxy | H | isopropyl |
| 52 | CH | N | H | H | isopropyl |
| 53 | CH | N | H | methoxy | isopropyl |
| 54 | CH | N | ethoxy | methoxy | isopropyl |
| 55 | CH | N | methoxy | methoxy | H |
| 56 | CH | N | methoxy | H | H |
| 57 | CH | N | ethoxy | H | H |
| 58 | CH | N | H | H | H |
| 59 | CH | N | H | methoxy | H |
| 60 | CH | N | ethoxy | methoxy | H |
| 61 | CH | CH | methoxy | methoxy | methyl |
| 62 | CH | CH | methoxy | H | methyl |
| 63 | CH | CH | ethoxy | H | methyl |
| 64 | CH | CH | H | H | methyl |
| 65 | CH | CH | H | methoxy | methyl |
| 66 | CH | CH | ethoxy | methoxy | methyl |
| 67 | CH | CH | methoxy | methoxy | ethyl |
| 68 | CH | CH | methoxy | H | ethyl |
| 69 | CH | CH | ethoxy | H | ethyl |
| 70 | CH | CH | H | H | ethyl |
| 71 | CH | CH | H | methoxy | ethyl |
| 72 | CH | CH | ethoxy | methoxy | ethyl |
| 73 | CH | CH | methoxy | methoxy | n-propyl |
| 74 | CH | CH | methoxy | H | n-propyl |
| 75 | CH | CH | ethoxy | H | n-propyl |
| 76 | CH | CH | H | H | n-propyl |
| 77 | CH | CH | H | methoxy | n-propyl |
| 78 | CH | CH | ethoxy | methoxy | n-propyl |
| 79 | CH | CH | methoxy | methoxy | isopropyl |
| 80 | CH | CH | methoxy | H | isopropyl |
| 81 | CH | CH | ethoxy | H | isopropyl |
| 82 | CH | CH | H | H | isopropyl |
| 83 | CH | CH | H | methoxy | isopropyl |
| 84 | CH | CH | ethoxy | methoxy | isopropyl |
| 85 | CH | CH | methoxy | methoxy | H |
| 86 | CH | CH | methoxy | H | H |
| 87 | CH | CH | ethoxy | H | H |
| 88 | CH | CH | H | H | H |
| 89 | CH | CH | H | methoxy | H |
| 90 | CH | CH | ethoxy | methoxy | H |

In particular, the present invention relates to the following compound of the formula Ia (which corresponds to compound Example 1 of table 1)

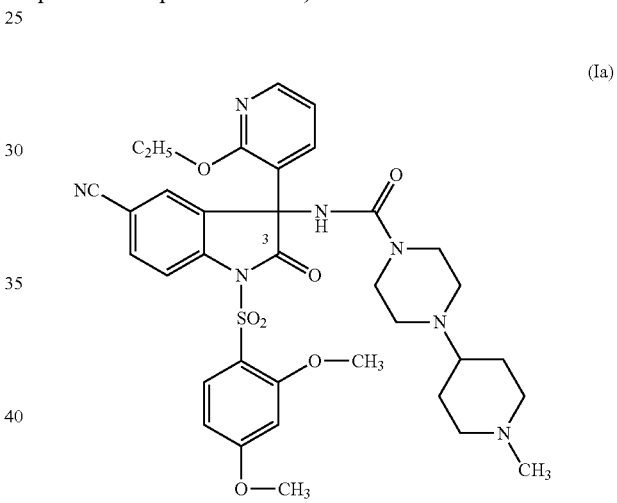

and also the pharmaceutically acceptable salts, tautomeric forms, and prodrugs of 1a.

In particular, the present invention also relates to the compound Example 7 of table 1 and also to the pharmaceutically acceptable salts, tautomeric forms, and prodrugs thereof.

In particular, the present invention also relates to the compound Example 31 of table 1 and also to the pharmaceutically acceptable salts, tautomeric forms, and prodrugs thereof.

In particular, the present invention also relates to the compound Example 37 of table 1 and also to the pharmaceutically acceptable salts, tautomeric forms, and prodrugs thereof.

The compounds (I) or (Ia) of the invention have a centre of chirality in position 3 of the 2-oxindole ring. The compounds according to the invention of the general formula (I) or (Ia) may therefore be present as a 1:1 mixture of enantiomers (racemate), or as a non-racemic mixture of enantiomers in which one of the two enantiomers, i.e. either the (laevorotatory) enantiomer which turns the plane of polarization of linear polarized light to the left ((−)-enantiomer below), or the (dextrorotatory) enantiomer which turns the plane of polarization of linear polarized light to the right ((+)-enantiomer below), is enriched, or as essentially enantiomerically pure compounds (enantiomeric excess ee >90%), i.e. as essentially enantiomerically pure (−)-enantiomer or (+)-enantiomer. Preferably, the compounds are present as essentially enantiomerically pure compounds. Particular preference is given to compounds which are essentially enantiomerically pure (ee >90%).

The invention therefore provides the pure enantiomers as well as their mixtures, for example, mixtures in which one enantiomer is present in enriched form, but also the racemates. The invention also provides the pharmaceutically acceptable salts, the tautomers and the prodrugs of the pure enantiomers of (I) or (Ia), and the enantiomer mixtures in the form of the pharmaceutically acceptable salts, the tautomers and the prodrugs of (I) or (Ia).

Preferred embodiments of the invention are compounds of the general formula (I) or (Ia), as defined above, which are characterized in that they are present in optically active form and that they are in each case the enantiomer, which rotates the plane of polarization of polarized light to the left, (i.e. the laevorotatory enantiomer) of the compound of the general formula (I) in question in the form of the free base, or a pharmaceutically acceptable salt, a tautomeric form or a prodrug thereof. Below, the laevorotatory enantiomers of the compounds (I) or (Ia) are also referred to as (−)-enantiomers.

Preferred embodiments of the invention are those compounds of the general formula (I) or (Ia), as defined above, which are characterized in that they are present in optically active form, where the absolute configuration of the chiral C-3 ring carbon atom of these compounds corresponds to the absolute configuration at C-3 of the (−)-enantiomer of the compound of the formula (Ia) in the form of the free base. This configuration is also referred to below as the "preferred configuration". X-Ray structure analyses have shown that the (−)-enantiomer of the compounds of the formula (Ia) has S configuration with respect to the centre of asymmetry at the carbon atom of position 3 of the oxindole ring.

According to the invention, preference is given to compounds of the general formula (I) or (Ia), tautomers thereof, pharmaceutically acceptable salts thereof and prodrugs thereof, as defined above, in which the corresponding (−)-enantiomer is present in an optical purity (enantiomeric excess, ee) of greater than 50%.

According to the invention, preference is given to compounds of the general formula (I) or (Ia), tautomers thereof, pharmaceutically acceptable salts thereof and prodrugs thereof, as defined above, in which the enantiomer having the preferred absolute configuration at the C-3 ring carbon atom is present in an optical purity (enantiomeric excess, ee) of greater than 50%.

According to the invention, preference is given to compounds of the general formula (I) or (Ia), tautomers thereof, pharmaceutically acceptable salts thereof and prodrugs thereof, as defined above, in which the corresponding (−)-enantiomer is present in an optical purity (enantiomeric excess, ee) of greater than 90%.

According to the invention, preference is given to compounds of the general formula (I) or (Ia), tautomers thereof, pharmaceutically acceptable salts thereof and prodrugs thereof, as defined above, in which the enantiomer having the preferred absolute configuration at the C-3 ring carbon atom is present in an optical purity (enantiomeric excess, ee) of greater than 90%.

Likewise preferred embodiments of the invention are compounds of the general formula (I) or (Ia) as defined above, which are characterized in that they are present in optically inactive form, that is to say in the form of the racemate, or in the form of a pharmaceutically acceptable salt, a tautomeric form or a prodrug of the racemate.

A further subject-matter of the present invention relates to medicaments comprising at least one compound of the general formula (I) or (Ia) and/or a pharmaceutically acceptable salt or a prodrug thereof as defined above.

A further subject-matter of the present invention relates to compounds of the general formula (I) or (Ia) and/or a pharmaceutically acceptable salt or a prodrug thereof as defined above for use as a medicament.

A further subject-matter of the present invention relates to the compounds of the formula (I) or (Ia) and/or a pharmaceutically acceptable salt or a prodrug thereof as defined above for use in therapy or prophylaxis of a disease, in particular a vasopressin-dependent disease or a disease mentioned herein.

A further subject-matter of the present invention relates to the use of at least one compound of the general formula (I) or (Ia) and/or a pharmaceutically acceptable salt or a prodrug thereof as defined above for the treatment and/or prophylaxis of at least one vasopressin-dependent disease and/or for the manufacture of a medicament for the treatment and/or a prophylaxis of at least one vasopressin-dependent disease.

Vasopressin-dependent diseases are those in which the progression of the disease depends at least in part on vasopressin, i.e. diseases where the vasopressin level, which may contribute directly or indirectly to the disease picture, is elevated.

The present invention also relates to the use of the compounds (I) or (Ia) according to the invention and/or a pharmaceutically acceptable salt or a prodrug thereof for the treatment and/or prophylaxis of diseases in which the progression of the disease depends at least in part on vasopressin, i.e. diseases where the vasopressin level, which may contribute directly or indirectly to the disease picture, is elevated. The present invention also relates to the use of the compounds (I) or (Ia) according to the invention and/or a pharmaceutically acceptable salt or a prodrug thereof for preparing a medicament for the treatment and/or prophylaxis of such a disease.

The present invention relates in particular to the use of at least one compound of the general formula (I) or (Ia) and/or a pharmaceutically acceptable salt or a prodrug thereof as defined above for the treatment and/or prophylaxis of at least one disorder selected from the group consisting of diabetes, in particular diabetes insipidus, insulin resistance, nocturnal enuresis, incontinence, diseases in which blood coagulation disorders occur, and/or for delaying micturition and the use thereof for the manufacture of a medicament for the treatment and/or prophylaxis of at least one of said diseases.

The present invention relates in particular to the use of at least one compound of the general formula (I) or (Ia) and/or a pharmaceutically acceptable salt or a prodrug thereof as defined above for the treatment and/or prophylaxis of at least one disorder selected from the group consisting of hypertension, pulmonary hypertension, heart failure, myocardial infarction, coronary spasm, unstable angina, PTCA (percutaneous transluminal coronary angioplasty), ischemias of the heart, disorders of the renal system, edemas, renal vasospasm, necrosis of the renal cortex, hyponatremia, hypokalemia, Schwartz-Bartter syndrome, disorders of the gastrointestinal tract, gastritic vasospasm, hepatocirrhosis, gastric and intestinal ulcer, emesis, emesis occurring during chemotherapy, and travel sickness, and the use thereof for the manufacture of a medicament for the treatment and/or prophylaxis of at least one of said diseases.

The compounds (I) or (Ia) of the invention, their salts, their tautomers and their prodrugs can also be used for the treatment of various vasopressin-dependent complaints which exhibit central nervous causes or alterations in the HPA axis (hypothalamic pituitary adrenal axis), for example for affective disorders such as depressive disorders and bipolar disorders. These include for example dythymic disorders, phobias, post-traumatic stress disorders, general anxiety disorders, panic disorders, seasonal depressions and sleep disorders.

The compounds (I) or (Ia) of the invention, their salts, their tautomers and their prodrugs can likewise be employed for treatment in cases of anxiety disorders and stress-dependent anxiety disorders such as, for example, generalized anxiety disorders, phobias, post-traumatic anxiety disorders, panic anxiety disorders, obsessive-compulsive anxiety disorders, acute stress-dependent anxiety disorders and social phobia. The compounds of the invention can further be employed also for the treatment of memory impairments, Alzheimer's disease, psychoses, psychotic disorders, sleep disorders and/or Cushing's syndrome, and all stress-dependent diseases.

A further subject-matter of the invention relates to the use of at least one compound of the general formula (I) or (Ia) and/or a pharmaceutically acceptable salt or a prodrug thereof as defined above for the treatment of affective disorders and/or for the manufacture of a medicament for the treatment of affective disorders.

A further subject-matter of the invention relates to the use of at least one compound of the general formula (I) or (Ia) and/or a pharmaceutically acceptable salt or a prodrug thereof as defined above for the treatment of anxiety disorders and/or stress-dependent anxiety disorders and/or for the manufacture of a medicament for the treatment of anxiety disorders and/or stress-dependent anxiety disorders.

A further subject-matter of the invention relates to the use of at least one compound of the general formula (I) or (Ia) and/or a pharmaceutically acceptable salt or a prodrug thereof as defined above for the treatment of memory impairments and/or Alzheimer's disease and/or for the manufacture of a medicament for the treatment of memory impairments and/or Alzheimer's disease.

A further subject-matter of the invention relates to the use of at least one compound of the general formula (I) or (Ia) and/or a pharmaceutically acceptable salt or a prodrug thereof as defined above for the treatment of psychoses and/or psychotic disorders and/or for the manufacture of a medicament for the treatment of psychoses and/or psychotic disorders.

A further subject-matter of the invention relates to the use of at least one compound of the general formula (I) or (Ia) and/or a pharmaceutically acceptable salt or a prodrug thereof as defined above for the treatment of Cushing's syndrome or other stress-dependent diseases and/or for the manufacture of a medicament for the treatment of Cushing's syndrome or other stress-dependent diseases.

A further subject-matter of the invention relates to the use of at least one compound of the general formula (I) or (Ia) and/or a pharmaceutically acceptable salt or a prodrug thereof as defined above for the treatment of sleep disorders and/or for the manufacture of a medicament for the treatment of sleep disorders.

A further subject-matter of the invention relates to the use of at least one compound of the general formula (I) or (Ia) and/or a pharmaceutically acceptable salt or a prodrug thereof as defined above for the treatment of depressive disorders and/or for the manufacture of a medicament for the treatment of depressive disorders.

A further subject-matter of the invention relates to the use of at least one compound of the general formula (I) or (Ia) and/or a pharmaceutically acceptable salt or a prodrug thereof as defined above for the treatment of childhood onset mood disorders and/or for the manufacture of a medicament for the treatment of childhood onset mood disorders. The term "childhood onset mood disorders" is understood to mean mood disorders and depressions which begin as early as childhood.

A further subject-matter of the invention relates to the use of at least one compound of the general formula (I) or (Ia) and/or a pharmaceutically acceptable salt or a prodrug thereof as defined above for the treatment of vasomotor symptoms and/or thermoregulatory dysfunctions, such as, for example, the "hot flush" symptom.

A further subject-matter of the invention relates to the use of at least one compound of the general formula (I) or (Ia) and/or a pharmaceutically acceptable salt or a prodrug thereof as defined above for the treatment and/or prophylaxis of drug dependencies, medicament dependencies and/or dependencies mediated by other factors, for the treatment and/or prophylaxis of stress caused by the withdrawal of one or more factors mediating the dependency and/or for the treatment and/or prophylaxis of stress-induced relapses into the drug dependencies, medicament dependencies and/or dependencies mediated by other factors.

A further subject-matter of the invention relates to the use of at least one compound of the general formula (I) or (Ia) and/or a pharmaceutically acceptable salt or a prodrug thereof as defined above for the treatment and/or prophylaxis of schizophrenia and/or psychosis.

A further subject-matter of the invention relates to a method for the treatment and/or prophylaxis of at least one disorder selected from the group consisting of diabetes, in particular diabetes insipidus, insulin resistance, nocturnal enuresis, incontinence, diseases in which blood coagulation disorders occur, and for delaying micturition in a patient, characterized in that an effective amount of at least one compound of the general formula (I) or (Ia) and/or a pharmaceutically acceptable salt or a prodrug thereof is administered to the patient.

A further subject-matter of the invention relates to a method for the treatment and/or prophylaxis of at least one disorder selected from the group consisting of hypertension, pulmonary hypertension, heart failure, myocardial infarction, coronary spasm, unstable angina, PTCA (percutaneous transluminal coronary angioplasty), ischemias of the heart, disorders of the renal system, edemas, renal vasospasm, necrosis of the renal cortex, hyponatremia, hypokalemia, Schwartz-Bartter syndrome, disorders of the gastrointestinal tract, gastritic vasospasm, hepatocirrhosis, gastric and intestinal ulcer, emesis, emesis occurring during chemotherapy, and travel sickness in a patient, characterized in that an effective amount of at least one compound of the general formula (I) or (Ia) and/or a pharmaceutically acceptable salt or a prodrug thereof is administered to the patient.

A further subject-matter of the invention relates to a method for the treatment and/or prophylaxis of affective disorders in a patient, characterized in that an effective amount of at least one compound of the general formula (I) or (Ia) and/or a pharmaceutically acceptable salt or a prodrug thereof is administered to the patient.

A further subject-matter of the invention relates to a method for the treatment of anxiety disorders and/or stress-dependent anxiety disorders in a patient, characterized in that an effective amount of at least one compound of the general formula (I) or (Ia) and/or a pharmaceutically acceptable salt or a prodrug thereof is administered to the patient.

A further subject-matter of the invention relates to a method for the treatment of memory impairments and/or Alzheimer's disease in a patient, characterized in that an effective amount of at least one compound of the general formula (I) or (Ia) and/or a pharmaceutically acceptable salt or a prodrug thereof is administered to the patient.

A further subject-matter of the invention relates to a method for the treatment of psychoses and/or psychotic disorders in a patient, characterized in that an effective amount of at least one compound of the general formula (I) or (Ia) and/or a pharmaceutically acceptable salt or a prodrug thereof is administered to the patient.

A further subject-matter of the invention relates to a method for the treatment of Cushing's syndrome in a patient, characterized in that an effective amount of at least one compound of the general formula (I) or (Ia) and/or a pharmaceutically acceptable salt or a prodrug thereof is administered to the patient.

A further subject-matter of the invention relates to a method for the treatment of sleep disorders in a patient, characterized in that an effective amount of at least one compound of the general formula (I) or (Ia) and/or a pharmaceutically acceptable salt or a prodrug thereof is administered to the patient.

A further subject-matter of the invention relates to a method for the treatment of depressive disorders in a patient, characterized in that an effective amount of at least one compound of the general formula (I) or (Ia) and/or a pharmaceutically acceptable salt or a prodrug thereof is administered to the patient.

A further subject-matter of the invention relates to a method for the treatment and/or prophylaxis of vasomotor symptoms and/or thermoregulatory dysfunctions, such as, for example, the "hot flush" symptom, in a patient, characterized in that an effective amount of at least one compound of the general formula (I) or (Ia) and/or a pharmaceutically acceptable salt or a prodrug thereof is administered to the patient.

A further subject-matter of the invention relates to a method for the treatment and/or prophylaxis of drug dependencies, medicament dependencies and/or dependencies mediated by other factors, for the treatment and/or prophylaxis of stress caused by the withdrawal of one or more factors mediating the dependency and/or for the treatment and/or prophylaxis of stress-induced relapses in the drug dependencies, medicament dependencies and/or dependencies mediated by other factors, in a patient, characterized in that an effective amount of at least one compound of the general formula (I) or (Ia) and/or pharmaceutically acceptable salt or a prodrug thereof is administered to the patient.

A further subject-matter of the invention relates to a method for the treatment and/or prophylaxis of schizophrenia and/or psychosis in a patient, characterized in that an effective amount of at least one compound of the general formula (I) or (Ia) and/or a pharmaceutically acceptable salt or a prodrug thereof is administered to the patient.

A further subject-matter of the invention relates to a method as defined above, which is characterized in that the patient is a mammal, preferably a human or a nonhuman mammal or a nonhuman transgenic mammal.

The compounds of the general formula (I) or (Ia), their pharmaceutically acceptable salts and prodrugs as defined above can be prepared by a skilled worker with knowledge of the technical teaching of the invention in implementation and/or in analogous implementation of process steps known per se.

A further preferred embodiment relates to compounds of the general formula (I) or (Ia), their tautomers, their prodrugs thereof and their pharmaceutically acceptable salts as described above, which are characterized in that they are selective for the vasopressin receptor subtype V1b over at least one of the closely related vasopressin/oxytocin receptor subtypes (for example vasopressin V1a, vasopressin V2 and/or oxytocin).

A further preferred embodiment relates to compounds of the general formula (I) or (Ia), their tautomers, their prodrugs thereof and their pharmaceutically acceptable salts as described above, which are characterized in that they have improved metabolic stability.

The metabolic stability of a compound can be determined, for example, by incubating a solution of this compound with liver microsomes from particular species (for example rat, dog or human) and determining the half-life of the compound under these conditions (R S Obach, Curr Opin Drug Discov Devel. 2001, 4, 36-44). It is possible to conclude from an observed larger half-life that the metabolic stability of the compound is improved. The stability in the presence of human liver microsomes is of particular interest since it makes it possible to predict the metabolic degradation of the compound in the human liver. Compounds with increased metabolic stability (determined in the liver microsome test) are therefore probably also degraded more slowly in the liver. The slower metabolic degradation in the liver can lead to higher and/or longer-lasting concentrations (effective levels) of the compound in the body, so that the elimination half-life of the compounds according to the invention is increased. Increased and/or longer-lasting effective levels may lead to a better efficacy of the compound in the treatment or prophylaxis of various vasopressin-dependent diseases. An improved metabolic stability may additionally lead to an increased bioavailability after oral administration, because the compound is subjected, after being absorbed in the intestine, to less metabolic degradation in the liver (so-called first pass effect). An increased oral bioavailability may, because the concentration (effective level) of the compound is increased, lead to a better efficacy of the compound after oral administration.

A further preferred embodiment relates to compounds of the general formula (I) as described above, characterized in that, in patients or relevant animal models allowing prognostic statements on therapeutic application, they have improved pharmacological activity compared to the oxindole compounds known from the prior art.

Each of the stated preferred definitions of a variable may be combined with any definitions of the remaining variables.

The invention relates in particular to compounds of the general formula (I) which are selected from the group consisting of the examples, listed below, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 and 90, and also to their tautomeric forms, their prodrugs and in particular their physiologically acceptable salts, and their non-salt forms such as hydrates and/or solvates. Particular preference is given to providing the abovementioned compounds in the form of the free base or in the form of acid addition salts.

The invention in particular also relates to the (−)-enantiomers of the Examples 1 to 90 in accordance with the general formula (I) selected from the compounds of the examples, listed below, 1B, 2B, 3B, 4B, 5B, 6B, 7B, 8B, 9B, 10B, 11B, 12B, 13B, 14B, 15B, 16B, 17B, 18B, 19B, 20B, 21B, 22B, 23B, 24B, 25B, 26B, 27B, 28B, 29B, 30B, 31B, 32B, 33B, 34B, 35B, 36B, 37B, 38B, 39B, 40B, 41B, 42B, 43B, 44B, 45B, 46B, 47B, 48B, 49B, 50B, 51B, 52B, 53B, 54B, 55B, 56B, 57B, 58B, 59B, 60B, 61B, 62B, 63B, 64B, 65B, 66B, 67B, 68B, 69B, 70B, 71B, 72B, 73B, 74B, 75B, 76B, 77B, 78B, 79B, 80B, 81B, 82B, 83B, 84B, 85B, 86B, 87B, 88B, 89B and 90B, and also to tautomeric forms, prodrugs and in particular physiologically acceptable salts, and non-salt forms such as hydrates and/or solvates of compounds of the formula (I). Particular preference is given to providing the abovementioned corn pounds in the form of the free base or in the form of acid addition salts.

The term "prodrugs" is to be understood as meaning those compounds which are metabolized in viva to the compounds according to the invention. Typical examples of prodrugs are described in C. G. Wermeth (Ed.): The Practice of Medicinal Chemistry, Academic Press, San Diego, 1996, pages 671-715. They include, for example, phosphates, carbamates or amino acids, esters and others. In the present invention suitable prodrugs of the compounds of the formual are compounds of the formula I, where the nitrogen atom that carries R7 is part of an amide/peptide group, i.e. the nitrogen carries a acyl group such as C1-C4-alkylcarbonyl e.g. acetyl, propionyl, n-butyryl (n-propylcarbonyl), isobutyryl, n-butylcarbonyl oder tert-butylcarbonyl (pivaloyl), benzoyl, CO bound radical derived from an amino acid such as a CO bound radical derived from glycine, alanine, serine, phenylalanine etc. Suitable prodrugs also include alkylcarbonyloxyalkylcarbamate, wherein the radical R7 in formula I is a moiety of the formula —C(=O)—O—CHR$^B$—O—C(=O)—Rb wherein R$^a$ and R$^b$ are independently of each other are selected from $C_1$-$C_4$-alkyl. Such carbamates have been generally described by J. Alexander, R. Cargill, S. R. Michelson, H. Schwam, J. Medicinal Chem. 1988, 31(2), 318-322. These groups are cleaved under metabolic conditions to yield a compound of the formula I, wherein R7 is hydrogen.

The invention furthermore relates to the pharmaceutically acceptable salts of compounds of the formula I, which are also referred to as physiologically acceptable salts. The salts are generally obtainable by reacting the free base of the compounds (I) according to the invention with a suitable acid. Suitable acids are listed, for example, in "Fortschritte der Arzneimittelforschung" [Advances in Drug Research], 1966, Birkhäuser Verlag, Vol. 10, pp. 224-285. They include, for example, hydrochloric acid, citric acid, tartaric acid, lactic acid, phosphoric acid, methanesulphonic acid, acetic acid, formic acid, maleic acid and fumaric acid.

The compounds of the invention are effective after administration by various routes. The administration can, for example, be carried out intravenously, intramuscularly, subcutaneously, topically, intratracheally, intranasally, transdermally, vaginally, rectally, sublingually, buccally or orally and is frequently carried out intravenously, intramuscularly or in particular orally.

The present invention also relates to pharmaceutical compositions which comprise a compound (I) of the invention, and/or a tautomer, and/or a pharmaceutically acceptable salt and/or a prodrug thereof and suitable pharmaceutical carriers (drug carriers). The amount of compound I in the pharmaceutical composition may depend on the formulation type of the composition and may be e.g. in the range from 0.0001 mg/g to 1 g/g in particular from 0.001 mg/g to 0.5 g/g of the composition.

These drug carriers are chosen according to the pharmaceutical form and the desired mode of administration.

The compounds of the invention of the general formula (I) or, where appropriate, suitable salts of these compounds can be used to manufacture pharmaceutical compositions for oral, sublingual, buccal, subcutaneous, intramuscular, intravenous, topical, intratracheal, intranasal, transdermal, vaginal or rectal administration and be administered to animals or humans in unit dose forms mixed with conventional pharmaceutical carriers for the prophylaxis or treatment of the above disorders or diseases.

Suitable uniform administration forms (unit dose forms) comprise forms for oral administration, such as tablets, gelatin capsules, powders, granules, solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

In order to achieve the desired prophylactic or therapeutic effect, the dose of the active compound can vary between 0.01 and 50 mg per kg of body weight and per day.

Each unit dose may comprise from 0.05 to 5000 mg, preferably 1 to 1000 mg, of the active compound in combination with a pharmaceutical carrier. This unit dose can be administered 1 to 5 times a day so that a daily dose of from 0.5 to 25 000 mg, preferably 1 to 5000 mg, is administered.

If a solid composition in the form of tablets is prepared, the active compound is mixed with a pharmaceutical carrier such as gelatin, starch, lactose, magnesium stearate, talc, silicon dioxide or the like.

The tablets can be coated with sucrose, a cellulose derivative or another suitable substance or be treated otherwise in order to display a prolonged or delayed activity and in order to release a predetermined amount of the active compound continuously.

A preparation in the form of gelatin capsules is obtained by mixing the active compound with an extender and taking up the resulting mixture in soft or hard gelatin capsules.

A preparation in the form of a syrup or elixir or for administration in the form of drops may comprise active compounds together with a sweetener which is preferably calorie-free, methylparaben or propylparaben as antiseptics, a flavouring and a suitable colouring.

The water-dispersible powders or granules may comprise the active compounds mixed with dispersants, wetting agents or suspending agents, such as polyvinylpyrrolidones, and sweeteners or taste improvers.

Rectal or vaginal administration is achieved by the use of suppositories which are prepared with binders which melt at the rectal temperature, for example cocoa butter or polyethylene glycols. Parenteral administration is effected by using aqueous suspensions, isotonic salt solutions or sterile and injectable solutions which comprise pharmacologically suitable dispersants and/or wetting agents, for example propylene glycol or polyethylene glycol.

The active compound can also be formulated as microcapsules or centrosomes, if suitable with one or more carriers or additives.

In addition to the compounds of the general formula (I), or their pharmaceutically acceptable salts or prodrugs, the compositions of the invention may comprise further active compounds which may be beneficial for the treatment of the impairments or disorders indicated above.

The present invention therefore further relates to pharmaceutical compositions which comprise a plurality of active compounds, where at least one of these is a compound (I) according to the invention, a tautomer, a salt or a prodrug thereof.

Preparation of the Compounds of the Invention

Examples of synthetic routes for preparing the oxindole derivatives of the invention are described below.

The preparation of the oxindoles according to the invention can be carried out by different routes as illustrated in synthesis schemes 1 and 2. In these synthesis schemes, the variables have the same meanings as in the general formula (I).

The 3-hydroxy-1,3-dihydroindol-2-ones IV can be obtained by adding metallated heterocycles III to the 3-keto group of the isatins II. The metallated heterocycles, such as, for example, the corresponding Grignard (Mg) or organyl-lithium compound, can be obtained in a customary manner from halogen or hydrocarbon compounds. Exemplary procedures can be found in Houben-Weyl, Methoden der Organischen Chemie [Methods of organic chemistry], Vol. 13, 1-2, Chap. Mg and Li compounds. The isatins II are either commercially available or were prepared in analogy to methods described in the literature (Advances in Heterocyclic Chemistry, A. R. Katritzky and A. J. Boulton, Academic Press, New York, 1975, 18, 2-58; J. Brazil. Chem. Soc. 12, 273-324, 2001).

Using KCN or $Zn(CN)_2$ with Pd(0) catalysis in solvents such as dimethylformamide or tetrahydrofuran, if appropriate also with addition of bases such as $K_2CO_3$ or other carbonates and amines, it is possible to convert, at elevated temperature, the 3-hydroxyoxindoles IV which, in the 6-membered aromatic ring contain, for example as radical $R^3$ or $R^4$, an iodine substituent, into the analogous cyano-containing 3-hydroxy-oxindoles IV. Suitable for use as Pd(0) salts are, for example, transition metal complexes prepared in situ from $PdCl_2$ or $PdOAc_2$ by addition of phosphines, such as tris(orthotolyl) phosphine. It is also possible to use commercial palladium complexes, such as, for example, the catalyst tetrakis(triphenylphosphine)palladium(0) and/or added phosphine ligands.

The 3-hydroxyoxindoles IV can be converted into the compounds V which carry a leaving group LG' in position 3, where the leaving group LG' may be a customary leaving group, such as, for example, halide, mesylate or tosylate. The intermediate V where, for example, LG'=chlorine, can be prepared by treating the alcohol IV with thionyl chloride in the presence of a base, such as, for example, pyridine. Alternatively, it is possible to obtain alcohols IV by conversion into the mesylate using methanesulphonyl chloride in the presence of a base, such as, for example, triethylamine. The compounds V are subsequently reacted with amines, such as, for example, ammonia, which gives the analogous amines VI after the substitution reactions. Compounds such as VI can then, after deprotonation with a strong base, such as, for example, potassium tert-butoxide or sodium hydride, in DMF, be converted into the product VIII by treatment with sulphonyl chlorides VII. The sulphonyl chlorides VII used are either commercially available or can be prepared in a manner analogous to known processes (see, for example, J. Med. Chem. 40, 1149 (1997)).

The compounds VIII are converted into compounds IX by reaction with reagents for derivatizing amino groups, such as, for example chloroformates, isocyanates or carbamoyl chlorides, generally using customary methods (see J. March, Advanced Organic Chemistry, 1992, 4th edition., Wiley, New York, pages 417-421; 499; 903). For example, LG as leaving group may be OPhenyl in the compound IX, which is obtained by reacting VIII with phenyl chloroformate in the presence of a base, such as, for example, pyridine.

The subsequent reaction with amines X, if appropriate at elevated temperature and with addition of auxiliary bases, such as, for example, triethylamine or diisopropylethylamine, gives the compounds according to the invention of the general formula (I). The amines X are either commercially available or can be prepared by methods known from the literature.

A further alternative of preparing the amine X is the reaction of amines with aldehydes or ketones in the presence of reducing agents, such as, for example, sodium cyanoborohydride or sodium acetoxyborohydride, in the sense of a reductive amination (J. March, Advanced Organic Chemistry, 1992, 4th edition., Wiley, New York, pages 411; 898).

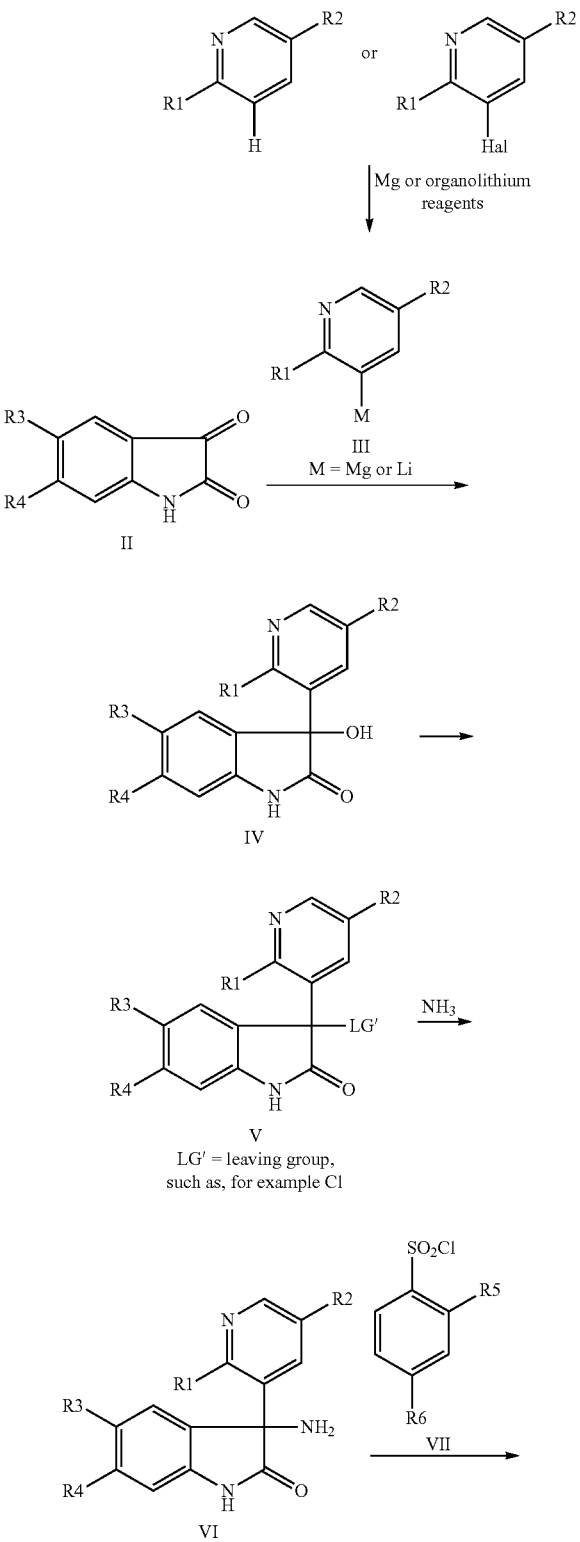

SYNTHESIS SCHEME 1

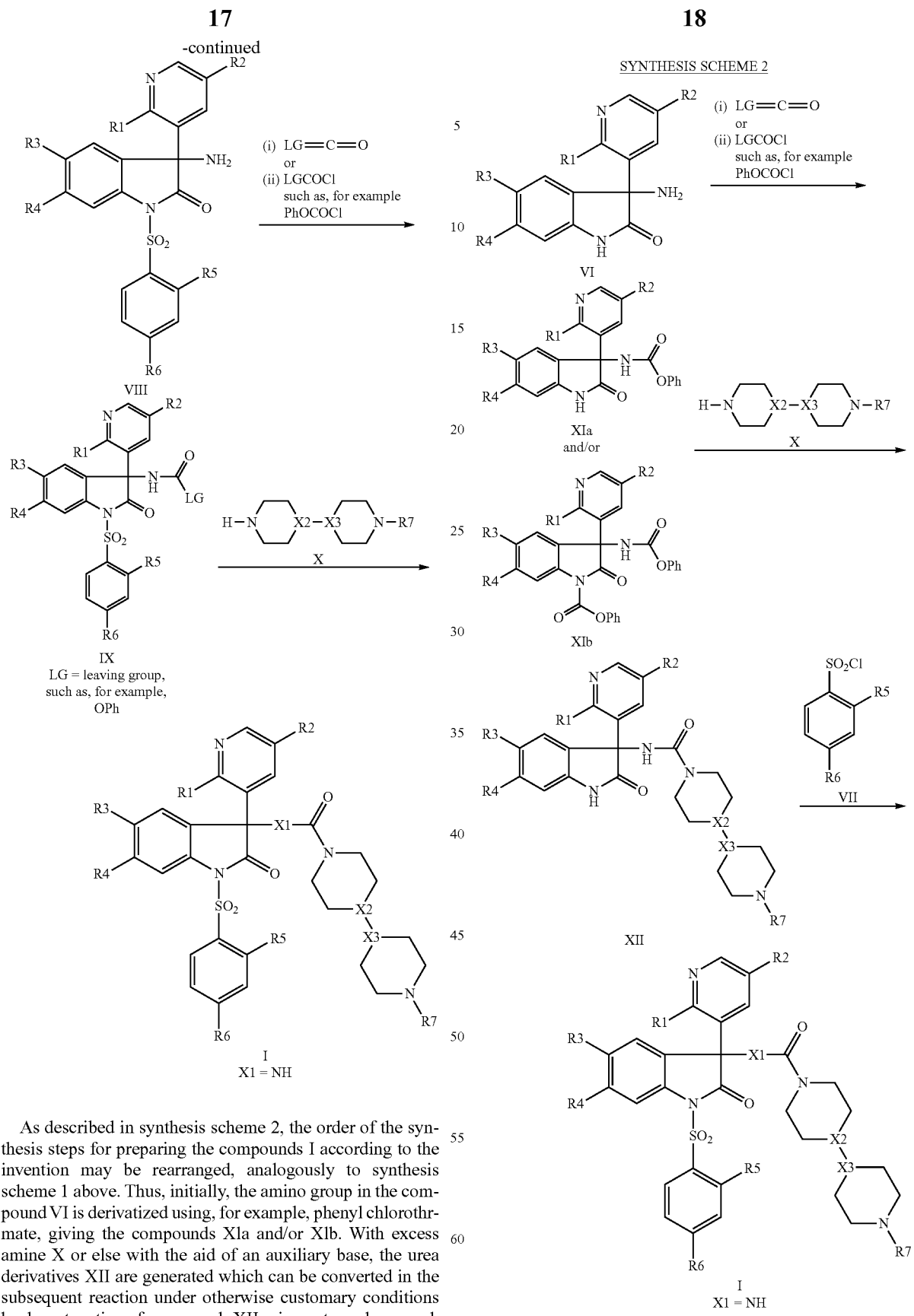

As described in synthesis scheme 2, the order of the synthesis steps for preparing the compounds I according to the invention may be rearranged, analogously to synthesis scheme 1 above. Thus, initially, the amino group in the compound VI is derivatized using, for example, phenyl chlorothrmate, giving the compounds XIa and/or XIb. With excess amine X or else with the aid of an auxiliary base, the urea derivatives XII are generated which can be converted in the subsequent reaction under otherwise customary conditions by deprotonation of compounds XII using a strong base, such as, for example, sodium hydride or potassium tert-butoxide, and subsequent treatment with sulphonyl chlorides VII in DMF into the compounds I according to the invention.

Below, the invention is illustrated in more detail using examples, the examples not being intended to be limiting.

The compounds according to the invention can be prepared via various synthesis routes. The procedures mentioned, as described accordingly in synthesis schemes 1 and 2, are only described in greater detail by way of example on the basis of the examples mentioned, without being exclusively limited to the synthesis routes 1 or 2 or analogous procedures mentioned.

EXPERIMENTAL PART

Example 1

N-[5-Cyano-1-[(2,4-dimethoxyphenyl)sulphonyl]-3-(2-ethoxypyridin-3-yl)-2-oxo-2,3-dihydro-1H-indol-3-yl]-4-(1-methylpiperidin-4-yl)piperazine-1-carboxamide 1a) 3-(2-Ethoxypyridin-3-yl)-3-hydroxy-5-iodo-1,3-dihydro-2H-indol-2-one With ice-bath cooling, 20.86 g (76.40 mmol) of 5-iodoisatin were stirred in 400 ml of anhydrous tetrahydrofuran (THF), and 3.22 g (80.50 mmol, 60% w/w) of sodium hydride were added a little at a time, the temperature being kept between 0-10° C. With ice-bath cooling, the suspension was stirred for one hour, during which the pyridine Grignard reagent was prepared. At room temperature, 20 g (80.30 mmol) of the 2-ethoxy-3-iodopyridine were dissolved in 400 ml of anhydrous THF, and over a period of 5-10 minutes 95.6 ml (1M solution in THF, 95.60 mmol) of ethylmagnesium bromide were added to this solution with cooling, at a temperature between 22 and 15° C. The solution was stirred for 20 minutes, during which time the colour changed from colourless to slightly yellowish.

The solution of the pyridine Grignard reagents was then, over a period of 5-10 minutes, added to the solution, cooled in an ice-bath, of the 5-iodoisatin sodium salt, the temperature fluctuating between 5 and 18° C. After the addition of the Grignard reagent had ended, the ice-bath was removed, and the reaction mixture was stirred at room temperature for another 2 hours. Excess saturated ammonium chloride solution was added, followed by ethyl acetate, and the mixture was stirred for another 5 minutes. The aqueous phase was removed and extracted with ethyl acetate (2×). The combined organic phases were washed with water (2×), and the solvent was removed under reduced pressure. Initially, unreacted 5-iodoisatin precipitated from the still dilute solution and was removed, and after further concentration the product, too, crystallized out. The suspension was stored in a refrigerator at 5° C. for two hours and the slightly yellowish solid was then filtered off and washed with a little ethyl acetate. The desired 3-(2-ethoxypyridin-3-yl)-3-hydroxy-5-iodo-1,3-dihydro-2H-indol-2-one (17.1 g, 43.16 mmol, 57%) was isolated after drying at 40° C.

ESI-MS [M+H$^+$]=397.05 calculated for $C_{15}H_{13}IN_2O_3$=396.19

1b) 5-Cyano-3-hydroxy-3-(2-ethoxypyridin-3-yl)-1,3-dihydroindol-2-one

Under an atmosphere of nitrogen, 7.1 g (17.92 mmol) of 3-(2-ethoxypyridin-3-yl)-3-hydroxy-5-iodo-1,3-dihydro-2H-indol-2-one were stirred in 100 ml of anhydrous THF at room temperature. 2.1 g (17.92 mmol) of zinc cyanide were added, followed by 0.51 g (0.45 mmol) of tetrakis(triphenylphosphine)palladium(0). The reaction mixture was transferred directly into a preheated oil bath at a temperature of 100° C. The mixture was stirred at 100° C. (oil bath temperature), and after 30 minutes, another 0.51 g (0.45 mmol) of the catalyst was added. In total, the mixture was stirred for 2 hours. The reaction mixture was cooled to room temperature, and an excess of water was added. The mixture was extracted with ethyl acetate (3×), and the combined organic phases were washed with water (3×). The solvent was evaporated to dryness under reduced pressure, and the residue was slurried with small volumes of ethyl acetate. A slightly yellowish solid was removed by filtration, washed with ethyl acetate and dried in a vacuum drying cabinet. It was possible to isolate 3.7 g (12.44 mmol, 69.4%) of the desired product 5-cyano-3-hydroxy-3-(2-ethoxypyridin-3-yl)-1,3-dihydroindol-2-one.

ESI-MS [M+H$^+$]=296.05 calculated for $C_{16}H_{13}N_3O_3$=295.30

1c) 3-Chloro-3-(2-ethoxypyridin-3-yl)-2-oxoindoline-5-carbonitrile

Under an atmosphere of nitrogen, 6.00 g (20.32 mmol) of the 5-cyano-3-hydroxy-3-(2-ethoxypyridin-3-yl)-1,3-dihydroindol-2-one were suspended in 60 ml of anhydrous dichloromethane (dried over molecular sieve). 2.30 ml (28.45 mmol) of pyridine were then added. The reaction mixture was cooled to a temperature of 0° C., and 2.06 ml (28.45 mmol) of neat thionyl chloride were then added dropwise (exothermic reaction). The mixture was stirred at room temperature for one hour. The formation of a yellow suspension was observed. The course of the reaction was monitored by thin-layer chromatography (TLC) (silica gel, dichloromethane/methanol in a ratio of 95:5). The reaction mixture was carefully poured into ice-water. After 15 minutes of stirring, the organic phase was removed. The aqueous phase was extracted with dichloromethane (2×). All organic phases were combined, dried over magnesium sulphate and filtered, and the solvent was removed under reduced pressure. The product gave 5.70 g (18.17 mmol, 89%) of 3-chloro-3-(2-ethoxypyridin-3-yl)-2-oxoindoline-5-carbonitrile as an amorphous solid which was used without further purification for the next reaction. ESI-MS [M+H$^+$]=314.1 calculated for $C_{16}H_{12}ClN_3O_2$=313.75

1d) 3-Amino-3-(2-ethoxypyridin-3-yl)-2-oxoindoline-5-carbonitrile 5.70 g (18.17 mmol) of 3-chloro-3-(2-ethoxypyridin-3-yl)-2-oxoindoline-5-carbonitrile were dissolved in 50 ml of dichloromethane. Under an atmosphere of nitrogen, 14 ml (98.11 mmol) of a 7 N methanolic ammonia solution were slowly added dropwise to the cooled reaction solution. The colour of the solution changed to light-yellow, and the solution was stirred at room temperature overnight, during which time the product slowly crystallized out. The course of the reaction was monitored by TLC (silica gel, dichloromethane/methanol in a ratio of 9:1). The solvent was removed under reduced pressure, and the residue was once more taken up and dissolved in dichloromethane. The mixture was then extracted with water. The phases were separated, and a greasy phase which had formed between the phases was added to the aqueous phase. The aqueous phase was extracted with ethyl acetate until the greasy phase had gone into solution. All organic phases obtained were combined, and the solvent was removed under reduced pressure. The residue was triturated with diethyl ether, resulting in the formation of a solid substance which was filtered off and dried in a vacuum drying cabinet at moderate temperature (35° C.). This gave 4.54 g (15.43 mmol, 85%) of the 3-amino-3-(2-ethoxypyridin-3-yl)-2-oxoindoline-5-carbonitrile as a solid.
ESI-MS [M+H⁺]=295.3 calculated for $C_{16}H_{14}N_4O_2$=294.32

1e) 3-Amino-1-[(2,4-dimethoxyphenyl)sulphonyl]-3-(2-ethoxypyridin-3-yl)-2-oxoindoline-5-carbonitrile 3.54 g (12.03 mmol) of 3-amino-3-(2-ethoxypyridin-3-yl)-2-oxoindoline-5-carbonitrile were dissolved in 80 ml of anhydrous dimethylformamide (dried over molecular sieve). Under an atmosphere of nitrogen and with cooling using an ice-bath, 1.49 g (13.23 mmol) of potassium tert-butoxide were added a little at a time. The colour of the reaction mixture changed, and the brown solution was stirred at 0° C. for another hour to ensure that the deprotonation proceeded to completion. At low temperature, 3.16 g (13.23 mmol) 2,4-dimethoxybenzenesulphonyl chloride were added, and the mixture was stirred at 0° C. for another two hours. The course of the reaction was monitored by TLC (silica gel, dichloromethane/methanol in a ratio of 9:1). The reaction mixture was poured into ice-water and then extracted with ethyl acetate. The organic phase was washed with saturated sodium chloride solution and dried over magnesium sulphate, and the solvent was evaporated. The residue was suspended in diethyl ether and stirred until the product precipitated as a solid and could be removed by filtration. After removal of the solvent, the mother liquor was once more treated with diethyl ether (2×) until finally, after drying, 4.67 g (9.44 mmol, 79%) of the desired 3-amino-1-[(2,4-dimethoxyphenyl)sulphonyl]-3-(2-ethoxypyridin-3-yl)-2-oxoindoline-5-carbonitrile were obtained as a solid substance.
ESI-MS [M+H⁺]=495.15 calculated for $C_{24}H_{22}N_4O_6S$=494.53

1f) Phenyl [5-cyano-1-[(2,4-dimethoxyphenyl)sulphonyl]-3-(2-ethoxypyridin-3-yl)-2-oxo-2,3-dihydro-1H-indol-3-yl]carbamate 4.67 g (9.44 mmol) of 3-amino-1-[(2,4-dimethoxyphenyl)sulphonyl]-3-(2-ethoxypyridin-3-yl)-2-oxoindoline-5-carbonitrile were dissolved in 120 ml of pyridine and cooled to 0° C. using an ice-bath. 1.30 ml (10.39 mmol) of neat phenyl chloroformate were added, and the reaction mixture was stirred at 0° C. for 2 hours. The course of the reaction was monitored by TLC (silica gel, dichloromethane/methanol in a ratio of 95:5). The solvent and especially pyridine were removed under reduced pressure, and the residue was diluted with water and extracted with ethyl acetate (3×). The combined organic phases were washed with saturated sodium chloride solution, dried over magnesium sulphate and filtered, and the solvent was removed under reduced pressure. Traces of pyridine were removed by repeated addition of toluene and evaporation on a rotary evaporator. Diethyl ether was added to the isolated residue, and a solid crystallized overnight giving 5.62 g (9.14 mmol, 97%) of the desired product phenyl [5-cyano-1-[(2,4-dimethoxyphenyl)sulphonyl]-3-(2-ethoxypyridin-3-yl)-2-oxo-2,3-dihydro-1H-indole-3-yl]carbamate.
ESI-MS [M+H⁺]=615.15 calculated for $C_{31}H_{26}N_4O_8S$=614.64

1g) N-[5-Cyano-1-[(2,4-dimethoxyphenyl)sulphonyl]-3-(2-ethoxypyridin-3-yl)-2-oxo-2,3-dihydro-1H-indol-3-yl]-4-(1-methylpiperidin-4-yl)piperazine-1-carboxamide 1.00 g (1.63 mmol) of phenyl [5-cyano-1-[(2,4-dimethoxyphenyl)sulphonyl]-3-(2-ethoxypyridin-3-yl)-2-oxo-2,3-dihydro-1H-indol-3-yl]carbamate, 596 mg (3.25 mmol) of 1-(1-methylpiperidin-4-yl)piperazine and 8 ml of dried THF were combined and the mixture was stirred at room temperature for 24 hours. The end of the reaction was detected with the aid of analytical HPLC (RP, eluents acetonitrile/water, 0.01% TFA). The solvent was removed, and the residue was purified by preparative HPLC using dichloromethane and 6% methanol as eluents on a Chromolith column (normal phase, from Merck). After repeated column chromatography, it was possible to isolate 230 mg (0.33 mmol, 21%) of the N-[5-cyano-1-[(2,4-dimethoxyphenyl)sulphonyl]-3-(2-ethoxypyridin-3-yl)-2-oxo-2,3-dihydro-1H-indol-3-yl]-4-(1-methylpiperidin-4-yl)piperazine-1-carboxamide. Alternatively, work-up and purification after the reaction had ended could be carried out as follows: the solvent was removed. The crude material was dissolved in ethyl acetate and extracted with 1 N HCl. The impurities were detected in the organic phase, the product being in the acidic aqueous phase. Accordingly, the aqueous phase was neutralized with 2 N NaOH solution and extracted with ethyl acetate. After drying over magnesium sulphate, filtration and removal of the ethyl acetate under reduced pressure, the product could be crystallized with diethyl ether. The N-[5-cyano-1-[(2,4-dimethoxyphenyl)sulphonyl]-3-(2-ethoxypyridin-3-yl)-2-oxo-2,3-dihydro-1H-indol-3-yl]-4-(1-methylpiperidin-4-yl)piperazine-1-carboxamide was obtained in yields of >50%.
ESI-MS [M+H⁺]=704.2 calculated for $C_{35}H_{41}N_7O_7S$=703.82
¹H-NMR ([D6]-DMSO, 400 MHz) δ [ppm]=8.12 (d, 1H, J=4.8 Hz), 7.88 (d, 1H, J=8.8 Hz), 7.87 (d, 1H, J=8.7 Hz), 7.81 (d, 1H, J=8.5 Hz), 7.72 (d, 1H, J=7.6 Hz), 7.67 (s, 1H), 7.64 (s, 1H), 7.02 (dd, 1H, J=5.0 Hz, J=7.5 Hz), 6.69 (d, 1H, J=8.9 Hz), 6.65 (s, 1H), 4.15 (m, 2H), 3.85 (s, 3H), 3.44 (s, 3H), 3.20 (m, 4H), 2.76 (m, 2H, J=11.1 Hz), 2.34 (m, 4H), 2.11 (m, 4H), 1.81 (m, 2H, J=11.3 Hz), 1.64 (m, 2H, J=10.7 Hz), 1.37 (m, 2H), 1.06 (t, 1H, J=7.0 Hz).

Example 5

N-[5-Cyano-3-(2-ethoxypyridin-3-yl)-1-[(4-methoxyphenyl)sulphonyl]-2-oxo-2,3-dihydro-1H-indol-3-yl]-4-(1-methylpiperidin-4-yl)piperazine-1-carboxamide 5a) Phenyl 5-cyano-3-(2-ethoxypyridin-3-yl)-2-oxo-3-[(phenoxycarbonyl)amino]indoline-2-carboxylate 2.78 g (9.43 mmol) of 3-amino-3-(2-ethoxypyridin-3-yl)-2-oxoindoline-5-carbonitrile (prepared according to Example 1, process steps 1a) to 1c)) were suspended in 25 ml of dichloromethane and cooled with an ice-bath to 0° C. 7.63 ml (94.34 mmol) of pyridine were added, and 2.37 ml (18.87 mmol) of phenyl chloroformate were then added slowly dropwise such that the temperature did not exceed 5-10° C. With thawing of the ice-bath, the reaction was stirred at room temperature overnight, and a lightly coloured solid precipitated out. The reaction mixture was diluted with dichloromethane, and after addition of water, the solid went back into solution. The phases were separated and the aqueous phase was again extracted with dichloromethane (1×). The combined organic phases were washed initially with water (3×) and then with saturated sodium chloride solution (1×). After drying over magnesium sulphate, filtration and evaporation of the solvent under reduced pressure, the residue was subjected to incipient dissolution in diethyl ether, and 10 times the amount of pentane was added. A white precipitate formed, and this was filtered off with suction, washed with pentane and dried in a vacuum drying cabinet at 40° C. After fractional crystallization, a total of 4.46 g (8.35 mmol, 89%) of phenyl 5-cyano-3-(2-ethoxypyridin-3-yl)-2-oxo-3-[(phenyloxycarbonyl)amino]indoline-1-carboxylate were isolated.

ESI-MS [M+H$^+$]=535.15 calculated for $C_{30}H_{22}N_4O_6$=534.53

5b) N-[5-Cyano-3-(2-ethoxypyridin-3-yl)-2-oxo-2,3-dihydro-1H-indol-3-yl]-4-(1-methylpiperidin-4-yl)piperazine-1-carboxamide 760 mg (1.42 mmol) of phenyl 5-cyano-3-(2-ethoxypyridin-3-yl)-2-oxo-3-[(phenoxy-carbonyl)amino]indoline-1-carboxylate were initially charged in 5 ml of THF, and 1.42 g (5.69 mmol) of 1-(1-methylpiperidin-4-yl)piperazine were added undiluted at room temperature. The reaction mixture was stirred overnight, and the reaction was checked by TLC (silica gel, dichloromethane/methanol 15:5) to determine the progress of the reaction. The reaction was diluted with ethyl acetate and washed with water (1×) and saturated sodium chloride solution (1×). The organic phase was dried over magnesium sulphate and filtered, and the solvent was removed under reduced pressure. The residue was taken up in a little diethyl ether, and 6 times the amount of cyclohexane was added. A colourless solid comprising 615 mg (1.22 mmol, 86%) of pure N-[5-cyano-3-(2-ethoxypyridin-3-yl)-2-oxo-2,3-dihydro-1H-indo I-3-yl]-4-(1-methylpiperidin-4-yl)piperazine-1-carboxamide precipitated out.

ESI-MS [M+H$^+$]=504.25 calculated for $C_{27}H_{33}N_7O_3$=503.61

5c) N-[5-Cyano-3-(2-ethoxypyridin-3-yl)-1-[(4-methoxyphenyl)sulphonyl]-2-oxo-2,3-dihydro-1H-indol-3-yl]-4-(1-methylpiperidin-4-yl)piperazine-1-carboxamide 80.0 mg (0.16 mmol) of N-[5-cyano-3-(2-ethoxypyridin-3-yl)-2-oxo-2,3-dihydro-1H-indol-3-yl]-4-(1-methylpiperidin-4-yl)piperazine-1-carboxamide were dissolved in dimethylformamide, and 7.63 mg (0.19 mmol, 60% w/w) of sodium hydride were added at 0° C. For the deprotonation of the 1,3-dihydro-2H-indol-2-on derivative, the mixture was stirred for 10 minutes, and 39.4 mg (0.19 mmol) of 4-methoxybenzenesulphonyl chloride were then added. The mixture was then allowed to warm to room temperature and stirred for 30 minutes. The progress of the reaction was monitored by TLC (silica gel, dichloromethane/methanol 1:1). Saturated sodium bicarbonate solution and ethyl acetate were added to the reaction mixture, and the phases were then separated. The aqueous phase was reextracted with ethyl acetate (1×). The combined organic phase was washed with water (1×) and saturated sodium chloride solution (1×), dried over magnesium sulphate and filtered, and the solvent was removed under reduced pressure. The residue was purified by preparative MPLC (ISCO Companion, 4 g NP cartridge) using the mobile phases dichloromethane/methanol (5-20%). What was isolated were 27.3 mg (0.04 mmol, 23% yield, 90% purity) of N-[5-cyano-3-(2-ethoxypyridin-3-yl)-1-[(4-methoxyphenyl)sulphonyl]-2-oxo-2,3-dihydro-1H-indol-3-yl]-4-(1-methylpiperidin-4-yl)piperazine-1-carboxamide.

ESI-MS [M+H$^+$]=674.2 calculated for $C_{34}H_{39}N_7O_6S$=673.80

Alternative purification methods to the crystallization of the crude mixtures include the conventional column chromatography on a normal phase (NP-SiO$_2$ cartridge, Chromabond) using the mobile phases dichloromethane/methanol and the preparative HPLC (RP, mobile phase acetonitrile/water, 0.01% TFA or 0.01% acetic acid).

Examples 2 to 4 and 6 to 30

The compounds according to Examples 2 to 4 and 6 to 30 can be prepared in a manner analogous to the preparation procedures according to Example 1 and/or Example 5 using the appropriate starting materials.

Example 2

N-{5-Cyano-3-(2-ethoxypyridin-3-yl)-1-[(2-methoxyphenyl)sulphonyl]-2-oxo-2,3-dihydro-1H-indol-3-yl}-4-(1-methylpiperidin-4-yl)piperazine-1-carboxamide ESI-MS [M+H$^+$]=674.05 calculated for $C_{34}H_{39}N_7O_6S$=673.80

Example 3

N-[5-Cyano-1-[(2-ethoxyphenyl)sulphonyl]-3-(2-ethoxypyridin-3-yl)-2-oxo-2,3-dihydro-1H-indol-3-yl]-4-(1-methylpiperidin-4-yl)piperazine-1-carboxamide trifluoroacetate ESI-MS=688.3 calculated for $C_{35}H_{41}N_7O_6S$=687.82

Example 4

N-[5-Cyano-3-(2-ethoxypyridin-3-yl)-2-oxo-1-(phenylsulphonyl)-2,3-dihydro-1H-indol-3-yl]-4-(1-methylpiperidin-4-yl)piperazine-1-carboxamide ESI-MS [M+H$^+$]=644.2 calculated for $C_{33}H_{37}N_7O_5S$=643.77

Example 31

N-[5-Cyano-1-[(2,4-dimethoxyphenyl)sulphonyl]-3-(2-ethoxypyridin-3-yl)-2-oxo-2,3-dihydro-1H-indol-3-yl]-4-(4-methylpiperazin-1-yl)piperidine-1-carboxamide 100 mg (0.16 mmol) of the phenyl [5-cyano-1-[(2,4-dimethoxyphenyl)sulphonyl]-3-(2-ethoxypyridin-3-yl)-2-oxo-2,3-dihydro-1H-indol-3-yl]carbamate (prepared according to Example 1, process steps 1a) to 1f)) were initially charged in 8 ml of anhydrous tetrahydrofuran (dried over molecular sieve), and 44.7 mg (0.24 mmol) of 1-methyl-4-(piperidin-4-yl)piperazine were added. The reaction mixture was stirred at room temperature overnight. The course of the reaction was monitored by TLC (silica gel, dichloromethane/methanol in a ratio of 9:1) and LCMS (RP, acetonitrile/water as eluents and 0.01% TFA). The solvent was removed under reduced pressure, and the residue was taken up in dichloromethane and extracted with 2 N sodium hydroxide solution (1×). The combined organic phases were dried over magnesium sulphate and filtered, and the solvent was removed under reduced pressure. The crude mixture was purified twice by column chromatography (5 g NP-SiO$_2$ cartridge Chromabond) using dichloro-methane/methanol in a ratio of 99:1 to 80:20 as eluent. What was isolated were 53.8 mg (0.08 mmol, 47%) of pure N-[5-cyano-1-[(2,4-dimethoxyphenyl)sulphonyl]-3-(2-ethoxypyridin-3-yl)-2-oxo-2,3-dihydro-1H-indol-3-yl]-4-(4-methylpiperazin-1-yl)piperidine-1-carboxamide.

ESI-MS [M+H$^+$]=704.25 calculated for C$_{35}$H$_{47}$N$_7$O$_7$S=703.82

$^1$H-NMR ([D6]-DMSO, 400 MHz) δ [ppm]=8.13 (dd, 1H, J=1.4 Hz, J=4.8 Hz), 7.88 (d, 1H, J=8.5 Hz), 7.87 (d, 1H, J=8.8 Hz), 7.81 (dd, 1H, J=1.6 Hz, J=8.6 Hz), 7.71 (dd, 1H, J=1.4 Hz, J=7.6 Hz), 7.68 (d, 1H, J=1.3 Hz), 7.65 (s, 1H), 7.02 (dd, 1H, J=4.9 Hz, J=7.6 Hz), 6.68 (d, 1H, J=8.9 Hz), 6.65 (s, 1H), 4.17 (m, 2H), 3.85 (s, 3H), 3.80 (m, 2H), 3.44 (s, 3H), 2.62 (m, 2H), 2.41-2.12 (m, 9H), 2.12 (s, 3H), 1.61 (m, 2H), 1.16 (m, 2H), 1.09 (t, 3H, J=7.0 Hz).

Examples 32 to 36

The compounds according to Examples 32 to 36 can be prepared in a manner analogous to the preparation procedures according to Example 1, 5 and/or 31 using the appropriate starting materials.

Example 32

N-[5-Cyano-3-(2-ethoxypyridin-3-yl)-1-[(2-methoxyphenyl)sulphonyl]-2-oxo-2,3-dihydro-1H-indol-3-yl]-4-(4-methylpiperazin-1-yl)piperidine-1-carboxamide ESI-MS [M+H$^+$]=674.8 calculated for C$_{34}$H$_{39}$N$_7$O$_6$S=673.80

Example 33

N-[5-Cyano-1-[(2-ethoxyphenyl)sulphonyl]-3-(2-ethoxypyridin-3-yl)-2-oxo-2,3-dihydro-1H-indol-3-yl]-4-(4-methylpiperazin-1-yl)piperidine-1-carboxamide trifluoroacetate ESI-MS [M+H$^+$]=688.2 calculated for C$_{35}$H$_{41}$N$_7$O$_6$S=687.82

Example 34

N-[5-Cyano-3-(2-ethoxypyridin-3-yl)-2-oxo-1-(phenylsulphonyl)-2,3-dihydro-1H-indol-3-yl]-4-(4-methylpiperazin-1-yl)piperidine-1-carboxamide ESI-MS [M+H$^+$]=644.7 calculated for C$_{33}$H$_{37}$N$_7$O$_5$S=643.77

Example 35

N-[5-Cyano-3-(2-ethoxypyridin-3-yl)-1-[(4-methoxyphenyl)sulphonyl]-2-oxo-2,3-dihydro-1H-indol-3-yl]-4-(4-methylpiperazin-1-yl)piperidine-1-carboxamide trifluoroacetate ESI-MS [M+H$^+$]=674.2 calculated for C$_{34}$H$_{39}$N$_7$O$_6$S=673.80

Example 37

N-[5-Cyano-1-[(2,4-dimethoxyphenyl)sulphonyl]-3-(2-ethoxypyridin-3-yl)-2-oxo-2,3-dihydro-1H-indol-3-yl]-4-(4-ethylpiperazin-1-yl)piperidine-1-carboxamide 100 mg (0.16 mmol) of the phenyl [5-cyano-1-[(2,4-dimethoxyphenyl)sulphonyl]-3-(2-ethoxypyridin-3-yl)-2-oxo-2,3-dihydro-1H-indol-3-yl]carbamate (prepared according to Example 1, process steps 1a) to 1f)), dissolved in 8 ml of anhydrous tetrahydrofuran (dried over molecular sieve) were initially charged. 74.9 mg (0.24 mmol) of 1-ethyl-4-piperidin-4-ylpiperazine and 0.07 ml of triethylamine were added together to the reaction mixture, which was then stirred at room temperature overnight. To accelerate the reaction and to achieve complete conversion, the mixture was again heated to 50° C. The course of the reaction was monitored by TLC (silica gel, dichloromethane/methanol in a ratio of 9:1) and LCMS (RP, acetonitrile/water as eluents and 0.01% TFA). The solvent was removed under reduced pressure, and the residue was taken up in dichloromethane and extracted with 2 N sodium hydroxide solution (1×). The combined organic phases were dried over magnesium sulphate and filtered, and the solvent was removed under reduced pressure. The crude mixture was purified initially by column chromatography of silica gel (column 20×200 mm) using dichloromethane and 2% methanol as eluents. The combined, still slightly contaminated product fractions were purified again by preparative HPLC on a Chromolith column (normal phase, from Merck) using the eluents dichloromethane and methanol (gradient 0-10% by volume of methanol over 15 min.). This gave 20 mg (0.03 mmol, 17%) of the desired N-[5-cyano-1-[(2,4-dimethoxyphenyl)sulphonyl]-3-(2-ethoxypyridin-3-yl)-2-oxo-2,3-dihydro-1H-indol-3-yl]-4-(4-ethylpiperazin-1-yl)piperidine-1-carboxamide.

ESI-MS [M+H$^+$]=718.25 calculated for C$_{36}$H$_{43}$N$_7$O$_7$S=717.85

$^1$H-NMR ([D6]-DMSO, 400 MHz) δ [ppm]=8.13 (dd, 1H, J=1.2 Hz, J=4.6 Hz), 7.88 (d, 1H, J=8.2 Hz), 7.87 (d, 1H, J=8.7 Hz), 7.81 (dd, 1H, J=1.4 Hz, J=8.6 Hz), 7.72 (dd, 1H, J=1.3 Hz, J=7.6 Hz), 7.68 (d, 1H, J=1.1 Hz), 7.66 (s, 1H), 7.02 (dd, 1H, J=4.9 Hz, J=7.6 Hz), 6.68 (dd, 1H, J=2.0 Hz, J=8.8 Hz), 6.65 (d, 1H, J=2.2 Hz), 4.17 (m, 2H), 3.85 (s, 3H), 3.81 (m, 2H), 3.44 (s, 3H), 2.62 (m, 2H), 2.43-2.29 (m, 11H), 1.61 (m, 2H), 1.15 (m, 2H), 1.09 (t, 3H, J=7.0 Hz), 0.97 (t, 3H, J=7.1 Hz).

Examples 38 to 90

The compounds according to Examples 38 to 90 can be prepared in a manner analogous to the preparation procedures according to Examples 1, 5, 31, 37, 55, 61 and/or 67 using the appropriate starting materials.

Example 40

N-[5-Cyano-3-(2-ethoxypyridin-3-yl)-2-oxo-1-(phenylsulphonyl)-2,3-dihydro-1H-indol-3-yl]-4-(4-ethylpiperazin-1-yl)piperidine-1-carboxamide ESI-MS [M+H$^+$]=658.25 calculated for C$_{34}$H$_{39}$N$_7$O$_5$S=657.79

Example 43

N-[5-Cyano-1-[(2,4-dimethoxyphenyl)sulphonyl]-3-(2-ethoxypyridin-3-yl)-2-oxo-2,3-dihydro-1H-indol-3-yl]-4-(4-propylpiperazin-1-yl)piperidine-1-carboxamide ESI-MS [M+H$^+$]=732.3 calculated for C$_{37}$H$_{45}$N$_7$O$_7$S=731.88

Example 55

N-[5-Cyano-1-[(2,4-dimethoxyphenyl)sulphonyl]-3-(2-ethoxypyridin-3-yl)-2-oxo-2,3-dihydro-1H-indol-3-yl]-4-piperazin-1-ylpiperidine-1-carboxamide

55a) tert-Butyl 4-[1-({[5-cyano-1-[(2,4-dimethoxyphenyl)sulphonyl]-3-(2-ethoxypyridin-3-yl)-2-oxo-2,3-dihydro-1H-indol-3-yl]amino}carbonyl)piperidin-4-yl]piperazine-1-carboxylate 100 mg (0.16 mmol) of phenyl [5-cyano-1-[(2,4-dimethoxyphenyl)sulphonyl]-3-(2-ethoxypyridin-3-yl)-2-oxo-2,3-dihydro-1H-indol-3-yl]carbamate (prepared according to Example 1, process steps 1a) to 1f)) were initially charged in 8 ml of anhydrous tetrahydrofuran (dried over molecular sieve), and 65.8 mg (0.24 mmol) of tert-butyl 4-piperidin-4-ylpiperazine-1-carboxylate were added. The mixture was then stirred at room temperature overnight. The progress of the reaction was monitored by TLC (silica gel, $CH_2Cl_2$/MeOH 9:1) and LCMS (RP, mobile phases acetonitrile/water and 0.01% TFA). The solvent was removed under reduced pressure, and the residue was taken up in dichloromethane and extracted with 2 N aqueous sodium hydroxide solution (1×). The combined organic phases were dried over magnesium sulphate and filtered, and the solvent was removed under reduced pressure. The crude mixture was purified by column chromatography (5 g NP-$SiO_2$ cartridge, Chromabond) using dichloromethane/methanol in a ratio of 98:2 as mobile phase. This gave 55.3 mg (0.07 mmol, 43%) of the desired product, which was directly used in the next reaction step for Boc deprotection.

ESI-MS [M+H$^+$]=790.30 calculated for $C_{39}H_{47}N_7O_9S$=789.91

55b) N-[5-Cyano-1-[(2,4-dimethoxyphenyl)sulphonyl]-3-(2-ethoxypyridin-3-yl)-2-oxo-2,3-dihydro-1H-indol-3-yl]-4-piperazin-1-ylpiperidine-1-carboxamide 55.3 mg (0.07 mmol) of tert-butyl 4-[1-({[5-cyano-1-[(2,4-dimethoxyphenyl)sulphonyl]-3-(2-ethoxypyridin-3-yl)-2-oxo-2,3,-dihydro-1H-indol-3-yl]amino}carbonyl)piperidin-4-yl]piperazine-1-carboxylate were initially charged in 4 ml of methanol, and 1.0 ml of 5-6 M hydrochloric acid in isopropanol was added. The mixture was stirred at room temperature. The progress of the reaction was monitored by TLC (silica gel, $CH_2Cl_2$/MeOH 9:1). After complete conversion, the alcoholic solvent residues were removed, and the residue was taken up in dichloromethane and, using 1 N aqueous sodium hydroxide solution, adjusted by extraction to pH 9. The organic phase was separated from the aqueous phase, and the aqueous phase was reextracted with dichloromethane (2×). The combined organic phase was dried over magnesium sulphate, and the solvent was removed under reduced pressure. The residue was crystallized from diethyl ether. Alternatively, the residue can also be purified either by conventional column chromatography on a normal phase (NP-$SiO_2$ cartridge, Chromabond) using dichloromethane/methanol as mobile phases or by preparative HPLC (RP, mobile phases acetonitrile/water, 0.01% TFA). After crystallization, 15.9 mg (0.023 mmol, 33%) of N-[5-cyano-1-[(2,4-dimethoxyphenyl)sulphonyl]-3-(2-ethoxypyridin-3-O-2-oxo-2,3-dihydro-1H-indol-3-yl]-4-piperazin-1-ylpiperidine-1-carbox amide were isolated.

ESI-MS [M+H$^+$]=690.45 calculated for $C_{34}H_{39}H_7O_7S$=689.80

Examples 25 to 30 and 56 to 60 and 85 to 90

The compounds according to Examples 25 to 30 and 56 to 60 and 85 to 90 can also be prepared in a manner analogous to the preparation procedures according to Examples 1, 5, 31, 37 and/or 55 using the appropriate starting materials.

Example 25

N-[5-Cyano-1-[(2,4-di methoxyphenyl)sulphonyl]-3-(2-ethoxypyridin-3-yl)-2-oxo-2,3-dihydro-1H-indol-3-yl]-4-piperidin-4-ylpiperazine-1-carboxamide bis (trifluoroacetate)

ESI-MS [M+H$^+$]=690.15 calculated for $C_{34}H_{39}N_7O_7S$=689.80

Example 85

N-[5-Cyano-1-[(2,4-dimethoxyphenyl)sulphonyl]-3-(2-ethoxypyridin-3-yl)-2-oxo-2,3-dihydro-1H-indol-3-yl]-4,4'-bipiperidine-1-carboxamide bis(trifluoroacetate)

ESI-MS [M+H$^+$]=689.25 calculated for $C_{35}H_{40}N_6O_7S$=688.81

In the compounds (I) according to the invention, the substituent R7 can, according to synthesis scheme 1 or 2, also be introduced subsequently by reductive amination, which is to be illustrated in an exemplary manner using Examples 61 and 67:

Example 61

N-[5-Cyano-1-[(2,4-dimethoxyphenyl)sulphonyl]-3-(2-ethoxypyridin-3-yl)-2-oxo-2,3-dihydro-1H-indol-3-yl]-1'-methyl-4,4'-bipiperidine-1-carboxamide 100 mg (0.138 mmol) of 4-[1-({[5-cyano-1-[(2,4-dimethoxyphenyl)sulphonyl]-3-(2-ethoxypyridin-3-yl)-2-oxo-2,3-dihydro-1H-indol-3-yl]amino}carbonyl)piperidin-4-yl]piperidinium chloride (corresponds to the chloride salt of Example 85) (prepared according to Example 1, process steps 1a) to 1f) and Example 55, process steps 55a) to 55b)) were initially introduced in 10 ml of dichloromethane. 20 μl (0.207 mmol) of aqueous formaldehyde solution (37% strength) were added, and the reaction mixture was stirred for 5 minutes. The solution became slightly turbid. 98 mg (0.69 mmol) of sodium sulphate and 20 μl (0.279 mmol) of glacial acetic acid were added, and the mixture was stirred for 1.5 h. 48.7 mg (0.207 mmol) of the hydrogenation reagent sodium acetoxyborohydride were introduced a little at a time, and after 15 minutes the reaction mixture became clear and then soon turbid again. The mixture was stirred at room temperature overnight and warmed to 40° C. for another hour. The reaction mixture was initially diluted with 30 ml of dichloromethane and then extracted with saturated sodium bicarbonate solution (3×). The combined organic phases were dried over magnesium sulphate and filtered, and the solvent was evaporated under reduced pressure. What was isolated were 75 mg of crude product which was purified by a preparative HPLC on a Chromolith column (RP-18e, from Merck, mobile phases acetonitrile/water, 0.01% acetic acid). What was isolated were 5 mg (0.007 mmol, 5%) of the desired N-[5-cyano-1-[(2,4-dimethoxyphenyl)sulphonyl]-3-(2-ethoxypyridin-3-yl)-2-oxo-2,3-dihydro-1H-indo 1-3-yl]-1'-methyl-4,4'-bipiperidine-1-carboxamide (proportionally present as acetate salt).

ESI-MS [M+H$^+$]=703.2 calculated for $C_{36}H_{42}N_6O_7S$=702.83

Example 67

N-[5-Cyano-1-[(2,4-dimethoxyphenyl)sulphonyl]-3-(2-ethoxypyridin-3-yl)-2-oxo-2,3-dihydro-1H-indol-3-yl]-1'-ethyl-4,4'-bipiperidine-1-carboxamide trifluoroacetate ESI-MS [M+H$^+$]=717.30 calculated for $C_{37}H_{44}N_6O_7S$=716.86

RACEMATE RESOLUTION of the racemic compounds according to EXAMPLES 1 to 90:

In an exemplary manner, using Example 1, the separation of the racemates into its enantiomers (Example 1A and 1B) by separation on a preparative chiral column is shown:

A.) RACEMATE RESOLUTION of the racemic compound according to EXAMPLE 1:

100 mg (0.14 mmol) of the racemic N-[5-cyano-1-[(2,4-dimethoxyphenyl)sulphonyl]-3-(2-ethoxypyridin-3-yl)-2-oxo-2,3-dihydro-1H-indol-3-yl]-4-(1-methylpiperidin-4-yl)piperazine-1-carboxamide (EXAMPLE 1) were separated on a chiral preparative column (Chiralcell OD, flow rate 55 ml/min) using n-heptane/ethanol (700:300) as eluent. The enantiomer which eluted first, having a positive optical rotation (Example 1A), could be isolated in a yield of 19 mg (0.03 mmol, 19%) and the enantiomer which followed, having a negative optical rotation (Example 1B), could be isolated in a yield of 8 mg (0.01 mmol, 8%).

Example 1A (+)-N-[5-Cyano-1-[(2,4-dimethoxyphenyl)sulphonyl]-3-(2-ethoxypyridin-3-yl)-2-oxo-2,3-dihydro-1H-indol-3-yl]-4-(1-methylpiperidin-4-yl)piperazine-1-carboxamide ESI-MS [M+H$^+$]=704.25 calculated for $C_{35}H_{41}N_7O_7S$=703.82

HPLC (Chiralcel OD 0.46 cm×25 cm; n-heptane/ethanol 7:3) $R_f$=9.04 min Optical rotation a (22° C., 589 nm, CHCl$_3$, 1 mg/ml)=dextrorotatory $^1$H-NMR ([D6]-DMSO, 500 MHz) δ [ppm]=8.13 (dd, 1H, J=1.6 Hz, J=4.9 Hz), 7.89 (d, 1H, J=8.9 Hz), 7.88 (d, 1H, J=8.6 Hz), 7.82 (dd, 1H, J=1.7 Hz, J=8.6 Hz), 7.72 (dd, 1H, J=1.5 Hz, J=7.7 Hz), 7.68 (d, 1H, J=1.6 Hz), 7.65 (s, 1H), 7.02 (dd, 1H, J=4.9 Hz, J=7.6 Hz), 6.69 (dd, 1H, J=2.2 Hz, J=8.9 Hz), 6.66 (d, 1H, J=2.1 Hz), 4.17 (m, 2H), 3.86 (s, 3H), 3.45 (s, 3H), 3.21 (m, 4H), 2.77 (m, 2H, J=11.0 Hz), 2.34 (m, 4H), 2.12 (m, 4H), 1.82 (m, 2H), 1.64 (m, 2H, J=10.8 Hz), 1.37 (m, 2H), 1.08 (t, 3H, J=7.0 Hz).

Example 1B (−)-N-[5-Cyano-1-[(2,4-dimethoxyphenyl)sulphonyl]-3-(2-ethoxypyridin-3-yl)-2-oxo-2,3-dihydro-1H-indol-3-yl]-4-(1-methylpiperidin-4-yl)piperazine-1-carbox amide ESI-MS [M+H$^+$]=704.25 calculated for $C_{35}H_{41}N_7O_7S$=703.82 HPLC (Chiralcel OD 0.46 cm×25 cm; n-heptane/ethanol 7:3) $R_f$=25.73 min Optical rotation a (22° C., 589 nm, CHCl$_3$, 1 mg/ml)=laevorotatory $^1$H-NMR ([D6]-DMSO, 500 MHz) δ [ppm]=8.13 (dd, 1H, J=1.2 Hz, J=4.7 Hz), 7.88 (d, 1H, J=8.9 Hz), 7.87 (d, 1H, J=8.5 Hz), 7.81 (dd, 1H, J=1.5 Hz, J=8.5 Hz), 7.72 (dd, 1H, J=1.1 Hz, J=7.6 Hz), 7.68 (s, 1H), 7.64 (s, 1H), 7.01 (dd, 1H, J=4.9 Hz, J=7.6 Hz), 6.69 (dd, 1H, J=1.9 Hz, J=9.0 Hz), 6.66 (d, 1H, J=1.9 Hz), 4.16 (m, 2H), 3.85 (s, 3H), 3.45 (s, 3H), 3.20 (m, 4H), 2.77 (m, 2H, J=11.5 Hz), 2.34 (m, 4H), 2.12 (m, 4H), 1.82 (m, 2H, J=11.3 Hz), 1.64 (m, 2H, J=11.5 Hz), 1.37 (m, 2H), 1.07 (t, 3H, J=7.0 Hz).

B.) RACEMATE RESOLUTION of the racemic compound according to EXAMPLE 31:

N-[5-Cyano-1-[(2,4-dimethoxyphenyl)sulphonyl]-3-(2-ethoxypyridin-3-yl)-2-oxo-2,3-dihydro-1H-indol-3-yl]-4-(4-methylpiperazin-1-yl)piperidine-1-carboxamide (EXAMPLE 31) was separated on a chiral preparative column (Chiralcell OD, flow rate 55 ml/min) using n-heptane/ethanol (700:300) as eluent. The enantiomer which eluted first has a positive optical rotation (Example 31A), and the enantiomer which followed had a negative optical rotation (Example 31B).

Example 31A (+)—N-[5-Cyano-1-[(2,4-dimethoxyphenyl)sulphonyl]-3-(2-ethoxypyridin-3-yl)-2-oxo-2,3-dihydro-1H-indol-3-yl]-4-(4-methylpiperazin-1-yl)piperidine-1-carboxamide ESI-MS [M+H$^+$]=704.80 calculated for $C_{35}H_{41}N_7O_7S$=703.82

HPLC (Chiralcel OD 0.46 cm×25 cm; n-heptane/ethanol 7:3) $R_f$=9.60 min Optical rotation a (22° C., 589 nm, CHCl$_3$, 1 mg/ml)=dextrorotatory $^1$H-NMR ([D6]-DMSO, 500 MHz) δ [ppm]=8.12 (dd, 1H, J=1.6 Hz, J=4.8 Hz), 7.87 (d, 1H, J=8.5 Hz), 7.86 (d, 1H, J=8.8 Hz), 7.81 (dd, 1H, J=1.7 Hz, J=8.6 Hz), 7.73 (dd, 1H, J=1.5 Hz, J=7.7 Hz), 7.69 (s, 1H), 7.67 (d, 1H, J=1.5 Hz), 7.02 (dd, 1H, J=4.9 Hz, J=7.6 Hz), 6.67 (dd, 1H, J=2.2 Hz, J=8.9 Hz), 6.65 (d, 1H, J=2.1 Hz), 4.14 (m, 2H), 3.83 (s, 3H), 3.80 (m, 2H), 3.42 (s, 3H), 2.60 (m, 2H), 2.39-2.10 (m, 9H), 2.10 (s, 3H), 1.60 (m, 2H), 1.12 (m, 2H), 1.06 (t, 3H, J=7.0 Hz).

Example 31B (−)—N-[5-Cyano-1-[(2,4-dimethoxyphenyl)sulphonyl]-3-(2-ethoxypyridin-3-yl)-2-oxo-2,3-dihydro-1H-indol-3-yl]-4-(4-methylpiperazin-1-yl)piperidine-1-carbox amide ESI-MS [M+H$^+$]=704.80 calculated for $C_{35}H_{41}N_7O_7S$=703.82 HPLC (Chiralcel OD 0.46 cm×25 cm; n-heptane/ethanol 7:3) $R_f$=34.31 min Optical rotation α (22° C., 589 nm, CHCl$_3$, 1 mg/ml)=laevorotatory $^1$H-NMR ([D6]-DMSO, 500 MHz) δ [ppm]=8.12 (dd, 1H, J=1.6 Hz, J=4.9 Hz), 7.86 (d, 1H, J=8.7 Hz), 7.85 (d, 1H, J=8.8 Hz), 7.81 (dd, 1H, J=1.6 Hz, J=8.6 Hz), 7.72 (dd, 1H, J=1.4 Hz, J=7.6 Hz), 7.69 (s, 1H), 7.67 (d, 1H, J=1.6 Hz), 7.02 (dd, 1H, J=4.9 Hz, J=7.6 Hz), 6.67 (dd, 1H, J=2.2 Hz, J=8.9 Hz), 6.64 (d, 1H, J=2.0 Hz), 4.13 (m, 2H), 3.83 (s, 3H), 3.80 (m, 2H), 3.42 (s, 3H), 2.60 (m, 2H), 2.42-2.10 (m, 9H), 2.10 (s, 3H), 1.60 (m, 2H), 1.12 (m, 2H), 1.06 (t, 3H, J=7.0 Hz).

C.) RACEMATE RESOLUTION of the racemic compound according to EXAMPLE 37:

N-[5-Cyano-1-[(2,4-dimethoxyphenyl)sulphonyl]-3-(2-ethoxypyridin-3-yl)-2-oxo-2,3-dihydro-1H-indol-3-yl]-4-(4-ethylpiperazin-1-yOpiperidine-1-carboxamide (EXAMPLE 37) was separated on a chiral preparative column (Chiralcell OD, flow rate 55 ml/min) using n-heptane/ethanol (700:300) as eluent. The enantiomer which eluted first had a positive optical rotation (Example 37A), and the enantiomer which followed had a negative optical rotation (Example 37B).

Example 37A (+)—N-[5-Cyano-1-[(2,4-dimethoxyphenyl)sulphonyl]-3-(2-ethoxypyridin-3-yl)-2-oxo-2,3-dihydro-1H-indol-3-yl]-4-(4-ethylpiperazin-1-yl)piperidine-1-carboxamide ESI-MS [M+H$^+$]=718.30 calculated for $C_{36}H_{43}F_3N_7O_7S$=717.85 HPLC (Chiralcel OD 0.46 cm×25 cm; n-heptane/ethanol 7:3) $R_f$=7.29 min Optical rotation a (22° C., 589 nm, CHCl$_3$, 1 mg/ml)=dextrorotatory $^1$H-NMR ([D6]-DMSO, 500 MHz) δ [ppm]=8.13 (dd, 1H, J=1.7 Hz, J=4.9 Hz), 7.89 (d, 1H, J=8.6 Hz), 7.88 (d, 1H, J=8.8 Hz), 7.82 (dd, 1H, J=1.8 Hz, J=8.6 Hz), 7.72 (dd, 1H, J=1.7 Hz, J=7.7 Hz), 7.69 (d, 1H, J=1.7 Hz), 7.67 (s, 1H), 7.02 (dd, 1H, J=4.9 Hz, J=7.7 Hz), 6.69 (dd, 1H, J=2.2 Hz, J=8.9 Hz), 6.66 (d, 1H, J=2.2 Hz), 4.18 (m, 2H), 3.85 (s, 3H), 3.81 (m, 2H), 3.44 (s, 3H), 2.62 (m, 2H), 2.42-2.24 (m, 11H), 1.62 (m, 2H), 1.15 (m, 2H), 1.09 (t, 3H, J=7.1 Hz), 0.96 (t, 3H, J=7.2 Hz).

Example 37B (−)—N-[5-Cyano-1-[(2,4-dimethoxyphenyl)sulphonyl]-3-(2-ethoxypyridin-3-yl)-2-oxo-2,3-dihydro-1H-indol-3-yl]-4-(4-ethylpiperazin-1-yl)piperidine-1-carboxamide ESI-MS [M+H$^+$]=718.25 calculated for $C_{36}H_{43}F_3N_7O_7S$=717.85
HPLC (Chiralcel OD 0.46 cm×25 cm; n-heptane/ethanol 7:3) $R_f$=12.41 min
Optical rotation a (22° C., 589 nm, CHCl$_3$, 1 mg/ml)=laevorotatory $^1$H-NMR ([D6]-DMSO, 500 MHz) δ [ppm]=8.12 (dd, 1H, J=1.6 Hz, J=4.9 Hz), 7.88 (d, 1H, J=8.5 Hz), 7.87 (d, 1H, J=8.8 Hz), 7.80 (dd, 1H, J=1.7 Hz, J=8.6 Hz), 7.71 (dd, 1H, J=1.5 Hz, J=7.7 Hz), 7.68 (d, 1H, J=1.5 Hz), 7.66 (s, 1H), 7.00 (dd, 1H, J=4.9 Hz, J=7.6 Hz), 6.67 (dd, 1H, J=2.2 Hz, J=8.9 Hz), 6.65 (d, 1H, J=2.1 Hz), 4.16 (m, 2H), 3.84 (s, 3H), 3.80 (m, 2H), 3.44 (s, 3H), 2.61 (m, 2H), 2.41-2.23 (m, 11H), 1.60 (m, 2H), 1.14 (m, 2H), 1.08 (t, 3H, J=7.1 Hz), 0.95 (t, 3H, J=7.2 Hz).

D.) RACEMATE RESOLUTION of the racemic compounds 2 to 30, 21 to 36 and 38 to 90:

In a manner analogous to the racemate resolutions of the racemic compounds 1, 31 and 37, it is possible to carry out the separation of the racemates 2 to 30, 32 to 36 and 38 to 90 give the corresponding (+)-enantiomers 2A, 3A, 4A, 5A, 6A, 7A, 8A, 9A, 10A, 11A, 12A, 13A, 14A, 15A, 16A, 17A, 18A, 19A, 20A, 21A, 22A, 23A, 24A, 25A, 26A, 27A, 28A, 29A, 30A and 32A, 33A, 34A, 35A and 38A, 39A, 40A, 41A, 42A, 43A, 44A, 45A, 46A, 47A, 48A, 49A, 50A, 51A, 52A, 53A, 54A, 55A, 56A, 57A, 58A, 59A, 60A, 61A, 62A, 63A, 64A, 65A, 66A, 67A, 68A, 69A, 70A, 71A, 72A, 73A, 74A, 75A, 76A, 77A, 78A, 79A, 80A, 81A, 82A, 83A, 84A, 85A, 86A, 87A, 88A, 89A and 90A
and the corresponding (−)-enantiomers 2B, 3B, 4B, 5B, 6B, 7B, 8B, 9B, 10B, 11B, 12B, 13B, 14B, 15B, 16B, 17B, 18B, 19B, 20B, 21B, 22B, 23B, 24B, 25B, 26B, 27B, 28B, 29B, 30B and 32B, 33B, 34B, 35B and 38B, 39B, 40B, 41B, 42B, 43B, 44B, 45B, 46B, 47B, 48B, 49B, 50B, 51B, 52B, 53B, 54B, 55B, 56B, 57B, 58B, 59B, 60B, 61B, 62B, 63B, 64B, 65B, 66B, 67B, 68B, 69B, 70B, 71B, 72B, 73B, 74B, 75B, 76B, 77B, 78B, 79B, 80B, 81B, 82B, 83B, 84B, 85B, 86B, 87B, 88B, 89B and 90B.

The enantiomers A and B can also be prepared using enantiomerically pure precursors and intermediates, for example analogously to synthesis schemes 1 or 2, preferably via synthesis scheme 1. The separation of the racemic mixture into the (+)-enantiomers and (−)-enantiomers can be carried out by chiral preparative chromatography, preferably via the corresponding amine building block VI.

Example 7B (−)—N-[5-Cyano-1-[(2,4-dimethoxyphenyl)sulphonyl]-3-(2-ethoxypyridin-3-yl)-2-oxo-2,3-dihydro-1H-indol-3-yl]-4-(1-ethylpiperidin-4-yl)piperazine-1-carboxamide trifluoroacetate ESI-MS [M+H$^+$]=718.25 calculated for $C_{36}H_{43}N_7O_7S$=717.85

Example 40B (−)-N-[5-Cyano-3-(2-ethoxypyridin-3-yl)-2-oxo-1-(phenylsulphonyl)-2,3-dihydro-1H-indol-3-yl]-4-(4-ethylpiperazin-1-yl)piperidin-1-carboxamide ESI-MS=658.25 calculated for $C_{34}H_{30}N_7O_5S$=657.79

Example 61B (−)-N-[5-Cyano-1-[(2,4-dimethoxyphenyl)sulphonyl]-3-(2-ethoxypyridin-3-yl)-2-oxo-2,3-dihydro-1H-indol-3-yl]-1′-methyl-4,4′-bipiperidine-1-carboxamide trifluoroacetate ESI-MS [M+H$^+$]=703.30 calculated for $C_{36}H_{42}N_6O_7S$=702.83

$^1$H-NMR ([D6]-DMSO, 500 MHz) δ [ppm]=9.26 (1H, protonation of TFA), 8.12 (dd, 1H, J=1.7 Hz, J=4.9 Hz), 7.87 (dd, 2H, J=1.3 Hz, J=8.7 Hz), 7.80 (dd, 1H, J=1.8 Hz, J=8.5 Hz), 7.80 (m, 2H), 7.66 (s, 1H), 7.00 (dd, 1H, J=4.9 Hz, J=7.6 Hz), 6.68 (dd, 1H, J=2.2 Hz, J=8.9 Hz), 6.65 (d, 1H, J=2.1 Hz), 4.16 (m, 2H), 3.85 (s, 6H), 3.44-3.41 (m, 5H), 2.85 (m, 2H), 2.73 (m, 2H), 2.57 (m, 2H), 1.81 (m, 2H), 1.55 (m, 2H), 1.34-1.22 (m, 4H), 1.08 (t, 3H, J=7.0 Hz), 0.92 (m, 2H).

Example 67B (−)-N-[5-Cyano-1-[(2,4-dimethoxyphenyl)sulphonyl]-3-(2-ethoxypyridin-3-yl)-2-oxo-2,3-dihydro-1H-indol-3-yl]-1′-ethyl-4,4′-bipiperidine-1-carboxamide trifluoroacetate ESI-MS [M+H$^+$]=717.35 calculated for $C_{37}H_{44}N_6O_7S$=716.86

The amines of the general formula X can be prepared according to synthesis scheme 1 or 2 by reductive amination. Hereinbelow, this is shown using the preparation of the amine compound 1-ethyl-4-piperidin-4-ylpiperazine as an example:

Example 91

1-Ethyl-4-piperidin-4-ylpiperazine

91a) tert-Butyl 4-(4-ethylpiperazin-1-yl)piperidine-1-carboxylate

With ice-cooling, 29.2 g (256 mmol) of N-ethylpiperazine and 50.0 g (256 mmol) of tert-butyl 4-oxopiperidine-1-carboxylate (corresponds to 1-Boc-4-piperidone) were initially charged in 800 ml of ethanol and 15.4 g (256 mmol) of glacial acetic acid were added. A little at a time, 16.1 g (256 mmol) of sodium acetoxyborohydride was then added to the cooled reaction mixture. Initially, a slight evolution of gas and, after ⅔ of the reducing agent had been added, foaming could be observed. The reaction mixture was stirred at room temperature overnight. For work-up, 200 ml of 2 N aqueous sodium hydroxide solution were added with cooling to the reaction solution, the solvent ethanol was distilled off and the reaction mixture which remained was diluted with water. The mixture was extracted with diethyl ether (2×) and washed with saturated sodium chloride solution (1×), the combined organic phases were dried over magnesium sulphate and filtered and the solvent was removed under reduced pressure. The desired product was obtained as a yellow oil which was subsequently chromatographed on a 4 l Nutsche filter filled with silica gel, using dichloromethane and 10% methanol as eluents. This gave a total of 40 g (135 mmol, 53%) of tert-butyl 4-(4-ethylpiperazin-1-yl)piperidine-1-carboxylate.

91 b) 1-Ethyl-4-piperidin-4-ylpiperazine as chloride salt

To remove the protective groups, 40 g (135 mmol) of the tert-butyl 4-(4-ethylpiperazin-1-yl)piperidine-1-carboxylate were initially charged in 200 ml of methanol and 1.8 l of dichloromethane, and 100 ml 5-6 M HCl solution in isopropanol were added. The solution became a suspension, and a slight evolution of gas could be observed. The reaction mixture was stirred at 40° C. (water bath temperature) for one hour and at room temperature over the weekend. For complete deprotection to the desired product, another 50 ml of the 5-6 M HCl solution in isopropanol were added, and the mixture was stirred at 40° C. The dichloromethane was distilled off on a rotary evaporator, and another 200 ml of methanol and 30 ml of the 5-6 M HCl solution in isopropanol were added. After one hour of stirring under reflux, a white suspension formed with strong evolution of gas. Subsequently, a low-viscosity suspension was formed, which was cooled to room temperature. The precipitate was filtered off with suction and washed with methanol and diethyl ether. After drying, 36 g (117 mmol, 87%) of 1-ethyl-4-piperidin-4-ylpiperazine were isolated as chloride salt.

$^1$H-NMR (D$_2$O, 400 MHz) δ [ppm]=3.74-3.47 (m, 11H), 3.28 (q, 2H, J=7.3 Hz), 3.06 (dt, 2H, J=2.2 Hz, J=13.2 Hz), 2.38 (m, 2H, J=13.6 Hz), 1.89 (dq, 2H, J=4.1 Hz, J=13.3 Hz), 1.30 (t, 3H, J=7.3 Hz).

The chemical structures of the compounds according to Examples 1 to 90 (racemate) and the corresponding dextrorotatory (+)-enantiomers (Examples Nos. 1 to 90 with the appended letter "A" such as, for example, 1A, 2A, etc. . . . ) and the corresponding laevorotatory (−)-enantiomers (Example Nos. 1 to 90 with the appended letter "B", such as, for example, 1B, 2B, etc. . . . ) are shown in Table 2 below:

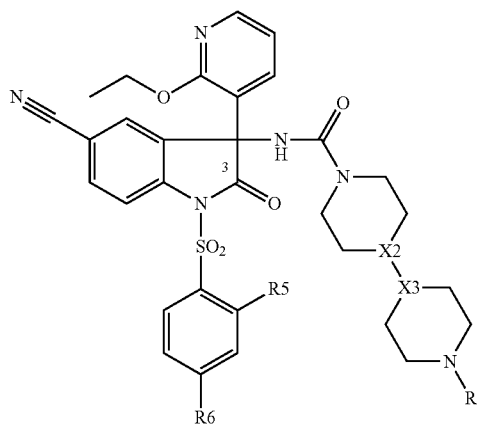

(Ib)

TABLE 2

Compounds of the general formula (Ib) where the radicals R5, R6, R7, X2 and X3 have the meanings mentioned below (in each case per row):

| Exp. No. | X2 | X3 | R5 | R6 | R7 | IUPAC Name (according to ACD-Labs Version 8.00 release product version 8.05) |
|---|---|---|---|---|---|---|
| 1 | N | CH | methoxy | methoxy | methyl | (±)-N-[5-cyano-1-[(2,4-dimethoxyphenyl)sulphonyl]-3-(2-ethoxypyridin-3-yl)-2-oxo-2,3-dihydro-1H-indol-3-yl]-4-(1-methylpiperidin-4-yl)piperazine-1-carboxamide |
| 1A | N | CH | methoxy | methoxy | methyl | (+)-N-[5-cyano-1-[(2,4-dimethoxyphenyl)sulphonyl]-3-(2-ethoxypyridin-3-yl)-2-oxo-2,3-dihydro-1H-indol-3-yl]-4-(1-methylpiperidin-4-yl)piperazine-1-carboxamide |
| 1B | N | CH | methoxy | methoxy | methyl | (−)-N-[5-cyano-1-[(2,4-dimethoxyphenyl)sulphonyl]-3-(2-ethoxypyridin-3-yl)-2-oxo-2,3-dihydro-1H-indol-3-yl]-4-(1-methylpiperidin-4-yl)piperazine-1-carboxamide |
| 2 | N | CH | methoxy | H | methyl | (±)-N-{5-cyano-3-(2-ethoxypyridin-3-yl)-1-[(2-methoxyphenyl)sulphonyl]-2-oxo-2,3-dihydro-1H-indol-3-yl}-4-(1-methylpiperidin-4-yl)piperazine-1-carboxamide |
| 2A | N | CH | methoxy | H | methyl | (+)-N-{5-cyano-3-(2-ethoxypyridin-3-yl)-1-[(2-methoxyphenyl)sulphonyl]-2-oxo-2,3-dihydro-1H-indol-3-yl}-4-(1-methylpiperidin-4-yl)piperazine-1-carboxamide |
| 2B | N | CH | methoxy | H | methyl | (−)-N-{5-cyano-3-(2-ethoxypyridin-3-yl)-1-[(2-methoxyphenyl)sulphonyl]-2-oxo-2,3-dihydro-1H-indol-3-yl}-4-(1-methylpiperidin-4-yl)piperazine-1-carboxamide |
| 3 | N | CH | ethoxy | H | methyl | (±)-N-[5-cyano-1-[(2-ethoxyphenyl)sulphonyl]-3-(2-ethoxypyridin-3-yl)-2-oxo-2,3-dihydro-1H-indol-3-yl]-4-(1-methylpiperidin-4-yl)piperazine-1-carboxamide |
| 3A | N | CH | ethoxy | H | methyl | (+)-N-[5-cyano-1-[(2-ethoxyphenyl)sulphonyl]-3-(2-ethoxypyridin-3-yl)-2-oxo-2,3-dihydro-1H-indol-3-yl]-4-(1-methylpiperidin-4-yl)piperazine-1-carboxamide |
| 3B | N | CH | ethoxy | H | methyl | (−)-N-[5-cyano-1-[(2-ethoxyphenyl)sulphonyl]-3-(2-ethoxypyridin-3-yl)-2-oxo-2,3-dihydro-1H-indol-3-yl]-4-(1-methylpiperidin-4-yl)piperazine-1-carboxamide |
| 4 | N | CH | H | H | methyl | (±)-N-[5-cyano-3-(2-ethoxypyridin-3-yl)-2-oxo-1-(phenylsulphonyl)-2,3-dihydro-1H-indol-3-yl]-4-(1-methylpiperidin-4-yl)piperazine-1-carboxamide |

TABLE 2-continued

Compounds of the general formula (Ib) where the radicals R5, R6, R7, X2 and X3 have the meanings mentioned below (in each case per row):

| Exp. No. | X2 | X3 | R5 | R6 | R7 | IUPAC Name (according to ACD-Labs Version 8.00 release product version 8.05) |
|---|---|---|---|---|---|---|
| 4A | N | CH | H | H | methyl | (+)-N-[5-cyano-3-(2-ethoxypyridin-3-yl)-2-oxo-1-(phenylsulphonyl)-2,3-dihydro-1H-indol-3-yl]-4-(1-methylpiperidin-4-yl)piperazine-1-carboxamide |
| 4B | N | CH | H | H | methyl | (−)-N-[5-cyano-3-(2-ethoxypyridin-3-yl)-2-oxo-1-(phenylsulphonyl)-2,3-dihydro-1H-indol-3-yl]-4-(1-methylpiperidin-4-yl)piperazine-1-carboxamide |
| 5 | N | CH | H | methoxy | methyl | (±)-N-{5-cyano-3-(2-ethoxypyridin-3-yl)-1-[(4-methoxyphenyl)sulphonyl]-2-oxo-2,3-dihydro-1H-indol-3-yl}-4-(1-methylpiperidin-4-yl)piperazine-1-carboxamide |
| 5A | N | CH | H | methoxy | methyl | (+)-N-{5-cyano-3-(2-ethoxypyridin-3-yl)-1-[(4-methoxyphenyl)sulphonyl]-2-oxo-2,3-dihydro-1H-indol-3-yl}-4-(1-methylpiperidin-4-yl)piperazine-1-carboxamide |
| 5B | N | CH | H | methoxy | methyl | (−)-N-{5-cyano-3-(2-ethoxypyridin-3-yl)-1-[(4-methoxyphenyl)sulphonyl]-2-oxo-2,3-dihydro-1H-indol-3-yl}-4-(1-methylpiperidin-4-yl)piperazine-1-carboxamide |
| 6 | N | CH | ethoxy | methoxy | methyl | (±)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(1-methylpiperidin-4-yl)piperazine-1-carboxamide |
| 6A | N | CH | ethoxy | methoxy | methyl | (+)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(1-methylpiperidin-4-yl)piperazine-1-carboxamide |
| 6B | N | CH | ethoxy | methoxy | methyl | (−)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(1-methylpiperidin-4-yl)piperazine-1-carboxamide |
| 7 | N | CH | methoxy | methoxy | ethyl | (±)-N-[5-cyano-1-[(2,4-dimethoxyphenyl)sulphonyl]-3-(2-ethoxypyridin-3-yl)-2-oxo-2,3-dihydro-1H-indol-3-yl]-4-(1-ethylpiperidin-4-yl)piperazine-1-carboxamide |
| 7A | N | CH | methoxy | methoxy | ethyl | (+)-N-[5-cyano-1-[(2,4-dimethoxyphenyl)sulphonyl]-3-(2-ethoxypyridin-3-yl)-2-oxo-2,3-dihydro-1H-indol-3-yl]-4-(1-ethylpiperidin-4-yl)piperazine-1-carboxamide |
| 7B | N | CH | methoxy | methoxy | ethyl | (−)-N-[5-cyano-1-[(2,4-dimethoxyphenyl)sulphonyl]-3-(2-ethoxypyridin-3-yl)-2-oxo-2,3-dihydro-1H-indol-3-yl]-4-(1-ethylpiperidin-4-yl)piperazine-1-carboxamide |
| 8 | N | CH | methoxy | H | ethyl | (±)-N-{5-cyano-3-(2-ethoxypyridin-3-yl)-1-[(2-methoxyphenyl)sulphonyl]-2-oxo-2,3-dihydro-1H-indol-3-yl}-4-(1-ethylpiperidin-4-yl)piperazine-1-carboxamide |
| 8A | N | CH | methoxy | H | ethyl | (+)-N-{5-cyano-3-(2-ethoxypyridin-3-yl)-1-[(2-methoxyphenyl)sulphonyl]-2-oxo-2,3-dihydro-1H-indol-3-yl}-4-(1-ethylpiperidin-4-yl)piperazine-1-carboxamide |
| 8B | N | CH | methoxy | H | ethyl | (−)-N-{5-cyano-3-(2-ethoxypyridin-3-yl)-1-[(2-methoxyphenyl)sulphonyl]-2-oxo-2,3-dihydro-1H-indol-3-yl}-4-(1-ethylpiperidin-4-yl)piperazine-1-carboxamide |
| 9 | N | CH | ethoxy | H | ethyl | (±)-N-[5-cyano-1-[(2-ethoxyphenyl)sulphonyl]-3-(2-ethoxypyridin-3-yl)-2-oxo-2,3-dihydro-1H-indol-3-yl]-4-(1-ethylpiperidin-4-yl)piperazine-1-carboxamide |
| 9A | N | CH | ethoxy | H | ethyl | (+)-N-[5-cyano-1-[(2-ethoxyphenyl)sulphonyl]-3-(2-ethoxypyridin-3-yl)-2-oxo-2,3-dihydro-1H-indol-3-yl]-4-(1-ethylpiperidin-4-yl)piperazine-1-carboxamide |
| 9B | N | CH | ethoxy | H | ethyl | (−)-N-[5-cyano-1-[(2-ethoxyphenyl)sulphonyl]-3-(2-ethoxypyridin-3-yl)-2-oxo-2,3-dihydro-1H-indol-3-yl]-4-(1-ethylpiperidin-4-yl)piperazine-1-carboxamide |
| 10 | N | CH | H | H | ethyl | (±)-N-[5-cyano-3-(2-ethoxypyridin-3-yl)-2-oxo-1-(phenylsulphonyl)-2,3-dihydro-1H-indol-3-yl]-4-(1-ethylpiperidin-4-yl)piperazine-1-carboxamide |
| 10A | N | CH | H | H | ethyl | (+)-N-[5-cyano-3-(2-ethoxypyridin-3-yl)-2-oxo-1-(phenylsulphonyl)-2,3-dihydro-1H-indol-3-yl]-4-(1-ethylpiperidin-4-yl)piperazine-1-carboxamide |
| 10B | N | CH | H | H | ethyl | (−)-N-[5-cyano-3-(2-ethoxypyridin-3-yl)-2-oxo-1-(phenylsulphonyl)-2,3-dihydro-1H-indol-3-yl]-4-(1-ethylpiperidin-4-yl)piperazine-1-carboxamide |
| 11 | N | CH | H | methoxy | ethyl | (±)-N-{5-cyano-3-(2-ethoxypyridin-3-yl)-1-[(4-methoxyphenyl)sulphonyl]-2-oxo-2,3-dihydro-1H-indol-3-yl}-4-(1-ethylpiperidin-4-yl)piperazine-1-carboxamide |
| 11A | N | CH | H | methoxy | ethyl | (+)-N-{5-cyano-3-(2-ethoxypyridin-3-yl)-1-[(4-methoxyphenyl)sulphonyl]-2-oxo-2,3-dihydro-1H-indol-3-yl}-4-(1-ethylpiperidin-4-yl)piperazine-1-carboxamide |
| 11B | N | CH | H | methoxy | ethyl | (−)-N-{5-cyano-3-(2-ethoxypyridin-3-yl)-1-[(4-methoxyphenyl)sulphonyl]-2-oxo-2,3-dihydro-1H-indol-3-yl}-4-(1-ethylpiperidin-4-yl)piperazine-1-carboxamide |
| 12 | N | CH | ethoxy | methoxy | ethyl | (±)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(1-ethylpiperidin-4-yl)piperazine-1-carboxamide |
| 12A | N | CH | ethoxy | methoxy | ethyl | (+)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(1-ethylpiperidin-4-yl)piperazine-1-carboxamide |
| 12B | N | CH | ethoxy | methoxy | ethyl | (−)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(1-ethylpiperidin-4-yl)piperazine-1-carboxamide |
| 13 | N | CH | methoxy | methoxy | n-propyl | (±)-N-[5-cyano-1-[(2,4-dimethoxyphenyl)sulphonyl]-3-(2-ethoxypyridin-3-yl)-2-oxo-2,3-dihydro-1H-indol-3-yl]-4-(1-propylpiperidin-4-yl)piperazine-1-carboxamide |
| 13A | N | CH | methoxy | methoxy | n-propyl | (+)-N-[5-cyano-1-[(2,4-dimethoxyphenyl)sulphonyl]-3-(2-ethoxypyridin-3-yl)-2-oxo-2,3-dihydro-1H-indol-3-yl]-4-(1-propylpiperidin-4-yl)piperazine-1-carboxamide |
| 13B | N | CH | methoxy | methoxy | n-propyl | (−)-N-[5-cyano-1-[(2,4-dimethoxyphenyl)sulphonyl]-3-(2-ethoxypyridin-3-yl)-2-oxo-2,3-dihydro-1H-indol-3-yl]-4-(1-propylpiperidin-4-yl)piperazine-1-carboxamide |
| 14 | N | CH | methoxy | H | n-propyl | (±)-N-{5-cyano-3-(2-ethoxypyridin-3-yl)-1-[(2-methoxyphenyl)sulphonyl]-2-oxo-2,3-dihydro-1H-indol-3-yl}-4-(1-propylpiperidin-4-yl)piperazine-1-carboxamide |
| 14A | N | CH | methoxy | H | n-propyl | (+)-N-{5-cyano-3-(2-ethoxypyridin-3-yl)-1-[(2-methoxyphenyl)sulphonyl]-2-oxo-2,3-dihydro-1H-indol-3-yl}-4-(1-propylpiperidin-4-yl)piperazine-1-carboxamide |
| 14B | N | CH | methoxy | H | n-propyl | (−)-N-{5-cyano-3-(2-ethoxypyridin-3-yl)-1-[(2-methoxyphenyl)sulphonyl]-2-oxo-2,3-dihydro-1H-indol-3-yl}-4-(1-propylpiperidin-4-yl)piperazine-1-carboxamide |
| 15 | N | CH | ethoxy | H | n-propyl | (±)-N-[5-cyano-1-[(2-ethoxyphenyl)sulphonyl]-3-(2-ethoxypyridin-3-yl)-2-oxo-2,3-dihydro-1H-indol-3-yl]-4-(1-propylpiperidin-4-yl)piperazine-1-carboxamide |
| 15A | N | CH | ethoxy | H | n-propyl | (+)-N-[5-cyano-1-[(2-ethoxyphenyl)sulphonyl]-3-(2-ethoxypyridin-3-yl)-2-oxo-2,3-dihydro-1H-indol-3-yl]-4-(1-propylpiperidin-4-yl)piperazine-1-carboxamide |
| 15B | N | CH | ethoxy | H | n-propyl | (−)-N-[5-cyano-1-[(2-ethoxyphenyl)sulphonyl]-3-(2-ethoxypyridin-3-yl)-2-oxo-2,3-dihydro-1H-indol-3-yl]-4-(1-propylpiperidin-4-yl)piperazine-1-carboxamide |
| 16 | N | CH | H | H | n-propyl | (±)-N-[5-cyano-3-(2-ethoxypyridin-3-yl)-2-oxo-1-(phenylsulphonyl)-2,3-dihydro-1H-indol-3-yl]-4-(1-propylpiperidin-4-yl)piperazine-1-carboxamide |

TABLE 2-continued

Compounds of the general formula (Ib) where the radicals R5, R6, R7, X2 and X3 have the meanings mentioned below (in each case per row):

| Exp. No. | X2 | X3 | R5 | R6 | R7 | IUPAC Name (according to ACD-Labs Version 8.00 release product version 8.05) |
|---|---|---|---|---|---|---|
| 16A | N | CH | H | H | n-propyl | (+)-N-[5-cyano-3-(2-ethoxypyridin-3-yl)-2-oxo-1-(phenylsulphonyl)-2,3-dihydro-1H-indol-3-yl]-4-(1-propylpiperidin-4-yl)piperazine-1-carboxamide |
| 16B | N | CH | H | H | n-propyl | (−)-N-[5-cyano-3-(2-ethoxypyridin-3-yl)-2-oxo-1-(phenylsulphonyl)-2,3-dihydro-1H-indol-3-yl]-4-(1-propylpiperidin-4-yl)piperazine-1-carboxamide |
| 17 | N | CH | H | methoxy | n-propyl | (±)-N-{5-cyano-3-(2-ethoxypyridin-3-yl)-1-[(4-methoxyphenyl)sulphonyl]-2-oxo-2,3-dihydro-1H-indol-3-yl}-4-(1-propylpiperidin-4-yl)piperazine-1-carboxamide |
| 17A | N | CH | H | methoxy | n-propyl | (+)-N-{5-cyano-3-(2-ethoxypyridin-3-yl)-1-[(4-methoxyphenyl)sulphonyl]-2-oxo-2,3-dihydro-1H-indol-3-yl}-4-(1-propylpiperidin-4-yl)piperazine-1-carboxamide |
| 17B | N | CH | H | methoxy | n-propyl | (−)-N-{5-cyano-3-(2-ethoxypyridin-3-yl)-1-[(4-methoxyphenyl)sulphonyl]-2-oxo-2,3-dihydro-1H-indol-3-yl}-4-(1-propylpiperidin-4-yl)piperazine-1-carboxamide |
| 18 | N | CH | ethoxy | methoxy | n-propyl | (±)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(1-propylpiperidin-4-yl)piperazine-1-carboxamide |
| 18A | N | CH | ethoxy | methoxy | n-propyl | (+)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(1-propylpiperidin-4-yl)piperazine-1-carboxamide |
| 18B | N | CH | ethoxy | methoxy | n-propyl | (−)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(1-propylpiperidin-4-yl)piperazine-1-carboxamide |
| 19 | N | CH | methoxy | methoxy | isopropyl | (±)-N-[5-cyano-1-[(2,4-dimethoxyphenyl)sulphonyl]-3-(2-ethoxypyridin-3-yl)-2-oxo-2,3-dihydro-1H-indol-3-yl]-4-(1-isopropylpiperidin-4-yl)piperazine-1-carboxamide |
| 19A | N | CH | methoxy | methoxy | isopropyl | (+)-N-[5-cyano-1-[(2,4-dimethoxyphenyl)sulphonyl]-3-(2-ethoxypyridin-3-yl)-2-oxo-2,3-dihydro-1H-indol-3-yl]-4-(1-isopropylpiperidin-4-yl)piperazine-1-carboxamide |
| 19B | N | CH | methoxy | methoxy | isopropyl | (−)-N-[5-cyano-1-[(2,4-dimethoxyphenyl)sulphonyl]-3-(2-ethoxypyridin-3-yl)-2-oxo-2,3-dihydro-1H-indol-3-yl]-4-(1-isopropylpiperidin-4-yl)piperazine-1-carboxamide |
| 20 | N | CH | methoxy | H | isopropyl | (±)-N-{5-cyano-3-(2-ethoxypyridin-3-yl)-1-[(2-methoxyphenyl)sulphonyl]-2-oxo-2,3-dihydro-1H-indol-3-yl}-4-(1-isopropylpiperidin-4-yl)piperazine-1-carboxamide |
| 20A | N | CH | methoxy | H | isopropyl | (+)-N-{5-cyano-3-(2-ethoxypyridin-3-yl)-1-[(2-methoxyphenyl)sulphonyl]-2-oxo-2,3-dihydro-1H-indol-3-yl}-4-(1-isopropylpiperidin-4-yl)piperazine-1-carboxamide |
| 20B | N | CH | methoxy | H | isopropyl | (−)-N-{5-cyano-3-(2-ethoxypyridin-3-yl)-1-[(2-methoxyphenyl)sulphonyl]-2-oxo-2,3-dihydro-1H-indol-3-yl}-4-(1-isopropylpiperidin-4-yl)piperazine-1-carboxamide |
| 21 | N | CH | ethoxy | H | isopropyl | (±)-N-[5-cyano-1-[(2-ethoxyphenyl)sulphonyl]-3-(2-ethoxypyridin-3-yl)-2-oxo-2,3-dihydro-1H-indol-3-yl]-4-(1-isopropylpiperidin-4-yl)piperazine-1-carboxamide |
| 21A | N | CH | ethoxy | H | isopropyl | (+)-N-[5-cyano-1-[(2-ethoxyphenyl)sulphonyl]-3-(2-ethoxypyridin-3-yl)-2-oxo-2,3-dihydro-1H-indol-3-yl]-4-(1-isopropylpiperidin-4-yl)piperazine-1-carboxamide |
| 21B | N | CH | ethoxy | H | isopropyl | (−)-N-[5-cyano-1-[(2-ethoxyphenyl)sulphonyl]-3-(2-ethoxypyridin-3-yl)-2-oxo-2,3-dihydro-1H-indol-3-yl]-4-(1-isopropylpiperidin-4-yl)piperazine-1-carboxamide |
| 22 | N | CH | H | H | isopropyl | (±)-N-[5-cyano-3-(2-ethoxypyridin-3-yl)-2-oxo-1-(phenylsulphonyl)-2,3-dihydro-1H-indol-3-yl]-4-(1-isopropylpiperidin-4-yl)piperazine-1-carboxamide |
| 22A | N | CH | H | H | isopropyl | (+)-N-[5-cyano-3-(2-ethoxypyridin-3-yl)-2-oxo-1-(phenylsulphonyl)-2,3-dihydro-1H-indol-3-yl]-4-(1-isopropylpiperidin-4-yl)piperazine-1-carboxamide |
| 22B | N | CH | H | H | isopropyl | (−)-N-[5-cyano-3-(2-ethoxypyridin-3-yl)-2-oxo-1-(phenylsulphonyl)-2,3-dihydro-1H-indol-3-yl]-4-(1-isopropylpiperidin-4-yl)piperazine-1-carboxamide |
| 23 | N | CH | H | methoxy | isopropyl | (±)-N-{5-cyano-3-(2-ethoxypyridin-3-yl)-1-[(4-methoxyphenyl)sulphonyl]-2-oxo-2,3-dihydro-1H-indol-3-yl}-4-(1-isopropylpiperidin-4-yl)piperazine-1-carboxamide |
| 23A | N | CH | H | methoxy | isopropyl | (+)-N-{5-cyano-3-(2-ethoxypyridin-3-yl)-1-[(4-methoxyphenyl)sulphonyl]-2-oxo-2,3-dihydro-1H-indol-3-yl}-4-(1-isopropylpiperidin-4-yl)piperazine-1-carboxamide |
| 23B | N | CH | H | methoxy | isopropyl | (−)-N-{5-cyano-3-(2-ethoxypyridin-3-yl)-1-[(4-methoxyphenyl)sulphonyl]-2-oxo-2,3-dihydro-1H-indol-3-yl}-4-(1-isopropylpiperidin-4-yl)piperazine-1-carboxamide |
| 24 | N | CH | ethoxy | methoxy | isopropyl | (±)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(1-isopropylpiperidin-4-yl)piperazine-1-carboxamide |
| 24A | N | CH | ethoxy | methoxy | isopropyl | (+)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(1-isopropylpiperidin-4-yl)piperazine-1-carboxamide |
| 24B | N | CH | ethoxy | methoxy | isopropyl | (−)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(1-isopropylpiperidin-4-yl)piperazine-1-carboxamide |
| 25 | N | CH | methoxy | methoxy | H | (±)-N-[5-cyano-1-[(2,4-dimethoxyphenyl)sulphonyl]-3-(2-ethoxypyridin-3-yl)-2-oxo-2,3-dihydro-1H-indol-3-yl]-4-piperidin-4-ylpiperazine-1-carboxamide |
| 25A | N | CH | methoxy | methoxy | H | (+)-N-[5-cyano-1-[(2,4-dimethoxyphenyl)sulphonyl]-3-(2-ethoxypyridin-3-yl)-2-oxo-2,3-dihydro-1H-indol-3-yl]-4-piperidin-4-ylpiperazine-1-carboxamide |
| 25B | N | CH | methoxy | methoxy | H | (−)-N-[5-cyano-1-[(2,4-dimethoxyphenyl)sulphonyl]-3-(2-ethoxypyridin-3-yl)-2-oxo-2,3-dihydro-1H-indol-3-yl]-4-piperidin-4-ylpiperazine-1-carboxamide |
| 26 | N | CH | methoxy | H | H | (±)-N-{5-cyano-3-(2-ethoxypyridin-3-yl)-1-[(2-methoxyphenyl)sulphonyl]-2-oxo-2,3-dihydro-1H-indol-3-yl}-4-piperidin-4-ylpiperazine-1-carboxamide |
| 26A | N | CH | methoxy | H | H | (+)-N-{5-cyano-3-(2-ethoxypyridin-3-yl)-1-[(2-methoxyphenyl)sulphonyl]-2-oxo-2,3-dihydro-1H-indol-3-yl}-4-piperidin-4-ylpiperazine-1-carboxamide |
| 26B | N | CH | methoxy | H | H | (−)-N-{5-cyano-3-(2-ethoxypyridin-3-yl)-1-[(2-methoxyphenyl)sulphonyl]-2-oxo-2,3-dihydro-1H-indol-3-yl}-4-piperidin-4-ylpiperazine-1-carboxamide |
| 27 | N | CH | ethoxy | H | H | (±)-N-[5-cyano-1-[(2-ethoxyphenyl)sulphonyl]-3-(2-ethoxypyridin-3-yl)-2-oxo-2,3-dihydro-1H-indol-3-yl]-4-piperidin-4-ylpiperazine-1-carboxamide |
| 27A | N | CH | ethoxy | H | H | (+)-N-[5-cyano-1-[(2-ethoxyphenyl)sulphonyl]-3-(2-ethoxypyridin-3-yl)-2-oxo-2,3-dihydro-1H-indol-3-yl]-4-piperidin-4-ylpiperazine-1-carboxamide |

TABLE 2-continued

Compounds of the general formula (Ib) where the radicals R5, R6, R7, X2 and X3 have the meanings mentioned below (in each case per row):

| Exp. No. | X2 | X3 | R5 | R6 | R7 | IUPAC Name (according to ACD-Labs Version 8.00 release product version 8.05) |
|---|---|---|---|---|---|---|
| 27B | N | CH | ethoxy | H | H | (−)-N-[5-cyano-1-[(2-ethoxyphenyl)sulphonyl]-3-(2-ethoxypyridin-3-yl)-2-oxo-2,3-dihydro-1H-indol-3-yl]-4-piperidin-4-ylpiperazine-1-carboxamide |
| 28 | N | CH | H | H | H | (±)-N-[5-cyano-3-(2-ethoxypyridin-3-yl)-2-oxo-1-(phenylsulphonyl)-2,3-dihydro-1H-indol-3-yl]-4-piperidin-4-ylpiperazine-1-carboxamide |
| 28A | N | CH | H | H | H | (+)-N-[5-cyano-3-(2-ethoxypyridin-3-yl)-2-oxo-1-(phenylsulphonyl)-2,3-dihydro-1H-indol-3-yl]-4-piperidin-4-ylpiperazine-1-carboxamide |
| 28B | N | CH | H | H | H | (−)-N-[5-cyano-3-(2-ethoxypyridin-3-yl)-2-oxo-1-(phenylsulphonyl)-2,3-dihydro-1H-indol-3-yl]-4-piperidin-4-ylpiperazine-1-carboxamide |
| 29 | N | CH | H | methoxy | H | (±)-N-{5-cyano-3-(2-ethoxypyridin-3-yl)-1-[(4-methoxyphenyl)sulphonyl]-2-oxo-2,3-dihydro-1H-indol-3-yl}-4-piperidin-4-ylpiperazine-1-carboxamide |
| 29A | N | CH | H | methoxy | H | (+)-N-{5-cyano-3-(2-ethoxypyridin-3-yl)-1-[(4-methoxyphenyl)sulphonyl]-2-oxo-2,3-dihydro-1H-indol-3-yl}-4-piperidin-4-ylpiperazine-1-carboxamide |
| 29B | N | CH | H | methoxy | H | (−)-N-{5-cyano-3-(2-ethoxypyridin-3-yl)-1-[(4-methoxyphenyl)sulphonyl]-2-oxo-2,3-dihydro-1H-indol-3-yl}-4-piperidin-4-ylpiperazine-1-carboxamide |
| 30 | N | CH | ethoxy | methoxy | H | (±)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-piperidin-4-ylpiperazine-1-carboxamide |
| 30A | N | CH | ethoxy | methoxy | H | (+)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-piperidin-4-ylpiperazine-1-carboxamide |
| 30B | N | CH | ethoxy | methoxy | H | (−)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-piperidin-4-ylpiperazine-1-carboxamide |
| 31 | CH | N | methoxy | methoxy | methyl | (±)-N-[5-cyano-1-[(2,4-dimethoxyphenyl)sulphonyl]-3-(2-ethoxypyridin-3-yl)-2-oxo-2,3-dihydro-1H-indol-3-yl]-4-(4-methylpiperazin-1-yl)piperidine-1-carboxamide |
| 31A | CH | N | methoxy | methoxy | methyl | (+)-N-[5-cyano-1-[(2,4-dimethoxyphenyl)sulphonyl]-3-(2-ethoxypyridin-3-yl)-2-oxo-2,3-dihydro-1H-indol-3-yl]-4-(4-methylpiperazin-1-yl)piperidine-1-carboxamide |
| 31B | CH | N | methoxy | methoxy | methyl | (−)-N-[5-cyano-1-[(2,4-dimethoxyphenyl)sulphonyl]-3-(2-ethoxypyridin-3-yl)-2-oxo-2,3-dihydro-1H-indol-3-yl]-4-(4-methylpiperazin-1-yl)piperidine-1-carboxamide |
| 32 | CH | N | methoxy | H | methyl | (±)-N-{5-cyano-3-(2-ethoxypyridin-3-yl)-1-[(2-methoxyphenyl)sulphonyl]-2-oxo-2,3-dihydro-1H-indol-3-yl}-4-(4-methylpiperazin-1-yl)piperidine-1-carboxamide |
| 32A | CH | N | methoxy | H | methyl | (+)-N-{5-cyano-3-(2-ethoxypyridin-3-yl)-1-[(2-methoxyphenyl)sulphonyl]-2-oxo-2,3-dihydro-1H-indol-3-yl}-4-(4-methylpiperazin-1-yl)piperidine-1-carboxamide |
| 32B | CH | N | methoxy | H | methyl | (−)-N-{5-cyano-3-(2-ethoxypyridin-3-yl)-1-[(2-methoxyphenyl)sulphonyl]-2-oxo-2,3-dihydro-1H-indol-3-yl}-4-(4-methylpiperazin-1-yl)piperidine-1-carboxamide |
| 33 | CH | N | ethoxy | H | methyl | (±)-N-[5-cyano-1-[(2-ethoxyphenyl)sulphonyl]-3-(2-ethoxypyridin-3-yl)-2-oxo-2,3-dihydro-1H-indol-3-yl]-4-(4-methylpiperazin-1-yl)piperidine-1-carboxamide |
| 33A | CH | N | ethoxy | H | methyl | (+)-N-[5-cyano-1-[(2-ethoxyphenyl)sulphonyl]-3-(2-ethoxypyridin-3-yl)-2-oxo-2,3-dihydro-1H-indol-3-yl]-4-(4-methylpiperazin-1-yl)piperidine-1-carboxamide |
| 33B | CH | N | ethoxy | H | methyl | (−)-N-[5-cyano-1-[(2-ethoxyphenyl)sulphonyl]-3-(2-ethoxypyridin-3-yl)-2-oxo-2,3-dihydro-1H-indol-3-yl]-4-(4-methylpiperazin-1-yl)piperidine-1-carboxamide |
| 34 | CH | N | H | H | methyl | (±)-N-[5-cyano-3-(2-ethoxypyridin-3-yl)-2-oxo-1-(phenylsulphonyl)-2,3-dihydro-1H-indol-3-yl]-4-(4-methylpiperazin-1-yl)piperidine-1-carboxamide |
| 34A | CH | N | H | H | methyl | (+)-N-[5-cyano-3-(2-ethoxypyridin-3-yl)-2-oxo-1-(phenylsulphonyl)-2,3-dihydro-1H-indol-3-yl]-4-(4-methylpiperazin-1-yl)piperidine-1-carboxamide |
| 34B | CH | N | H | H | methyl | (−)-N-[5-cyano-3-(2-ethoxypyridin-3-yl)-2-oxo-1-(phenylsulphonyl)-2,3-dihydro-1H-indol-3-yl]-4-(4-methylpiperazin-1-yl)piperidine-1-carboxamide |
| 35 | CH | N | H | methoxy | methyl | (±)-N-{5-cyano-3-(2-ethoxypyridin-3-yl)-1-[(4-methoxyphenyl)sulphonyl]-2-oxo-2,3-dihydro-1H-indol-3-yl}-4-(4-methylpiperazin-1-yl)piperidine-1-carboxamide |
| 35A | CH | N | H | methoxy | methyl | (+)-N-{5-cyano-3-(2-ethoxypyridin-3-yl)-1-[(4-methoxyphenyl)sulphonyl]-2-oxo-2,3-dihydro-1H-indol-3-yl}-4-(4-methylpiperazin-1-yl)piperidine-1-carboxamide |
| 35B | CH | N | H | methoxy | methyl | (−)-N-{5-cyano-3-(2-ethoxypyridin-3-yl)-1-[(4-methoxyphenyl)sulphonyl]-2-oxo-2,3-dihydro-1H-indol-3-yl}-4-(4-methylpiperazin-1-yl)piperidine-1-carboxamide |
| 36 | CH | N | ethoxy | methoxy | methyl | (±)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(4-methylpiperazin-1-yl)piperidine-1-carboxamide |
| 36A | CH | N | ethoxy | methoxy | methyl | (+)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(4-methylpiperazin-1-yl)piperidine-1-carboxamide |
| 36B | CH | N | ethoxy | methoxy | methyl | (−)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(4-methylpiperazin-1-yl)piperidine-1-carboxamide |
| 37 | CH | N | methoxy | methoxy | ethyl | (±)-N-[5-cyano-1-[(2,4-dimethoxyphenyl)sulphonyl]-3-(2-ethoxypyridin-3-yl)-2-oxo-2,3-dihydro-1H-indol-3-yl]-4-(4-ethylpiperazin-1-yl)piperidine-1-carboxamide |
| 37A | CH | N | methoxy | methoxy | ethyl | (+)-N-[5-cyano-1-[(2,4-dimethoxyphenyl)sulphonyl]-3-(2-ethoxypyridin-3-yl)-2-oxo-2,3-dihydro-1H-indol-3-yl]-4-(4-ethylpiperazin-1-yl)piperidine-1-carboxamide |
| 37B | CH | N | methoxy | methoxy | ethyl | (−)-N-[5-cyano-1-[(2,4-dimethoxyphenyl)sulphonyl]-3-(2-ethoxypyridin-3-yl)-2-oxo-2,3-dihydro-1H-indol-3-yl]-4-(4-ethylpiperazin-1-yl)piperidine-1-carboxamide |
| 38 | CH | N | methoxy | H | ethyl | (±)-N-{5-cyano-3-(2-ethoxypyridin-3-yl)-1-[(2-methoxyphenyl)sulphonyl]-2-oxo-2,3-dihydro-1H-indol-3-yl}-4-(4-ethylpiperazin-1-yl)piperidine-1-carboxamide |
| 38A | CH | N | methoxy | H | ethyl | (+)-N-{5-cyano-3-(2-ethoxypyridin-3-yl)-1-[(2-methoxyphenyl)sulphonyl]-2-oxo-2,3-dihydro-1H-indol-3-yl}-4-(4-ethylpiperazin-1-yl)piperidine-1-carboxamide |
| 38B | CH | N | methoxy | H | ethyl | (−)-N-{5-cyano-3-(2-ethoxypyridin-3-yl)-1-[(2-methoxyphenyl)sulphonyl]-2-oxo-2,3-dihydro-1H-indol-3-yl}-4-(4-ethylpiperazin-1-yl)piperidine-1-carboxamide |
| 39 | CH | N | ethoxy | H | ethyl | (±)-N-[5-cyano-1-[(2-ethoxyphenyl)sulphonyl]-3-(2-ethoxypyridin-3-yl)-2-oxo-2,3-dihydro-1H-indol-3-yl]-4-(4-ethylpiperazin-1-yl)piperidine-1-carboxamide |
| 39A | CH | N | ethoxy | H | ethyl | (+)-N-[5-cyano-1-[(2-ethoxyphenyl)sulphonyl]-3-(2-ethoxypyridin-3-yl)-2-oxo-2,3-dihydro-1H-indol-3-yl]-4-(4-ethylpiperazin-1-yl)piperidine-1-carboxamide |

TABLE 2-continued

Compounds of the general formula (Ib) where the radicals R5, R6, R7, X2 and X3 have the meanings mentioned below (in each case per row):

| Exp. No. | X2 | X3 | R5 | R6 | R7 | IUPAC Name (according to ACD-Labs Version 8.00 release product version 8.05) |
|---|---|---|---|---|---|---|
| 39B | CH | N | ethoxy | H | ethyl | (−)-N-[5-cyano-1-[(2-ethoxyphenyl)sulphonyl]-3-(2-ethoxypyridin-3-yl)-2-oxo-2,3-dihydro-1H-indol-3-yl]-4-(4-ethylpiperazin-1-yl)piperidine-1-carboxamide |
| 40 | CH | N | H | H | ethyl | (±)-N-[5-cyano-3-(2-ethoxypyridin-3-yl)-2-oxo-1-(phenylsulphonyl)-2,3-dihydro-1H-indol-3-yl]-4-(4-ethylpiperazin-1-yl)piperidine-1-carboxamide |
| 40A | CH | N | H | H | ethyl | (+)-N-[5-cyano-3-(2-ethoxypyridin-3-yl)-2-oxo-1-(phenylsulphonyl)-2,3-dihydro-1H-indol-3-yl]-4-(4-ethylpiperazin-1-yl)piperidine-1-carboxamide |
| 40B | CH | N | H | H | ethyl | (−)-N-[5-cyano-3-(2-ethoxypyridin-3-yl)-2-oxo-1-(phenylsulphonyl)-2,3-dihydro-1H-indol-3-yl]-4-(4-ethylpiperazin-1-yl)piperidine-1-carboxamide |
| 41 | CH | N | H | methoxy | ethyl | (±)-N-{5-cyano-3-(2-ethoxypyridin-3-yl)-1-[(4-methoxyphenyl)sulphonyl]-2-oxo-2,3-dihydro-1H-indol-3-yl}-4-(4-ethylpiperazin-1-yl)piperidine-1-carboxamide |
| 41A | CH | N | H | methoxy | ethyl | (+)-N-{5-cyano-3-(2-ethoxypyridin-3-yl)-1-[(4-methoxyphenyl)sulphonyl]-2-oxo-2,3-dihydro-1H-indol-3-yl}-4-(4-ethylpiperazin-1-yl)piperidine-1-carboxamide |
| 41B | CH | N | H | methoxy | ethyl | (−)-N-{5-cyano-3-(2-ethoxypyridin-3-yl)-1-[(4-methoxyphenyl)sulphonyl]-2-oxo-2,3-dihydro-1H-indol-3-yl}-4-(4-ethylpiperazin-1-yl)piperidine-1-carboxamide |
| 42 | CH | N | ethoxy | methoxy | ethyl | (±)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(4-ethylpiperazin-1-yl)piperidine-1-carboxamide |
| 42A | CH | N | ethoxy | methoxy | ethyl | (+)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(4-ethylpiperazin-1-yl)piperidine-1-carboxamide |
| 42B | CH | N | ethoxy | methoxy | ethyl | (−)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(4-ethylpiperazin-1-yl)piperidine-1-carboxamide |
| 43 | CH | N | methoxy | methoxy | n-propyl | (±)-N-[5-cyano-1-[(2,4-dimethoxyphenyl)sulphonyl]-3-(2-ethoxypyridin-3-yl)-2-oxo-2,3-dihydro-1H-indol-3-yl]-4-(4-propylpiperazin-1-yl)piperidine-1-carboxamide |
| 43A | CH | N | methoxy | methoxy | n-propyl | (+)-N-[5-cyano-1-[(2,4-dimethoxyphenyl)sulphonyl]-3-(2-ethoxypyridin-3-yl)-2-oxo-2,3-dihydro-1H-indol-3-yl]-4-(4-propylpiperazin-1-yl)piperidine-1-carboxamide |
| 43B | CH | N | methoxy | methoxy | n-propyl | (−)-N-[5-cyano-1-[(2,4-dimethoxyphenyl)sulphonyl]-3-(2-ethoxypyridin-3-yl)-2-oxo-2,3-dihydro-1H-indol-3-yl]-4-(4-propylpiperazin-1-yl)piperidine-1-carboxamide |
| 44 | CH | N | methoxy | H | n-propyl | (±)-N-{5-cyano-3-(2-ethoxypyridin-3-yl)-1-[(2-methoxyphenyl)sulphonyl]-2-oxo-2,3-dihydro-1H-indol-3-yl}-4-(4-propylpiperazin-1-yl)piperidine-1-carboxamide |
| 44A | CH | N | methoxy | H | n-propyl | (+)-N-{5-cyano-3-(2-ethoxypyridin-3-yl)-1-[(2-methoxyphenyl)sulphonyl]-2-oxo-2,3-dihydro-1H-indol-3-yl}-4-(4-propylpiperazin-1-yl)piperidine-1-carboxamide |
| 44B | CH | N | methoxy | H | n-propyl | (−)-N-{5-cyano-3-(2-ethoxypyridin-3-yl)-1-[(2-methoxyphenyl)sulphonyl]-2-oxo-2,3-dihydro-1H-indol-3-yl}-4-(4-propylpiperazin-1-yl)piperidine-1-carboxamide |
| 45 | CH | N | ethoxy | H | n-propyl | (±)-N-[5-cyano-1-[(2-ethoxyphenyl)sulphonyl]-3-(2-ethoxypyridin-3-yl)-2-oxo-2,3-dihydro-1H-indol-3-yl]-4-(4-propylpiperazin-1-yl)piperidine-1-carboxamide |
| 45A | CH | N | ethoxy | H | n-propyl | (+)-N-[5-cyano-1-[(2-ethoxyphenyl)sulphonyl]-3-(2-ethoxypyridin-3-yl)-2-oxo-2,3-dihydro-1H-indol-3-yl]-4-(4-propylpiperazin-1-yl)piperidine-1-carboxamide |
| 45B | CH | N | ethoxy | H | n-propyl | (−)-N-[5-cyano-1-[(2-ethoxyphenyl)sulphonyl]-3-(2-ethoxypyridin-3-yl)-2-oxo-2,3-dihydro-1H-indol-3-yl]-4-(4-propylpiperazin-1-yl)piperidine-1-carboxamide |
| 46 | CH | N | H | H | n-propyl | (±)-N-[5-cyano-3-(2-ethoxypyridin-3-yl)-2-oxo-1-(phenylsulphonyl)-2,3-dihydro-1H-indol-3-yl]-4-(4-propylpiperazin-1-yl)piperidine-1-carboxamide |
| 46A | CH | N | H | H | n-propyl | (+)-N-[5-cyano-3-(2-ethoxypyridin-3-yl)-2-oxo-1-(phenylsulphonyl)-2,3-dihydro-1H-indol-3-yl]-4-(4-propylpiperazin-1-yl)piperidine-1-carboxamide |
| 46B | CH | N | H | H | n-propyl | (−)-N-[5-cyano-3-(2-ethoxypyridin-3-yl)-2-oxo-1-(phenylsulphonyl)-2,3-dihydro-1H-indol-3-yl]-4-(4-propylpiperazin-1-yl)piperidine-1-carboxamide |
| 47 | CH | N | H | methoxy | n-propyl | (±)-N-{5-cyano-3-(2-ethoxypyridin-3-yl)-1-[(4-methoxyphenyl)sulphonyl]-2-oxo-2,3-dihydro-1H-indol-3-yl}-4-(4-propylpiperazin-1-yl)piperidine-1-carboxamide |
| 47A | CH | N | H | methoxy | n-propyl | (+)-N-{5-cyano-3-(2-ethoxypyridin-3-yl)-1-[(4-methoxyphenyl)sulphonyl]-2-oxo-2,3-dihydro-1H-indol-3-yl}-4-(4-propylpiperazin-1-yl)piperidine-1-carboxamide |
| 47B | CH | N | H | methoxy | n-propyl | (−)-N-{5-cyano-3-(2-ethoxypyridin-3-yl)-1-[(4-methoxyphenyl)sulphonyl]-2-oxo-2,3-dihydro-1H-indol-3-yl}-4-(4-propylpiperazin-1-yl)piperidine-1-carboxamide |
| 48 | CH | N | ethoxy | methoxy | n-propyl | (±)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(4-propylpiperazin-1-yl)piperidine-1-carboxamide |
| 48A | CH | N | ethoxy | methoxy | n-propyl | (+)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(4-propylpiperazin-1-yl)piperidine-1-carboxamide |
| 48B | CH | N | ethoxy | methoxy | n-propyl | (−)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(4-propylpiperazin-1-yl)piperidine-1-carboxamide |
| 49 | CH | N | methoxy | methoxy | isopropyl | (±)-N-[5-cyano-1-[(2,4-dimethoxyphenyl)sulphonyl]-3-(2-ethoxypyridin-3-yl)-2-oxo-2,3-dihydro-1H-indol-3-yl]-4-(4-isopropylpiperazin-1-yl)piperidine-1-carboxamide |
| 49A | CH | N | methoxy | methoxy | isopropyl | (+)-N-[5-cyano-1-[(2,4-dimethoxyphenyl)sulphonyl]-3-(2-ethoxypyridin-3-yl)-2-oxo-2,3-dihydro-1H-indol-3-yl]-4-(4-isopropylpiperazin-1-yl)piperidine-1-carboxamide |
| 49B | CH | N | methoxy | methoxy | isopropyl | (−)-N-[5-cyano-1-[(2,4-dimethoxyphenyl)sulphonyl]-3-(2-ethoxypyridin-3-yl)-2-oxo-2,3-dihydro-1H-indol-3-yl]-4-(4-isopropylpiperazin-1-yl)piperidine-1-carboxamide |
| 50 | CH | N | methoxy | H | isopropyl | (±)-N-{5-cyano-3-(2-ethoxypyridin-3-yl)-1-[(2-methoxyphenyl)sulphonyl]-2-oxo-2,3-dihydro-1H-indol-3-yl}-4-(4-isopropylpiperazin-1-yl)piperidine-1-carboxamide |
| 50A | CH | N | methoxy | H | isopropyl | (+)-N-{5-cyano-3-(2-ethoxypyridin-3-yl)-1-[(2-methoxyphenyl)sulphonyl]-2-oxo-2,3-dihydro-1H-indol-3-yl}-4-(4-isopropylpiperazin-1-yl)piperidine-1-carboxamide |
| 50B | CH | N | methoxy | H | isopropyl | (−)-N-{5-cyano-3-(2-ethoxypyridin-3-yl)-1-[(2-methoxyphenyl)sulphonyl]-2-oxo-2,3-dihydro-1H-indol-3-yl}-4-(4-isopropylpiperazin-1-yl)piperidine-1-carboxamide |
| 51 | CH | N | ethoxy | H | isopropyl | (±)-N-[5-cyano-1-[(2-ethoxyphenyl)sulphonyl]-3-(2-ethoxypyridin-3-yl)-2-oxo-2,3-dihydro-1H-indol-3-yl]-4-(4-isopropylpiperazin-1-yl)piperidine-1-carboxamide |
| 51A | CH | N | ethoxy | H | isopropyl | (+)-N-[5-cyano-1-[(2-ethoxyphenyl)sulphonyl]-3-(2-ethoxypyridin-3-yl)-2-oxo-2,3-dihydro-1H-indol-3-yl]-4-(4-isopropylpiperazin-1-yl)piperidine-1-carboxamide |

TABLE 2-continued

Compounds of the general formula (Ib) where the radicals R5, R6, R7, X2 and X3 have the meanings mentioned below (in each case per row):

| Exp. No. | X2 | X3 | R5 | R6 | R7 | IUPAC Name (according to ACD-Labs Version 8.00 release product version 8.05) |
|---|---|---|---|---|---|---|
| 51B | CH | N | ethoxy | H | isopropyl | (−)-N-[5-cyano-1-[(2-ethoxyphenyl)sulphonyl]-3-(2-ethoxypyridin-3-yl)-2-oxo-2,3-dihydro-1H-indol-3-yl]-4-(4-isopropylpiperazin-1-yl)piperidine-1-carboxamide |
| 52 | CH | N | H | H | isopropyl | (±)-N-[5-cyano-3-(2-ethoxypyridin-3-yl)-2-oxo-1-(phenylsulphonyl)-2,3-dihydro-1H-indol-3-yl]-4-(4-isopropylpiperazin-1-yl)piperidine-1-carboxamide |
| 52A | CH | N | H | H | isopropyl | (+)-N-[5-cyano-3-(2-ethoxypyridin-3-yl)-2-oxo-1-(phenylsulphonyl)-2,3-dihydro-1H-indol-3-yl]-4-(4-isopropylpiperazin-1-yl)piperidine-1-carboxamide |
| 52B | CH | N | H | H | isopropyl | (−)-N-[5-cyano-3-(2-ethoxypyridin-3-yl)-2-oxo-1-(phenylsulphonyl)-2,3-dihydro-1H-indol-3-yl]-4-(4-isopropylpiperazin-1-yl)piperidine-1-carboxamide |
| 53 | CH | N | H | methoxy | isopropyl | (±)-N-{5-cyano-3-(2-ethoxypyridin-3-yl)-1-[(4-methoxyphenyl)sulphonyl]-2-oxo-2,3-dihydro-1H-indol-3-yl}-4-(4-isopropylpiperazin-1-yl)piperidine-1-carboxamide |
| 53A | CH | N | H | methoxy | isopropyl | (+)-N-{5-cyano-3-(2-ethoxypyridin-3-yl)-1-[(4-methoxyphenyl)sulphonyl]-2-oxo-2,3-dihydro-1H-indol-3-yl}-4-(4-isopropylpiperazin-1-yl)piperidine-1-carboxamide |
| 53B | CH | N | H | methoxy | isopropyl | (−)-N-{5-cyano-3-(2-ethoxypyridin-3-yl)-1-[(4-methoxyphenyl)sulphonyl]-2-oxo-2,3-dihydro-1H-indol-3-yl}-4-(4-isopropylpiperazin-1-yl)piperidine-1-carboxamide |
| 54 | CH | N | ethoxy | methoxy | isopropyl | (±)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(4-isopropylpiperazin-1-yl)piperidine-1-carboxamide |
| 54A | CH | N | ethoxy | methoxy | isopropyl | (+)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(4-isopropylpiperazin-1-yl)piperidine-1-carboxamide |
| 54B | CH | N | ethoxy | methoxy | isopropyl | (−)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(4-isopropylpiperazin-1-yl)piperidine-1-carboxamide |
| 55 | CH | N | methoxy | methoxy | H | (±)-N-[5-cyano-1-[(2,4-dimethoxyphenyl)sulphonyl]-3-(2-ethoxypyridin-3-yl)-2-oxo-2,3-dihydro-1H-indol-3-yl]-4-piperazin-1-ylpiperidine-1-carboxamide |
| 55A | CH | N | methoxy | methoxy | H | (+)-N-[5-cyano-1-[(2,4-dimethoxyphenyl)sulphonyl]-3-(2-ethoxypyridin-3-yl)-2-oxo-2,3-dihydro-1H-indol-3-yl]-4-piperazin-1-ylpiperidine-1-carboxamide |
| 55B | CH | N | methoxy | methoxy | H | (−)-N-[5-cyano-1-[(2,4-dimethoxyphenyl)sulphonyl]-3-(2-ethoxypyridin-3-yl)-2-oxo-2,3-dihydro-1H-indol-3-yl]-4-piperazin-1-ylpiperidine-1-carboxamide |
| 56 | CH | N | methoxy | H | H | (±)-N-{5-cyano-3-(2-ethoxypyridin-3-yl)-1-[(2-methoxyphenyl)sulphonyl]-2-oxo-2,3-dihydro-1H-indol-3-yl}-4-piperazin-1-ylpiperidine-1-carboxamide |
| 56A | CH | N | methoxy | H | H | (+)-N-{5-cyano-3-(2-ethoxypyridin-3-yl)-1-[(2-methoxyphenyl)sulphonyl]-2-oxo-2,3-dihydro-1H-indol-3-yl}-4-piperazin-1-ylpiperidine-1-carboxamide |
| 56B | CH | N | methoxy | H | H | (−)-N-{5-cyano-3-(2-ethoxypyridin-3-yl)-1-[(2-methoxyphenyl)sulphonyl]-2-oxo-2,3-dihydro-1H-indol-3-yl}-4-piperazin-1-ylpiperidine-1-carboxamide |
| 57 | CH | N | ethoxy | H | H | (±)-N-[5-cyano-1-[(2-ethoxyphenyl)sulphonyl]-3-(2-ethoxypyridin-3-yl)-2-oxo-2,3-dihydro-1H-indol-3-yl]-4-piperazin-1-ylpiperidine-1-carboxamide |
| 57A | CH | N | ethoxy | H | H | (+)-N-[5-cyano-1-[(2-ethoxyphenyl)sulphonyl]-3-(2-ethoxypyridin-3-yl)-2-oxo-2,3-dihydro-1H-indol-3-yl]-4-piperazin-1-ylpiperidine-1-carboxamide |
| 57B | CH | N | ethoxy | H | H | (−)-N-[5-cyano-1-[(2-ethoxyphenyl)sulphonyl]-3-(2-ethoxypyridin-3-yl)-2-oxo-2,3-dihydro-1H-indol-3-yl]-4-piperazin-1-ylpiperidine-1-carboxamide |
| 58 | CH | N | H | H | H | (±)-N-[5-cyano-3-(2-ethoxypyridin-3-yl)-2-oxo-1-(phenylsulphonyl)-2,3-dihydro-1H-indol-3-yl]-4-piperazin-1-ylpiperidine-1-carboxamide |
| 58A | CH | N | H | H | H | (+)-N-[5-cyano-3-(2-ethoxypyridin-3-yl)-2-oxo-1-(phenylsulphonyl)-2,3-dihydro-1H-indol-3-yl]-4-piperazin-1-ylpiperidine-1-carboxamide |
| 58B | CH | N | H | H | H | (−)-N-[5-cyano-3-(2-ethoxypyridin-3-yl)-2-oxo-1-(phenylsulphonyl)-2,3-dihydro-1H-indol-3-yl]-4-piperazin-1-ylpiperidine-1-carboxamide |
| 59 | CH | N | H | methoxy | H | (±)-N-{5-cyano-3-(2-ethoxypyridin-3-yl)-1-[(4-methoxyphenyl)sulphonyl]-2-oxo-2,3-dihydro-1H-indol-3-yl}-4-piperazin-1-ylpiperidine-1-carboxamide |
| 59A | CH | N | H | methoxy | H | (+)-N-{5-cyano-3-(2-ethoxypyridin-3-yl)-1-[(4-methoxyphenyl)sulphonyl]-2-oxo-2,3-dihydro-1H-indol-3-yl}-4-piperazin-1-ylpiperidine-1-carboxamide |
| 59B | CH | N | H | methoxy | H | (−)-N-{5-cyano-3-(2-ethoxypyridin-3-yl)-1-[(4-methoxyphenyl)sulphonyl]-2-oxo-2,3-dihydro-1H-indol-3-yl}-4-piperazin-1-ylpiperidine-1-carboxamide |
| 60 | CH | N | ethoxy | methoxy | H | (±)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-piperazin-1-ylpiperidine-1-carboxamide |
| 60A | CH | N | ethoxy | methoxy | H | (+)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-piperazin-1-ylpiperidine-1-carboxamide |
| 60B | CH | N | ethoxy | methoxy | H | (−)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4-piperazin-1-ylpiperidine-1-carboxamide |
| 61 | CH | CH | methoxy | methoxy | methyl | (±)-N-[5-cyano-1-[(2,4-dimethoxyphenyl)sulphonyl]-3-(2-ethoxypyridin-3-yl)-2-oxo-2,3-dihydro-1H-indol-3-yl]-1'-methyl-4,4'-bipiperidine-1-carboxamide |
| 61A | CH | CH | methoxy | methoxy | methyl | (+)-N-[5-cyano-1-[(2,4-dimethoxyphenyl)sulphonyl]-3-(2-ethoxypyridin-3-yl)-2-oxo-2,3-dihydro-1H-indol-3-yl]-1'-methyl-4,4'-bipiperidine-1-carboxamide |
| 61B | CH | CH | methoxy | methoxy | methyl | (−)-N-[5-cyano-1-[(2,4-dimethoxyphenyl)sulphonyl]-3-(2-ethoxypyridin-3-yl)-2-oxo-2,3-dihydro-1H-indol-3-yl]-1'-methyl-4,4'-bipiperidine-1-carboxamide |
| 62 | CH | CH | methoxy | H | methyl | (±)-N-{5-cyano-3-(2-ethoxypyridin-3-yl)-1-[(2-methoxyphenyl)sulphonyl]-2-oxo-2,3-dihydro-1H-indol-3-yl}-1'-methyl-4,4'-bipiperidine-1-carboxamide |
| 62A | CH | CH | methoxy | H | methyl | (+)-N-{5-cyano-3-(2-ethoxypyridin-3-yl)-1-[(2-methoxyphenyl)sulphonyl]-2-oxo-2,3-dihydro-1H-indol-3-yl}-1'-methyl-4,4'-bipiperidine-1-carboxamide |
| 62B | CH | CH | methoxy | H | methyl | (−)-N-{5-cyano-3-(2-ethoxypyridin-3-yl)-1-[(2-methoxyphenyl)sulphonyl]-2-oxo-2,3-dihydro-1H-indol-3-yl}-1'-methyl-4,4'-bipiperidine-1-carboxamide |
| 63 | CH | CH | ethoxy | H | methyl | (±)-N-[5-cyano-1-[(2-ethoxyphenyl)sulphonyl]-3-(2-ethoxypyridin-3-yl)-2-oxo-2,3-dihydro-1H-indol-3-yl]-1'-methyl-4,4'-bipiperidine-1-carboxamide |

TABLE 2-continued

Compounds of the general formula (Ib) where the radicals R5, R6, R7, X2 and X3 have the meanings mentioned below (in each case per row):

| Exp. No. | X2 | X3 | R5 | R6 | R7 | IUPAC Name (according to ACD-Labs Version 8.00 release product version 8.05) |
|---|---|---|---|---|---|---|
| 63A | CH | CH | ethoxy | H | methyl | (+)-N-[5-cyano-1-[(2-ethoxyphenyl)sulphonyl]-3-(2-ethoxypyridin-3-yl)-2-oxo-2,3-dihydro-1H-indol-3-yl]-1'-methyl-4,4'-bipiperidine-1-carboxamide |
| 63B | CH | CH | ethoxy | H | methyl | (−)-N-[5-cyano-1-[(2-ethoxyphenyl)sulphonyl]-3-(2-ethoxypyridin-3-yl)-2-oxo-2,3-dihydro-1H-indol-3-yl]-1'-methyl-4,4'-bipiperidine-1-carboxamide |
| 64 | CH | CH | H | H | methyl | (±)-N-[5-cyano-3-(2-ethoxypyridin-3-yl)-2-oxo-1-(phenylsulphonyl)-2,3-dihydro-1H-indol-3-yl]-1'-methyl-4,4'-bipiperidine-1-carboxamide |
| 64A | CH | CH | H | H | methyl | (+)-N-[5-cyano-3-(2-ethoxypyridin-3-yl)-2-oxo-1-(phenylsulphonyl)-2,3-dihydro-1H-indol-3-yl]-1'-methyl-4,4'-bipiperidine-1-carboxamide |
| 64B | CH | CH | H | H | methyl | (−)-N-[5-cyano-3-(2-ethoxypyridin-3-yl)-2-oxo-1-(phenylsulphonyl)-2,3-dihydro-1H-indol-3-yl]-1'-methyl-4,4'-bipiperidine-1-carboxamide |
| 65 | CH | CH | H | methoxy | methyl | (±)-N-{5-cyano-3-(2-ethoxypyridin-3-yl)-1-[(4-methoxyphenyl)sulphonyl]-2-oxo-2,3-dihydro-1H-indol-3-yl}-1'-methyl-4,4'-bipiperidine-1-carboxamide |
| 65A | CH | CH | H | methoxy | methyl | (+)-N-{5-cyano-3-(2-ethoxypyridin-3-yl)-1-[(4-methoxyphenyl)sulphonyl]-2-oxo-2,3-dihydro-1H-indol-3-yl}-1'-methyl-4,4'-bipiperidine-1-carboxamide |
| 65B | CH | CH | H | methoxy | methyl | (−)-N-{5-cyano-3-(2-ethoxypyridin-3-yl)-1-[(4-methoxyphenyl)sulphonyl]-2-oxo-2,3-dihydro-1H-indol-3-yl}-1'-methyl-4,4'-bipiperidine-1-carboxamide |
| 66 | CH | CH | ethoxy | methoxy | methyl | (±)-N-[5-cyano-1-[(2-ethoxy-4-methoxyphenyl)sulphonyl]-3-(2-ethoxypyridin-3-yl)-2-oxo-2,3-dihydro-1H-indol-3-yl]-1'-methyl-4,4'-bipiperidine-1-carboxamide |
| 66A | CH | CH | ethoxy | methoxy | methyl | (+)-N-[5-cyano-1-[(2-ethoxy-4-methoxyphenyl)sulphonyl]-3-(2-ethoxypyridin-3-yl)-2-oxo-2,3-dihydro-1H-indol-3-yl]-1'-methyl-4,4'-bipiperidine-1-carboxamide |
| 66B | CH | CH | ethoxy | methoxy | methyl | (−)-N-[5-cyano-1-[(2-ethoxy-4-methoxyphenyl)sulphonyl]-3-(2-ethoxypyridin-3-yl)-2-oxo-2,3-dihydro-1H-indol-3-yl]-1'-methyl-4,4'-bipiperidine-1-carboxamide |
| 67 | CH | CH | methoxy | methoxy | ethyl | (±)-N-[5-cyano-1-[(2,4-dimethoxyphenyl)sulphonyl]-3-(2-ethoxypyridin-3-yl)-2-oxo-2,3-dihydro-1H-indol-3-yl]-1'-ethyl-4,4'-bipiperidine-1-carboxamide |
| 67A | CH | CH | methoxy | methoxy | ethyl | (+)-N-[5-cyano-1-[(2,4-dimethoxyphenyl)sulphonyl]-3-(2-ethoxypyridin-3-yl)-2-oxo-2,3-dihydro-1H-indol-3-yl]-1'-ethyl-4,4'-bipiperidine-1-carboxamide |
| 67B | CH | CH | methoxy | methoxy | ethyl | (−)-N-[5-cyano-1-[(2,4-dimethoxyphenyl)sulphonyl]-3-(2-ethoxypyridin-3-yl)-2-oxo-2,3-dihydro-1H-indol-3-yl]-1'-ethyl-4,4'-bipiperidine-1-carboxamide |
| 68 | CH | CH | methoxy | H | ethyl | (±)-N-{5-cyano-3-(2-ethoxypyridin-3-yl)-1-[(2-methoxyphenyl)sulphonyl]-2-oxo-2,3-dihydro-1H-indol-3-yl}-1'-ethyl-4,4'-bipiperidine-1-carboxamide |
| 68A | CH | CH | methoxy | H | ethyl | (+)-N-{5-cyano-3-(2-ethoxypyridin-3-yl)-1-[(2-methoxyphenyl)sulphonyl]-2-oxo-2,3-dihydro-1H-indol-3-yl}-1'-ethyl-4,4'-bipiperidine-1-carboxamide |
| 68B | CH | CH | methoxy | H | ethyl | (−)-N-{5-cyano-3-(2-ethoxypyridin-3-yl)-1-[(2-methoxyphenyl)sulphonyl]-2-oxo-2,3-dihydro-1H-indol-3-yl}-1'-ethyl-4,4'-bipiperidine-1-carboxamide |
| 69 | CH | CH | ethoxy | H | ethyl | (±)-N-[5-cyano-1-[(2-ethoxyphenyl)sulphonyl]-3-(2-ethoxypyridin-3-yl)-2-oxo-2,3-dihydro-1H-indol-3-yl]-1'-ethyl-4,4'-bipiperidine-1-carboxamide |
| 69A | CH | CH | ethoxy | H | ethyl | (+)-N-[5-cyano-1-[(2-ethoxyphenyl)sulphonyl]-3-(2-ethoxypyridin-3-yl)-2-oxo-2,3-dihydro-1H-indol-3-yl]-1'-ethyl-4,4'-bipiperidine-1-carboxamide |
| 69B | CH | CH | ethoxy | H | ethyl | (−)-N-[5-cyano-1-[(2-ethoxyphenyl)sulphonyl]-3-(2-ethoxypyridin-3-yl)-2-oxo-2,3-dihydro-1H-indol-3-yl]-1'-ethyl-4,4'-bipiperidine-1-carboxamide |
| 70 | CH | CH | H | H | ethyl | (±)-N-[5-cyano-3-(2-ethoxypyridin-3-yl)-2-oxo-1-(phenylsulphonyl)-2,3-dihydro-1H-indol-3-yl]-1'-ethyl-4,4'-bipiperidine-1-carboxamide |
| 70A | CH | CH | H | H | ethyl | (+)-N-[5-cyano-3-(2-ethoxypyridin-3-yl)-2-oxo-1-(phenylsulphonyl)-2,3-dihydro-1H-indol-3-yl]-1'-ethyl-4,4'-bipiperidine-1-carboxamide |
| 70B | CH | CH | H | H | ethyl | (−)-N-[5-cyano-3-(2-ethoxypyridin-3-yl)-2-oxo-1-(phenylsulphonyl)-2,3-dihydro-1H-indol-3-yl]-1'-ethyl-4,4'-bipiperidine-1-carboxamide |
| 71 | CH | CH | H | methoxy | ethyl | (±)-N-{5-cyano-3-(2-ethoxypyridin-3-yl)-1-[(4-methoxyphenyl)sulphonyl]-2-oxo-2,3-dihydro-1H-indol-3-yl}-1'-ethyl-4,4'-bipiperidine-1-carboxamide |
| 71A | CH | CH | H | methoxy | ethyl | (+)-N-{5-cyano-3-(2-ethoxypyridin-3-yl)-1-[(4-methoxyphenyl)sulphonyl]-2-oxo-2,3-dihydro-1H-indol-3-yl}-1'-ethyl-4,4'-bipiperidine-1-carboxamide |
| 71B | CH | CH | H | methoxy | ethyl | (−)-N-{5-cyano-3-(2-ethoxypyridin-3-yl)-1-[(4-methoxyphenyl)sulphonyl]-2-oxo-2,3-dihydro-1H-indol-3-yl}-1'-ethyl-4,4'-bipiperidine-1-carboxamide |
| 72 | CH | CH | ethoxy | methoxy | ethyl | (±)-N-[5-cyano-1-[(2-ethoxy-4-methoxyphenyl)sulphonyl]-3-(2-ethoxypyridin-3-yl)-2-oxo-2,3-dihydro-1H-indol-3-yl]-1'-ethyl-4,4'-bipiperidine-1-carboxamide |
| 72A | CH | CH | ethoxy | methoxy | ethyl | (+)-N-[5-cyano-1-[(2-ethoxy-4-methoxyphenyl)sulphonyl]-3-(2-ethoxypyridin-3-yl)-2-oxo-2,3-dihydro-1H-indol-3-yl]-1'-ethyl-4,4'-bipiperidine-1-carboxamide |
| 72B | CH | CH | ethoxy | methoxy | ethyl | (−)-N-[5-cyano-1-[(2-ethoxy-4-methoxyphenyl)sulphonyl]-3-(2-ethoxypyridin-3-yl)-2-oxo-2,3-dihydro-1H-indol-3-yl]-1'-ethyl-4,4'-bipiperidine-1-carboxamide |
| 73 | CH | CH | methoxy | methoxy | n-propyl | (±)-N-[5-cyano-1-[(2,4-dimethoxyphenyl)sulphonyl]-3-(2-ethoxypyridin-3-yl)-2-oxo-2,3-dihydro-1H-indol-3-yl]-1'-propyl-4,4'-bipiperidine-1-carboxamide |
| 73A | CH | CH | methoxy | methoxy | n-propyl | (+)-N-[5-cyano-1-[(2,4-dimethoxyphenyl)sulphonyl]-3-(2-ethoxypyridin-3-yl)-2-oxo-2,3-dihydro-1H-indol-3-yl]-1'-propyl-4,4'-bipiperidine-1-carboxamide |
| 73B | CH | CH | methoxy | methoxy | n-propyl | (−)-N-[5-cyano-1-[(2,4-dimethoxyphenyl)sulphonyl]-3-(2-ethoxypyridin-3-yl)-2-oxo-2,3-dihydro-1H-indol-3-yl]-1'-propyl-4,4'-bipiperidine-1-carboxamide |
| 74 | CH | CH | methoxy | H | n-propyl | (±)-N-{5-cyano-3-(2-ethoxypyridin-3-yl)-1-[(2-methoxyphenyl)sulphonyl]-2-oxo-2,3-dihydro-1H-indol-3-yl}-1'-propyl-4,4'-bipiperidine-1-carboxamide |
| 74A | CH | CH | methoxy | H | n-propyl | (+)-N-{5-cyano-3-(2-ethoxypyridin-3-yl)-1-[(2-methoxyphenyl)sulphonyl]-2-oxo-2,3-dihydro-1H-indol-3-yl}-1'-propyl-4,4'-bipiperidine-1-carboxamide |
| 74B | CH | CH | methoxy | H | n-propyl | (−)-N-{5-cyano-3-(2-ethoxypyridin-3-yl)-1-[(2-methoxyphenyl)sulphonyl]-2-oxo-2,3-dihydro-1H-indol-3-yl}-1'-propyl-4,4'-bipiperidine-1-carboxamide |
| 75 | CH | CH | ethoxy | H | n-propyl | (±)-N-[5-cyano-1-[(2-ethoxyphenyl)sulphonyl]-3-(2-ethoxypyridin-3-yl)-2-oxo-2,3-dihydro-1H-indol-3-yl]-1'-propyl-4,4'-bipiperidine-1-carboxamide |
| 75A | CH | CH | ethoxy | H | n-propyl | (+)-N-[5-cyano-1-[(2-ethoxyphenyl)sulphonyl]-3-(2-ethoxypyridin-3-yl)-2-oxo-2,3-dihydro-1H-indol-3-yl]-1'-propyl-4,4'-bipiperidine-1-carboxamide |

TABLE 2-continued

Compounds of the general formula (Ib) where the radicals R5, R6, R7, X2 and X3 have the meanings mentioned below (in each case per row):

| Exp. No. | X2 | X3 | R5 | R6 | R7 | IUPAC Name (according to ACD-Labs Version 8.00 release product version 8.05) |
|---|---|---|---|---|---|---|
| 75B | CH | CH | ethoxy | H | n-propyl | (−)-N-[5-cyano-1-[(2-ethoxyphenyl)sulphonyl]-3-(2-ethoxypyridin-3-yl)-2-oxo-2,3-dihydro-1H-indol-3-yl]-1'-propyl-4,4'-bipiperidine-1-carboxamide |
| 76 | CH | CH | H | H | n-propyl | (±)-N-[5-cyano-3-(2-ethoxypyridin-3-yl)-2-oxo-1-(phenylsulphonyl)-2,3-dihydro-1H-indol-3-yl]-1'-propyl-4,4'-bipiperidine-1-carboxamide |
| 76A | CH | CH | H | H | n-propyl | (+)-N-[5-cyano-3-(2-ethoxypyridin-3-yl)-2-oxo-1-(phenylsulphonyl)-2,3-dihydro-1H-indol-3-yl]-1'-propyl-4,4'-bipiperidine-1-carboxamide |
| 76B | CH | CH | H | H | n-propyl | (−)-N-[5-cyano-3-(2-ethoxypyridin-3-yl)-2-oxo-1-(phenylsulphonyl)-2,3-dihydro-1H-indol-3-yl]-1'-propyl-4,4'-bipiperidine-1-carboxamide |
| 77 | CH | CH | H | methoxy | n-propyl | (±)-N-{5-cyano-3-(2-ethoxypyridin-3-yl)-1-[(4-methoxyphenyl)sulphonyl]-2-oxo-2,3-dihydro-1H-indol-3-yl}-1'-propyl-4,4'-bipiperidine-1-carboxamide |
| 77A | CH | CH | H | methoxy | n-propyl | (+)-N-{5-cyano-3-(2-ethoxypyridin-3-yl)-1-[(4-methoxyphenyl)sulphonyl]-2-oxo-2,3-dihydro-1H-indol-3-yl}-1'-propyl-4,4'-bipiperidine-1-carboxamide |
| 77B | CH | CH | H | methoxy | n-propyl | (−)-N-{5-cyano-3-(2-ethoxypyridin-3-yl)-1-[(4-methoxyphenyl)sulphonyl]-2-oxo-2,3-dihydro-1H-indol-3-yl}-1'-propyl-4,4'-bipiperidine-1-carboxamide |
| 78 | CH | CH | ethoxy | methoxy | n-propyl | (±)-N-[5-cyano-1-[(2-ethoxy-4-methoxyphenyl)sulphonyl]-3-(2-ethoxypyridin-3-yl)-2-oxo-2,3-dihydro-1H-indol-3-yl]-1'-propyl-4,4'-bipiperidine-1-carboxamide |
| 78A | CH | CH | ethoxy | methoxy | n-propyl | (+)-N-[5-cyano-1-[(2-ethoxy-4-methoxyphenyl)sulphonyl]-3-(2-ethoxypyridin-3-yl)-2-oxo-2,3-dihydro-1H-indol-3-yl]-1'-propyl-4,4'-bipiperidine-1-carboxamide |
| 78B | CH | CH | ethoxy | methoxy | n-propyl | (−)-N-[5-cyano-1-[(2-ethoxy-4-methoxyphenyl)sulphonyl]-3-(2-ethoxypyridin-3-yl)-2-oxo-2,3-dihydro-1H-indol-3-yl]-1'-propyl-4,4'-bipiperidine-1-carboxamide |
| 79 | CH | CH | methoxy | methoxy | isopropyl | (±)-N-[5-cyano-1-[(2,4-dimethoxyphenyl)sulphonyl]-3-(2-ethoxypyridin-3-yl)-2-oxo-2,3-dihydro-1H-indol-3-yl]-1'-isopropyl-4,4'-bipiperidine-1-carboxamide |
| 79A | CH | CH | methoxy | methoxy | isopropyl | (+)-N-[5-cyano-1-[(2,4-dimethoxyphenyl)sulphonyl]-3-(2-ethoxypyridin-3-yl)-2-oxo-2,3-dihydro-1H-indol-3-yl]-1'-isopropyl-4,4'-bipiperidine-1-carboxamide |
| 79B | CH | CH | methoxy | methoxy | isopropyl | (−)-N-[5-cyano-1-[(2,4-dimethoxyphenyl)sulphonyl]-3-(2-ethoxypyridin-3-yl)-2-oxo-2,3-dihydro-1H-indol-3-yl]-1'-isopropyl-4,4'-bipiperidine-1-carboxamide |
| 80 | CH | CH | methoxy | H | isopropyl | (±)-N-{5-cyano-3-(2-ethoxypyridin-3-yl)-1-[(2-methoxyphenyl)sulphonyl]-2-oxo-2,3-dihydro-1H-indol-3-yl}-1'-isopropyl-4,4'-bipiperidine-1-carboxamide |
| 80A | CH | CH | methoxy | H | isopropyl | (+)-N-{5-cyano-3-(2-ethoxypyridin-3-yl)-1-[(2-methoxyphenyl)sulphonyl]-2-oxo-2,3-dihydro-1H-indol-3-yl}-1'-isopropyl-4,4'-bipiperidine-1-carboxamide |
| 80B | CH | CH | methoxy | H | isopropyl | (−)-N-{5-cyano-3-(2-ethoxypyridin-3-yl)-1-[(2-methoxyphenyl)sulphonyl]-2-oxo-2,3-dihydro-1H-indol-3-yl}-1'-isopropyl-4,4'-bipiperidine-1-carboxamide |
| 81 | CH | CH | ethoxy | H | isopropyl | (±)-N-[5-cyano-1-[(2-ethoxyphenyl)sulphonyl]-3-(2-ethoxypyridin-3-yl)-2-oxo-2,3-dihydro-1H-indol-3-yl]-1'-isopropyl-4,4'-bipiperidine-1-carboxamide |
| 81A | CH | CH | ethoxy | H | isopropyl | (+)-N-[5-cyano-1-[(2-ethoxyphenyl)sulphonyl]-3-(2-ethoxypyridin-3-yl)-2-oxo-2,3-dihydro-1H-indol-3-yl]-1'-isopropyl-4,4'-bipiperidine-1-carboxamide |
| 81B | CH | CH | ethoxy | H | isopropyl | (−)-N-[5-cyano-1-[(2-ethoxyphenyl)sulphonyl]-3-(2-ethoxypyridin-3-yl)-2-oxo-2,3-dihydro-1H-indol-3-yl]-1'-isopropyl-4,4'-bipiperidine-1-carboxamide |
| 82 | CH | CH | H | H | isopropyl | (±)-N-[5-cyano-3-(2-ethoxypyridin-3-yl)-2-oxo-1-(phenylsulphonyl)-2,3-dihydro-1H-indol-3-yl]-1'-isopropyl-4,4'-bipiperidine-1-carboxamide |
| 82A | CH | CH | H | H | isopropyl | (+)-N-[5-cyano-3-(2-ethoxypyridin-3-yl)-2-oxo-1-(phenylsulphonyl)-2,3-dihydro-1H-indol-3-yl]-1'-isopropyl-4,4'-bipiperidine-1-carboxamide |
| 82B | CH | CH | H | H | isopropyl | (−)-N-[5-cyano-3-(2-ethoxypyridin-3-yl)-2-oxo-1-(phenylsulphonyl)-2,3-dihydro-1H-indol-3-yl]-1'-isopropyl-4,4'-bipiperidine-1-carboxamide |
| 83 | CH | CH | H | methoxy | isopropyl | (±)-N-{5-cyano-3-(2-ethoxypyridin-3-yl)-1-[(4-methoxyphenyl)sulphonyl]-2-oxo-2,3-dihydro-1H-indol-3-yl}-1'-isopropyl-4,4'-bipiperidine-1-carboxamide |
| 83A | CH | CH | H | methoxy | isopropyl | (+)-N-{5-cyano-3-(2-ethoxypyridin-3-yl)-1-[(4-methoxyphenyl)sulphonyl]-2-oxo-2,3-dihydro-1H-indol-3-yl}-1'-isopropyl-4,4'-bipiperidine-1-carboxamide |
| 83B | CH | CH | H | methoxy | isopropyl | (−)-N-{5-cyano-3-(2-ethoxypyridin-3-yl)-1-[(4-methoxyphenyl)sulphonyl]-2-oxo-2,3-dihydro-1H-indol-3-yl}-1'-isopropyl-4,4'-bipiperidine-1-carboxamide |
| 84 | CH | CH | ethoxy | methoxy | isopropyl | (±)-N-[5-cyano-1-[(2-ethoxy-4-methoxyphenyl)sulphonyl]-3-(2-ethoxypyridin-3-yl)-2-oxo-2,3-dihydro-1H-indol-3-yl]-1'-isopropyl-4,4'-bipiperidine-1-carboxamide |
| 84A | CH | CH | ethoxy | methoxy | isopropyl | (+)-N-[5-cyano-1-[(2-ethoxy-4-methoxyphenyl)sulphonyl]-3-(2-ethoxypyridin-3-yl)-2-oxo-2,3-dihydro-1H-indol-3-yl]-1'-isopropyl-4,4'-bipiperidine-1-carboxamide |
| 84B | CH | CH | ethoxy | methoxy | isopropyl | (−)-N-[5-cyano-1-[(2-ethoxy-4-methoxyphenyl)sulphonyl]-3-(2-ethoxypyridin-3-yl)-2-oxo-2,3-dihydro-1H-indol-3-yl]-1'-isopropyl-4,4'-bipiperidine-1-carboxamide |
| 85 | CH | CH | methoxy | methoxy | H | (±)-N-[5-cyano-1-[(2,4-dimethoxyphenyl)sulphonyl]-3-(2-ethoxypyridin-3-yl)-2-oxo-2,3-dihydro-1H-indol-3-yl]-4,4'-bipiperidine-1-carboxamide |
| 85A | CH | CH | methoxy | methoxy | H | (+)-N-[5-cyano-1-[(2,4-dimethoxyphenyl)sulphonyl]-3-(2-ethoxypyridin-3-yl)-2-oxo-2,3-dihydro-1H-indol-3-yl]-4,4'-bipiperidine-1-carboxamide |
| 85B | CH | CH | methoxy | methoxy | H | (−)-N-[5-cyano-1-[(2,4-dimethoxyphenyl)sulphonyl]-3-(2-ethoxypyridin-3-yl)-2-oxo-2,3-dihydro-1H-indol-3-yl]-4,4'-bipiperidine-1-carboxamide |
| 86 | CH | CH | methoxy | H | H | (±)-N-{5-cyano-3-(2-ethoxypyridin-3-yl)-1-[(2-methoxyphenyl)sulphonyl]-2-oxo-2,3-dihydro-1H-indol-3-yl}-4,4'-bipiperidine-1-carboxamide |
| 86A | CH | CH | methoxy | H | H | (+)-N-{5-cyano-3-(2-ethoxypyridin-3-yl)-1-[(2-methoxyphenyl)sulphonyl]-2-oxo-2,3-dihydro-1H-indol-3-yl}-4,4'-bipiperidine-1-carboxamide |
| 86B | CH | CH | methoxy | H | H | (−)-N-{5-cyano-3-(2-ethoxypyridin-3-yl)-1-[(2-methoxyphenyl)sulphonyl]-2-oxo-2,3-dihydro-1H-indol-3-yl}-4,4'-bipiperidine-1-carboxamide |
| 87 | CH | CH | ethoxy | H | H | (±)-N-[5-cyano-1-[(2-ethoxyphenyl)sulphonyl]-3-(2-ethoxypyridin-3-yl)-2-oxo-2,3-dihydro-1H-indol-3-yl]-4,4'-bipiperidine-1-carboxamide |
| 87A | CH | CH | ethoxy | H | H | (+)-N-[5-cyano-1-[(2-ethoxyphenyl)sulphonyl]-3-(2-ethoxypyridin-3-yl)-2-oxo-2,3-dihydro-1H-indol-3-yl]-4,4'-bipiperidine-1-carboxamide |
| 87B | CH | CH | ethoxy | H | H | (−)-N-[5-cyano-1-[(2-ethoxyphenyl)sulphonyl]-3-(2-ethoxypyridin-3-yl)-2-oxo-2,3-dihydro-1H-indol-3-yl]-4,4'-bipiperidine-1-carboxamide |

TABLE 2-continued

Compounds of the general formula (Ib) where the radicals R5, R6, R7, X2 and X3 have the meanings mentioned below (in each case per row):

| Exp. No. | X2 | X3 | R5 | R6 | R7 | IUPAC Name (according to ACD-Labs Version 8.00 release product version 8.05) |
|---|---|---|---|---|---|---|
| 88 | CH | CH | H | H | H | (±)-N-[5-cyano-3-(2-ethoxypyridin-3-yl)-2-oxo-1-(phenylsulphonyl)-2,3-dihydro-1H-indol-3-yl]-4,4'-bipiperidine-1-carboxamide |
| 88A | CH | CH | H | H | H | (+)-N-[5-cyano-3-(2-ethoxypyridin-3-yl)-2-oxo-1-(phenylsulphonyl)-2,3-dihydro-1H-indol-3-yl]-4,4'-bipiperidine-1-carboxamide |
| 88B | CH | CH | H | H | H | (−)-N-[5-cyano-3-(2-ethoxypyridin-3-yl)-2-oxo-1-(phenylsulphonyl)-2,3-dihydro-1H-indol-3-yl]-4,4'-bipiperidine-1-carboxamide |
| 89 | CH | CH | H | methoxy | H | (±)-N-{5-cyano-3-(2-ethoxypyridin-3-yl)-1-[(4-methoxyphenyl)sulphonyl]-2-oxo-2,3-dihydro-1H-indol-3-yl}-4,4'-bipiperidine-1-carboxamide |
| 89A | CH | CH | H | methoxy | H | (+)-N-{5-cyano-3-(2-ethoxypyridin-3-yl)-1-[(4-methoxyphenyl)sulphonyl]-2-oxo-2,3-dihydro-1H-indol-3-yl}-4,4'-bipiperidine-1-carboxamide |
| 89B | CH | CH | H | methoxy | H | (−)-N-{5-cyano-3-(2-ethoxypyridin-3-yl)-1-[(4-methoxyphenyl)sulphonyl]-2-oxo-2,3-dihydro-1H-indol-3-yl}-4,4'-bipiperidine-1-carboxamide |
| 90 | CH | CH | ethoxy | methoxy | H | (±)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4,4'-bipiperidine-1-carboxamide |
| 90A | CH | CH | ethoxy | methoxy | H | (+)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4,4'-bipiperidine-1-carboxamide |
| 90B | CH | CH | ethoxy | methoxy | H | (−)-N-[5-cyano-1-[(2-ethoxy-4-methoxyphenyl)sulphonyl]-3-(2-ethoxypyridin-3-yl)-2-oxo-2,3-dihydro-1H-indol-3-yl]-4,4'-bipiperidine-1-carboxamide |

Methods for Determining the Biological Activity
Vasopressin V1b receptor binding assay:
Substances:

The test substances were dissolved in a concentration of $10^{-2}$ M in DMSO and further diluted to $5 \times 10^{-4}$ M to $5 \times 10^{-9}$ M in DMSO. This series of DMSO predilutions was diluted 1:10 with assay buffer. The substance concentration was again diluted 1:5 in the assay mixture (2% DMSO in the mixture).

Membrane Preparation:

CHO-K1 cells with stably expressed human vasopressin V1b receptor (clone 3H2) were harvested and homogenized in 50 mM Tris-HCl and in the presence of protease inhibitors (Roche complete Mini #1836170) with a Polytron homogenizer at a medium setting for 2×10 seconds and subsequently centrifuged at 40 000×g for 1 h. The membrane pellet was again homogenized and centrifuged as described and then taken up in 50 mM Tris-HCl, pH 7.4, homogenized and stored in aliquots frozen in liquid nitrogen at −190° C.

Binding Assay:

The binding assay was carried out by a method based on that of Tahara et al. (Tahara A et al., Brit. J. Pharmacol. 125, 1463-1470 (1998)). The incubation buffer was: 50 mM Tris, 10 mM $MgCl_2$, 0.1% BSA, pH 7.4.

In the assay mixture (250 µl), membranes (50 µg/ml protein in incubation buffer) from CHO-K1 cells with stably expressed human V1b receptors (cell line hV1b_3H2-CHO) were incubated with 1.5 nM $^3$H-AVP (8-Arg-vasopressin, PerkinElmer #18479) in incubation buffer (50 mM Tris, 10 mM $MgCl_2$, 0.1% BSA, pH 7.4) (total binding) or additionally with increasing concentrations of test substance (displacement experiment). The nonspecific binding was determined with 1 µM AVP (Bachem #H1780). All determinations were carried out as triplicate determinations. After incubation (60 minutes at room temperature), the free radioligand was removed by vacuum filtration (Skatron cell harvester 7000) through Wathman GF/B glass fibre filter mats, and the filters were transferred into scintillation vials. The liquid scintillation measurement took place in a Tricarb model 2000 or 2200CA instrument (Packard). Conversion of the measured cpm into dpm was carried out with the aid of a standard quench series.

Evaluation:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^3$H-AVP for the recombinant human V1b receptors is 0.4 nM and was used to determine the Ki value.

The test reveals that compounds of the present invention generally have high affinities towards the V1b receptor which, expressed as $K_i$(h-V1b) values, are generally below 150 nM, in particular at most 50 nM and especially at most 10 nM. The results are given in table 3

Vasopressin V1a Receptor Binding Assay:
Substances:

The test substances were dissolved in a concentration of $10^{-2}$ M in DMSO. These DMSO solutions were further diluted in incubation buffer (50 mM Tris, 10 mM $MgCl_2$, 0.1% BSA, pH 7.4).

Membrane Preparation:

CHO-K1 cells with stably expressed human vasopressin V1a receptor (clone 5) were harvested and homogenized in 50 mM Tris-HCl and in the presence of protease inhibitors (Roche complete Mini #1836170) with a Polytron homogenizer at a medium setting for 2×10 seconds and subsequently centrifuged at 40 000×g for 1 h. The membrane pellet was again homogenized and centrifuged as described and then taken up in 50 mM Tris-HCl, pH 7.4, homogenized and stored in aliquots frozen in liquid nitrogen at −190° C.

Binding Assay:

The binding assay was carried out by a method based on that of Tahara et al. (Tahara A et al., Brit. J. Pharmacal. 125, 1463-1470 (1998)).

The incubation buffer was: 50 mM Tris, 10 mM $MgCl_2$, 0.1% BSA, pH 7.4.

In the assay mixture (250 µl), membranes (20 µg/ml protein in incubation buffer) from CHO-K1 cells with stably expressed human V1a receptors (cell line hV1a_5_CHO) were incubated with 0.04 nM $^{125}$I-AVP (8-Arg-vasopressin, NEX 128) in incubation buffer (50 mM Tris, 10 mM $MgCl_2$, 0.1% BSA, pH 7.4) (total binding) or additionally with increasing concentrations of test substance (displacement experiment). The nonspecific binding was determined with 1 µM AVP (Bachem #H1780). Triplicate determinations were carried out.

After incubation (60 minutes at room temperature), the free radioligand was removed by vacuum filtration (Skatron cell harvester 7000) through Wathman GF/B glass fibre filter mats, and the filters were transferred into scintillation vials.

The liquid scintillation measurement took place in a Tricarb model 2000 or 2200CA instrument (Packard). Conversion of the measured cpm into dpm was carried out with the aid of a standard quench series.

Evaluation:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^{125}$I-AVP for the recombinant hV1a receptors was determined in saturation experiments. A Kd of 1.33 nM was used to determine the Ki value.

The test reveals that compounds of the present invention generally have selectivity towards the V1b receptor in comparison with V1a receptor, which, expressed as $K_i$(h–V1a)/$K_i$(h–V1b) values generally exceed 10 and are frequently at least 15, in particular at least 50 and especially at least 100. The results are given in table 3.

Vasopressin V2 Receptor Binding Assay:

Substances:

The test substances were dissolved in a concentration of $10^{-2}$ M in DMSO. This DMSO solution was further diluted in incubation buffer (50 mM Tris, 10 mM MgCl$_2$, 0.1% BSA, pH 7.4).

Membrane Preparation:

CHO-K1 cells with stably expressed human vasopressin V2 receptor (clone 23) were harvested and homogenized in 50 mM Tris-HCl and in the presence of protease inhibitors (Roche complete Mini #1836170) with a Polytron homogenizer at a medium setting for 2×10 seconds and subsequently centrifuged at 40 000×g for 1 h. The membrane pellet was again homogenized and centrifuged as described and then taken up in 50 mM Tris-HCl, pH 7.4, homogenized and stored in aliquots frozen in liquid nitrogen at −190° C.

Binding Assay:

The binding assay was carried out by a method based on that of Tahara at al. (Tahara A et al., Brit. J. Pharmacol. 125, 1463-1470 (1998)).

The incubation buffer was: 50 mM Tris, 10 mM MgCl$_2$, 0.1% BSA, pH 7.4.

In the assay mixture (250 µl), membranes (50 µg/ml protein in incubation buffer) from CHO-K1 cells with stably expressed human V2 receptors (cell line hV2_23_CHO) were incubated with 1-2 nM $^3$H-AVP (8-Arg-vasopressin, PerkinElmer #18479) in incubation buffer (50 mM Tris, 10 mM MgCl$_2$, 0.1% BSA, pH 7.4) (total binding) or additionally with increasing concentrations of test substance (displacement experiment). The nonspecific binding was determined with 1 µM AVP (Sachem #H1780). Triplicate determinations were carried out.

After incubation (60 minutes at room temperature), the free radioligand was removed by vacuum filtration (Skatron cell harvester 7000) through Wathman GFlB glass fibre filter mats, and the filters were transferred into scintillation vials.

The liquid scintillation measurement took place in a Tricarb model 2000 or 2200CA instrument (Packard). Conversion of the measured cpm into dpm was carried out with the aid of a standard quench series.

Evaluation:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^3$H-AVP for the recombinant hV2 receptors is 2.4 nM and was used to determine the Ki value.

The test reveals that compounds of the present invention generally have selectivity towards the V1b receptor in comparison with V2 receptor, which, expressed as $K_i$(h–V2)/$K_i$(h–V1b) values generally exceed 10 and are frequently at least 15, in particular at least 25 and especially at least 50.

Oxytocin Receptor Binding Assay

Substances:

The substances were dissolved in a concentration of $10^{-2}$ M in DMSO and diluted with incubation buffer (50 mM Tris, 10 mM MgCl$_2$, 0.1% BSA, pH 7.4).

Cell Preparation:

Confluent HEK-293 cells with transiently expressing recombinant human oxytocin receptors were centrifuged at 750×g and at room temperature for 5 minutes. The residue was taken up in ice-cold lysis buffer (50 mM Tris-HCl, 10% glycerol, pH 7.4 and Roche Complete Protease Inhibitor) and subjected to an osmotic shock at 4° C. for 20 minutes. The lyzed cells were then centrifuged at 750×g and at 4° C. for 20 minutes, the residue was taken up in incubation buffer, and aliquots of $10^7$ cells/ml were prepared. The aliquots were frozen at −80° C. until used.

Binding Assay:

On the day of the experiment, the cells were thawed, diluted with incubation buffer and homogenized using a Multipette Combitip (Eppendorf, Hamburg). The reaction mixture of 0.250 ml was composed of 2 to 5×10$^4$ recombinant cells, 3-4 nM $^3$H-oxytocin (PerkinElmer, NET 858) in the presence of test substance (inhibition plot) or only incubation buffer (total binding). The nonspecific binding was determined with $10^{-6}$ M oxytocin (Bachem AG, H2510). Determinations in triplicate were set up. Bound and free radioligand were separated by filtration under vacuum with Whatman GF/B glass fibre filters using a Skatron cell harvester 7000. The bound radioactivity was determined by liquid scintillation measurement in a Tricarb beta counter, model 2000 or 2200CA (Packard).

Evaluation:

The binding parameters were calculated by nonlinear regression analysis (SAS), in analogy to the LIGAND program of Munson and Rodbard (Analytical Biochem 1980; 107: 220-239). The Kd of $^3$H-oxytocin for the recombinant hOT receptors is 7.6 nM and was used to determine the Ki value.

The test reveals that compounds of the present invention generally have selectivity towards the V1b receptor in comparison with Oxytocin receptor, which, expressed as $K_i$(h–OT)/$K_i$(h–V1b) values generally exceed 10 and are frequently at least 15, in particular at least 25 and especially at least 50. The results are given in table 3.

TABLE 3

| Example | $K_i$(h – V1b)* [nM] | $K_i$(h – V1a)/ $K_i$(h – V1b)* | $K_i$(h – OT)/ $K_i$(h – V1b)* |
|---|---|---|---|
| 1 | +++ | +++ | +++ |
| 1B | +++ | +++ | +++ |
| 2 | ++ | +++ | +++ |
| 3 | ++ | +++ | +++ |
| 4 | ++ | ++ | ++ |
| 7B | +++ | +++ | +++ |
| 25 | +++ | +++ | ++ |
| 31 | +++ | +++ | +++ |
| 31B | +++ | +++ | +++ |
| 32 | ++ | + | +++ |
| 35 | +++ | + | ++ |
| 37 | +++ | +++ | +++ |

TABLE 3-continued

| | | | |
|---|---|---|---|
| 37B | +++ | +++ | +++ |
| 40 | +++ | ++ | +++ |
| 40B | +++ | + | +++ |
| 43 | +++ | +++ | +++ |
| 55 | +++ | +++ | ++ |
| 61 | +++ | +++ | +++ |
| 61B | +++ | +++ | +++ |
| 67 | +++ | +++ | +++ |
| 67B | +++ | +++ | +++ |
| 85 | +++ | +++ | ++ |

| | $K_i$(h – V1b) | $K_i$(h – V1a)/ $K_i$(h – V1b) | $K_i$(h – OT)/ $K_i$(h – V1b) |
|---|---|---|---|
| + | >50-150 nM | 15-50 | 15-25 |
| ++ | 10-50 nM | >50-100 | >25-50 |
| +++ | <10 nM | >100 | >50 |

Determination of the Microsomal Half-Life:

The Metabolic Stability of the Compounds of the Invention was Determined in the Following assay.

The test substances are incubated in a concentration of 0.5 µM as follows:

0.5 µM test substance is preincubated together with liver microsomes of various species (rat, human or other species) (0.25 mg of microsomal protein/ml) in 0.05M potassium phosphate buffer pH 7.4 in microtitre plates at 37° C. for 5 min. The reaction is started by adding NADPH (1 mg/ml). 50 µl aliquots are taken after 0, 5, 10, 15, 20 and 30 min, and the reaction is stopped immediately with the same volume of acetonitrile and cooled down. The samples are frozen until analyzed. Using MSMS, the remaining concentration of undegraded test substance is determined. From the increase of the test substance signal/time unit curve, the half-life (T1/2) is determined, where the half-life of the test substance can be calculated, assuming first order kinetics, from the decrease in the concentration of the compound with time. The microsomal clearance (mCl) is calculated as mCl=ln2/T1/2/(content of microsomal protein in mg/ml)×1000 [ml/min/mg] (modified according to the literature references: Di, The Society for Biomoleculaur Screening, 2003, 453-462; Obach, DMD, 1999 vol 27. N 11, 1350-1359).

The test reveals that compounds of the present invention generally have a high metabolic stability, which result in human microsomal clearance values of generally at most 220 µl min$^{-1}$ mg$^{-1}$, frequently 120 µl min$^{-1}$ mg$^{-1}$ and in particular at most 60 µl min$^{-1}$ mg$^{-1}$. The results are given in table 4.

TABLE 4

| Example | Human Mikrosomal Clearance [µl min$^{-1}$ mg$^{-1}$] |
|---|---|
| 1 | +++ |
| 1B | +++ |
| 4 | +++ |
| 5 | +++ |
| 7B | +++ |
| 25 | +++ |
| 31 | ++ |
| 31B | +++ |
| 34 | +++ |
| 35 | ++ |
| 37 | ++ |
| 37B | +++ |
| 40 | ++ |
| 40B | ++ |
| 55 | ++ |
| 61B | +++ |
| 85 | ++ |

TABLE 4-continued

| Human Mikrosomal Clearance | |
|---|---|
| + | >120-220 µl min$^{-1}$ mg$^{-1}$ |
| ++ | 60-120 µl min$^{-1}$ mg$^{-1}$ |
| +++ | <60 µl min$^{-1}$ mg$^{-1}$ |

Determination of Plasma Protein Binding (PPB) by Equilibrium Dialysis:

150 µl of rat or human plasma, with 1 or 10 µM of test substance added, is pipetted onto one side of the 96-well dialysis chambers, 150 µl of PPS buffer are pipetted onto the other side. The chambers are separated by a dialysis membrane having a cut-off of 6-8000 dalton.

The 96-well dialysis chambers are covered and gently shaken overnight.

The next morning, 10 µl of plasma are removed and diluted with 90 µl of PPS buffer, and the protein is precipitated using 200 µl of acetonitrile. The precipitated protein is removed by centrifugation, and 100 µl of the supernatant are used for MSMS analysis. From the buffer side, 100 µl are removed for MSMS analysis. See also the following literature reference: Banker, Journal of Pharmaceutical Sciences Vol. 92, 5, 967-974, 2003.

Methods for the in Vitro Determination of Cytochrom P450 (CYP) Inhibition

Luminescence Substrates for 2C9 and 3A4:

0.4 mg/ml of human liver microsomes are preincubated for 10 minutes with the test substances to be tested (0-20 µM), the CYP specific substrates, in 0.05 M potassium phosphate buffer pH 7.4 at 37° C. The Cyp-specific substrate for CYP 2C9 is luciferin H, that for CYP 3A4 is luciferin BE. The reaction is started by addition of NADPH. After 30 min of incubation at RT, the luciferin detection reagent is added, and the resulting luminescence signal is measured (modified according to literature reference: Promega, Technical Bulletin P450-GLO™ Assays).

Midazolam CYP 3A4 Time-Dependent Inhibition

The test consists of 2 parts. In the first part, the test substance is preincubated with the liver microsomes (with NADPH)=preincubation, followed by addition of the substrate; in the second part, substrate and test substance are added simultaneously=coincubation.

Preincubation:

0.05 mg/ml of microsomal protein (human liver microsomes) are preincubated with 0-10 µM (or 50 µM) of test substance in 50 mM potassium phosphate buffer for 5 min. The reaction is started using NADPH. After 30 min, 4 µM of midazolam (final concentration) are added, and the mixture is incubated for a further 10 min. After 10 min, 75 µl of the reaction solution are removed and quenched with 150 µl of acetonitrile solution.

Coincubation:

0.05 mg/ml of microsomal protein (human liver microsomes), 4 µM midazolam (final concentration) and 0-10 µM (or 50 µM) of test substance are preincubated in 50 mM potassium phosphate buffer for 5 min. The reaction is started using NADPH. After 10 min, 75 µl of the reaction solution are removed and quenched with 150 µl of acetonitrile solution. The samples are frozen until analyzed by MSMS (modified according to literature references:

Obdach, Journal of Pharmacology & Experimental Therapeutics, Vol 316, 1, 336-348, 2006; Walsky, Drug Metabolism and Disposition Vol 32, 6, 647-660, 2004).

Method for Determining the Solubility in Water (in mg/ml)

The solubility in water of the compounds according to the invention can be determined, for example, according to the so-called "shake flask" method (according to ASTM International: E 1148-02, *Standard test methods for measurement of aqueous solubility, Book of Standards Volume* 11.05.). Here, an excess of the solid compound is added to a buffer solution having a certain pH (for example phosphate buffer pH 7.4) and the resulting mixture is shaken or stirred until the steady state has been reached (typically 24 or 48 hours, sometimes even up to 7 days). The undissolved solid is then removed by filtration or centrifugation, and the concentration of the dissolved compound is determined by UV spectroscopy or high-pressure liquid chromatography (HPLC) using an appropriate calibration curve.

The invention claimed is:
1. A compound of the general formula (I)

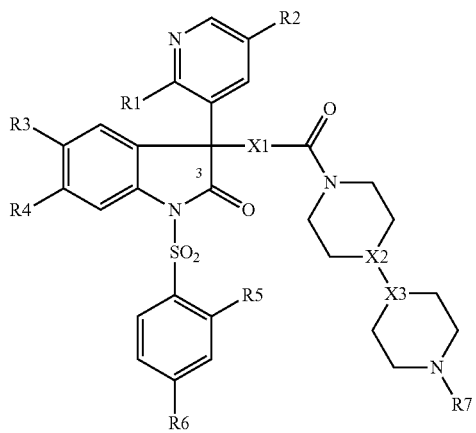

in which
R1 is ethoxy;
R2 is hydrogen;
R3 is cyano;
R4 is hydrogen;
R5 is hydrogen, methoxy or ethoxy;
R6 is hydrogen or methoxy;
R7 is hydrogen, methyl, ethyl, n-propyl or isopropyl;
X1 is —NH—;
X2 is N or CH;
X3 is N or CH;
where X2 and X3 are not simultaneously N;
and the pharmaceutically acceptable salts, and tautomeric forms thereof.

2. The compound according to claim 1, in which R5 is hydrogen or methoxy.

3. The compound according to claim 1, in which R7 is hydrogen, methyl or ethyl.

4. The compound according to claim 1, in which
R5 is hydrogen or methoxy;
R7 is hydrogen, methyl or ethyl;
X1 is —NH—;
X2 is N; and
X3 is CH.

5. The compound according to claim 1, in which
R5 is hydrogen or methoxy;
R7 is hydrogen, methyl or ethyl;
X1 is —NH—;
X2 is CH; and
X3 is N.

6. The compound according to claim 1, in which
R5 is methoxy;
R6 is methoxy
R7 is methyl or ethyl;
X1 is —NH—;
X2 is CH and X3 is N or
X2 is N and X3 is CH.

7. The compound according to claim 1, in which
R5 is methoxy;
R6 is methoxy;
R7 is methyl;
X1 is —NH—;
X2 is N; and
X3 is CH.

8. The compound according to claim 1, in which
R5 is methoxy;
R6 is methoxy;
R7 is methyl;
X1 is —NH—;
X2 is CH; and
X3 is N.

9. The compound according to claim 1, in which
R5 is methoxy;
R6 is methoxy;
R7 is ethyl;
X1 is —NH—;
X2 is CH; and
X3 is N.

10. The compound of the general formula (I) according to claim 1, present in optically active form as the (laevorotatory) (−)-enantiomer, which rotates the plane of polarization of linear polarized light to the left, and the pharmaceutically acceptable salts, and tautomeric forms thereof.

11. The compound of the general formula (I) according to claim 1, having formula (Ia),

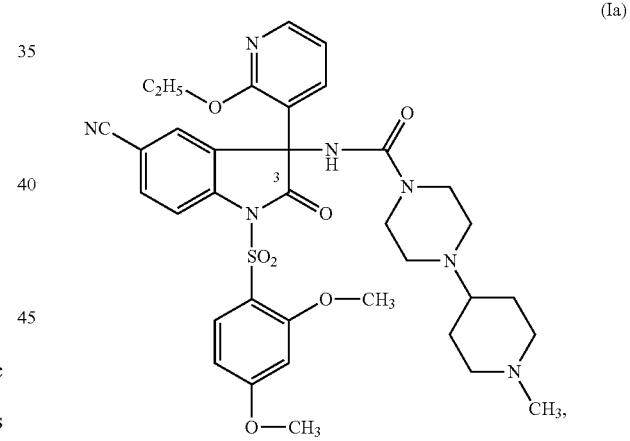

wherein the absolute configuration of the chiral C-3 ring carbon atom corresponds to the absolute configuration at C-3 of the (laevorotatory) (−)-enantiomer, which rotates the plane of polarization of linear polarized light to the left,
and the pharmaceutically acceptable salts, and tautomeric forms thereof.

12. The compound of the general formula (I) according to claim 10 in optically active form, characterized in that the corresponding laevorotatory (−)-enantiomer is present in an optical purity (enantiomeric excess, ee) of greater than 50%, and the pharmaceutically acceptable salts, and tautomeric forms thereof.

13. The compound of the general formula (I) according to claim 11 in optically active form, characterized in that the enantiomer having the preferred absolute configuration at the C-3 ring carbon atom is present in an optical purity (enantiomeric excess, ee) of greater than 50%, and the pharmaceutically acceptable salts, and tautomeric forms thereof.

14. The compound of the general formula (I) according to claim 10 in optically active form, characterized in that the corresponding laevorotatory (−)-enantiomer is present in an optical purity (enantiomeric excess, ee) of greater than 90%, and the pharmaceutically acceptable salts, and tautomeric forms thereof.

15. The compound of the general formula (I) according to claim 11 in optically active form, characterized in that the enantiomer having the preferred absolute configuration at the C-3 ring carbon atom is present in an optical purity (enantiomeric excess, ee) of greater than 90%, and the pharmaceutically acceptable salts, and tautomeric forms thereof.

16. The compound of the general formula (I) according to claim 1 in the form of the racemate, and the pharmaceutically acceptable salts, and tautomeric forms thereof.

17. A medicament, comprising at least one compound of the general formula (I) according to claim 1, or at least one pharmaceutically acceptable salt, or one tautomeric form thereof.

18. A process for preparing at least one compound of the general formula (I) according to claim 1, characterized by reaction of a compound of formula (IX) with an amine of formula (X),

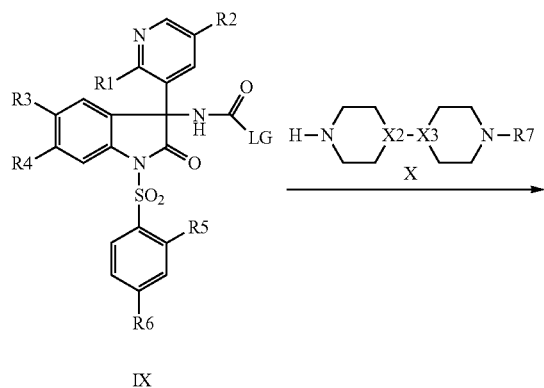

IX

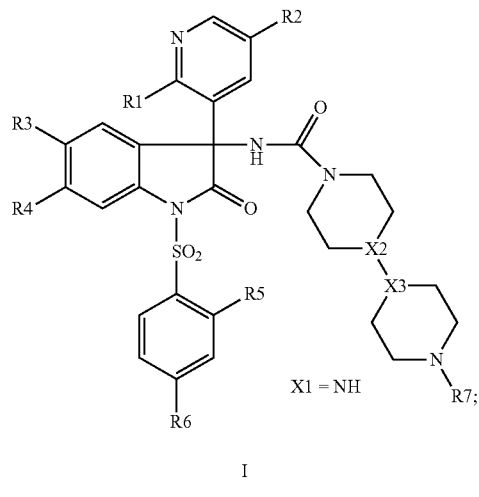

I or by deprotonation of a compound of formula (XII) with a strong base, followed by reaction with a sulphonyl chloride of formula (VII),

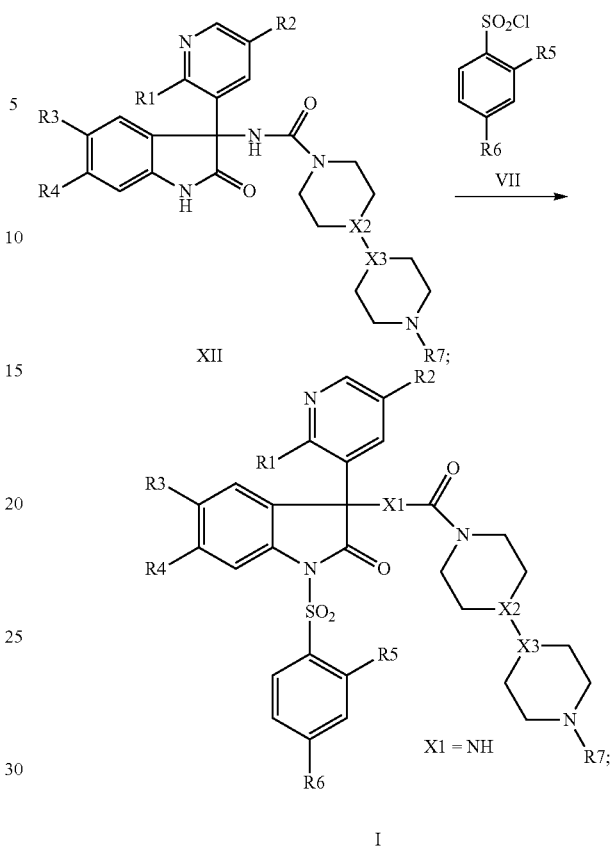

wherein
R1, R2, R3, R4, R5, R6, R7, X2, and X3 are as defined in claim 1,
X1 is —NH—, and
LG is a leaving group.

19. A compound selected from the group consisting of
N-[5-cyano-1 -[(2,4-dimethoxyphenyl)sulphonyl]-3-(2-ethoxypyridin-3-yl)-2-oxo-2,3-dihydro-1H-indol-3-yl]-4-(1-methylpiperidin-4-yl)piperazine-1-carboxamide;

N-{5-cyano-3-(2-ethoxypyridin-3-yl)-1-[(2-methoxyphenyl)sulphonyl]-2-oxo-2,3-dihydro-1H-indol-3-yl}-4-(1-methylpiperidin-4-yl)piperazine-1-carboxamide;

N-[5-cyano-1-[(2-ethoxyphenyl)sulphonyl]-3-(2-ethoxypyridin-3-yl)-2-oxo-2,3-dihydro-1H-indol-3-yl]-4-(1-methylpiperidin-4-yl)piperazine-1-carboxamide;

N-[5-cyano-3-(2-ethoxypyridin-3-yl)-2-oxo-1-(phenylsulphonyl)-2,3-dihydro-1H-indol-3-yl]-4-(1-methylpiperidin-4-yl)piperazine-1-carboxamide;

N-{5-cyano-3-(2-ethoxypyridin-3-yl)-1-[(4-methoxyphenyl)sulphonyl]-2-oxo-2,3-dihydro- 1H-indol-3-yl}-4-(1-methylpiperidin-4-yl)piperazine-1-carboxamide;

N-[5-cyano-1-[(2-ethoxy-4-methoxyphenyl)sulphonyl]-3-(2-ethoxypyridin-3-yl)-2-oxo- 2,3-dihydro-1H-indol-3-yl]-4-(1-methylpiperidin-4-yl)piperazine-1-carboxamide;

N-[5-cyano-1-[(2,4-dimethoxyphenyl)sulphonyl]-3-(2-ethoxypyridin-3-yl)-2-oxo-2,3-dihydro-1H-indol-3-yl]-4-(1-ethylpiperidin-4-yl)piperazine-1-carboxamide;

N-{5-cyano-3-(2-ethoxypyridin-3-yl)-1-[(2-methoxyphenyl)sulphonyl]-2-oxo-2,3-dihydro- 1H-indol-3-yl}-4-(1-ethylpiperidin-4-yl)piperazine-1-carboxamide;

N-[5-cyano-1-[(2-ethoxyphenyl)sulphonyl]-3-(2-ethoxypyridin-3-yl)-2-oxo-2,3-dihydro- 1H-indol-3-yl]-4-(1-ethylpiperidin-4-yl)piperazine-1-carboxamide;

N-[5-cyano-3-(2-ethoxypyridin-3-yl)-2-oxo-1-(phenylsulphonyl)-2,3-dihydro-1H-indol-3-yl]-4-(1-ethylpiperidin-4-yl)piperazine-1-carboxamide;

N-{5-cyano-3-(2-ethoxypyridin-3-yl)-1-[(4-methoxyphenyl)sulphonyl]-2-oxo-2,3-dihydro- 1H-indol-3-yl}-4-(1-ethylpiperidin-4-yl)piperazine-1-carboxamide;

N-[5-cyano-1-[(2-ethoxy-4-methoxyphenyl)sulphonyl]-3-(2-ethoxypyridin-3-yl)-2-oxo- 2,3-dihydro-1H-indol-3-yl]-4-(1-ethylpiperidin-4-yl)piperazine-1-carboxamide;

N-[5-cyano-1-[(2,4-dimethoxyphenyl)sulphonyl]-3-(2-ethoxypyridin-3-yl)-2-oxo-2,3-dihydro-1H-indol-3-yl]-4-(1-propylpiperidin-4-yl)piperazine-1-carboxamide;

N-{5-cyano-3-(2-ethoxypyridin-3-yl)-1-[(2-methoxyphenyl)sulphonyl]-2-oxo-2,3-dihydro- 1H-indol-3-yl}-4-(1-propylpiperidin-4-yl)piperazine-1-carboxamide;

N-[5-cyano-1-[(2-ethoxyphenyl)sulphonyl]-3-(2-ethoxypyridin-3-yl)-2-oxo-2,3-dihydro- 1H-indol-3-yl]-4-(1-propylpiperidin-4-yl)piperazine-1-carboxamide;

N-[5-cyano-3-(2-ethoxypyridin-3-yl)-2-oxo-1-(phenylsulphonyl)-2,3-dihydro-1H-indol-3-yl]-4-(1-propylpiperidin-4-yl)piperazine-1-carboxamide;

N-{5-cyano-3-(2-ethoxypyridin-3-yl)-1[(4-methoxyphenyl)sulphonyl]-2-oxo-2,3-dihydro- 1H-indol-3-yl}-4-(1-propylpiperidin-4-yl)piperazine-1-carboxamide;

N-[5-cyano-1-[(2-ethoxy-4-methoxyphenyl)sulphonyl]-3-(2-ethoxypyridin-3-yl)-2-oxo- 2,3-dihydro-1H-indol-3-yl]-4-(1-propylpiperidin-4-yl)piperazine-1-carboxamide;

N-[5-cyano-1-[(2,4-dimethoxyphenyl)sulphonyl]-3-(2-ethoxypyridin-3-yl)-2-oxo-2,3-dihydro-1H-indol-3-yl]-4-(1-isopropylpiperidin-4-yl)piperazine-1-carboxamide;

N-{5-cyano-3-(2-ethoxypyridin-3-yl)-1-[(2-methoxyphenyl)sulphonyl]-2-oxo-2,3-dihydro- 1H-indol-3-yl}-4-(1-isopropylpiperidin-4-yl)piperazine-1-carboxamide;

N-[5-cyano-1-[(2-ethoxyphenyl)sulphonyl]-3-(2-ethoxypyridin-3-yl)-2-oxo-2,3-dihydro- 1H-indol-3-yl]-4-(1-isopropylpiperidin-4-yl)piperazine-1-carboxamide;

N-[5-cyano-3-(2-ethoxypyridin-3-yl)-2-oxo-1-(phenylsulphonyl)-2,3-dihydro-1H-indol-3-yl]-4-(1-isopropylpiperidin-4-yl)piperazine-1-carboxamide;

N-{5-cyano-3-(2-ethoxypyridin-3-yl)-1-[(4-methoxyphenyl)sulphonyl]-2-oxo-2,3-dihydro- 1H-indol-3-yl}-4-(1-isopropylpiperidin-4-yl)piperazine-1-carboxamide;

N-[5-cyano-1-[(2-ethoxy-4-methoxyphenyl)sulphonyl]-3-(2-ethoxypyridin-3-yl)-2-oxo- 2,3-dihydro-1H-indol-3-yl]-4-(1-isopropylpiperidin-4-yl)piperazine-1-carboxamide;

N-[5-cyano-1-[(2,4-dimethoxyphenyl)sulphonyl]-3-(2-ethoxypyridin-3-yl)-2-oxo-2,3-dihydro-1H-indol-3-yl]-4-piperidin-4-ylpiperazine-1-carboxamide;

N-{5-cyano-3-(2-ethoxypyridin-3-yl)-1-[(2-methoxyphenyl)sulphonyl]-2-oxo-2,3-dihydro- 1H-indol-3-yl}-4-piperidin-4-ylpiperazine-1-carboxamide;

N-[5-cyano-1-[(2-ethoxyphenyl)sulphonyl]-3-(2-ethoxypyridin-3-yl)-2-oxo-2,3-dihydro-1H-indol-3-yl]-4-piperidin-4-ylpiperazine-1-carboxamide;

N-[5-cyano-3-(2-ethoxypyridin-3-yl)-2-oxo-1-(phenylsulphonyl)-2,3-dihydro-1H-indol-3-yl]-4-piperidin-4-ylpiperazine-1-carboxamide;

N-{5-cyano-3-(2-ethoxypyridin-3-yl)-1-[(4-methoxyphenyl)sulphonyl]-2-oxo-2,3-dihydro- 1H-indol-3-yl}-4-piperidin-4-ylpiperazine-1-carboxamide;

N-[5-cyano-1-[(2-ethoxy-4-methoxyphenyl)sulphonyl]-3-(2-ethoxypyridin-3-yl)-2-oxo- 2,3-dihydro-1H-indol-3-yl]-4-piperidin-4-ylpiperazine-1-carboxamide;

N-[5-cyano-1-[(2,4-dimethoxyphenyl)sulphonyl]-3-(2-ethoxypyridin-3-yl)-2-oxo-2,3-dihydro- 1H-indol-3-yl]-4-(4-methylpiperazin-1-yl)piperidine-1-carboxamide;

N-{5-cyano-3-(2-ethoxypyridin-3-yl)-1-[(2-methoxyphenyl)sulphonyl]-2-oxo-2,3-dihydro- 1H-indol-3-yl}-4-(4-methylpiperazin-1-yl)piperidine-1-carboxamide;

N-[5-cyano-1-[(2-ethoxyphenyl)sulphonyl]-3-(2-ethoxypyridin-3-yl)-2-oxo-2,3-dihydro- 1 H-indol-3-yl]-4-(4-methylpiperazin-1-yl)piperidine-1-carboxamide;

N-[5-cyano-3-(2-ethoxypyridin-3-yl)-2-oxo-1-(phenylsulphonyl)-2,3-dihydro-1H-indol-3-yl]-4-(4-methylpiperazin-1-yl)piperidine-1-carboxamide;

N-{5-cyano-3-(2-ethoxypyridin-3-yl)-1-[(4-methoxyphenyl)sulphonyl]-2-oxo-2,3-dihydro- 1H-indol-3-yl}-4-(4-methylpiperazin-1-yl)piperidine-1-carboxamide;

N-[5-cyano-1-[(2-ethoxy-4-methoxyphenyl)sulphonyl]-3-(2-ethoxypyridin-3-yl)-2-oxo- 2,3-dihydro-1H-indol-3-yl]-4-(4-methylpiperazin-1-yl)piperidine-1-carboxamide;

N-[5-cyano-1-[(2,4-dimethoxyphenyl)sulphonyl]-3-(2-ethoxypyridin-3-yl)-2-oxo-2,3-dihydro-1H-indol-3-yl]-4-(4-ethylpiperazin-1-yl)piperidine-1-carboxamide;

N-{5-cyano-3-(2-ethoxypyridin-3-yl)-1-[(2-methoxyphenyl)sulphonyl]-2-oxo-2,3-dihydro- 1H-indol-3-yl}-4-(4-ethylpiperazin-1-yl)piperidine-1-carboxamide;

N-[5-cyano-1-[(2-ethoxyphenyl)sulphonyl]-3-(2-ethoxypyridin-3-yl)-2-oxo-2,3-dihydro- 1H-indol-3-yl]-4-(4-ethylpiperazin-1-yl)piperidine-1-carboxamide;

N-[5-cyano-3-(2-ethoxypyridin-3-yl)-2-oxo-1-(phenylsulphonyl)-2,3-dihydro-1H-indol-3-yl]-4-(4-ethylpiperazin-1-yl)piperidine-1-carboxamide;

N-{5-cyano-3-(2-ethoxypyridin-3-yl)-1-[(4-methoxyphenyl)sulphonyl]-2-oxo-2,3-dihydro- 1H-indol-3-yl}-4-(4-ethylpiperazin-1-yl)piperidine-1-carboxamide;

N-[5-cyano-1-[(2-ethoxy-4-methoxyphenyl)sulphonyl]-3-(2-ethoxypyridin-3-yl)-2-oxo- 2,3-dihydro-1H-indol-3-yl]-4-(4-ethylpiperazin-1-yl)piperidine-1-carboxamide;

N-[5-cyano-1-[(2,4-dimethoxyphenyl)sulphonyl]-3-(2-ethoxypyridin-3-yl)-2-oxo-2,3-dihydro-1H-indol-3-yl]-4-(4-propylpiperazin-1-yl)piperidine-1-carboxamide;

N-{5-cyano-3-(2-ethoxypyridin-3-yl)-1-[(2-methoxyphenyl)sulphonyl]-2-oxo-2,3-dihydro- 1H-indol-3-yl}-4-(4-propylpiperazin-1-yl)piperidine-1-carboxamide;

N-[5-cyano-1-[(2-ethoxyphenyl)sulphonyl]-3-(2-ethoxypyridin-3-yl)-2-oxo-2,3-dihydro- 1H-indol-3-yl]-4-(4-propylpiperazin-1-yl)piperidine-1-carboxamide;

N-[5-cyano-3-(2-ethoxypyridin-3-yl)-2-oxo-1-phenylsu1phonyl)-2,3-dihydro-1H-indol-3-yl]-4-(4-propylpiperazin-1-yl)piperidine-1-carboxamide;

N-{5-cyano-3-(2-ethoxypyridin-3-yl)-1-[(4-methoxyphenyl)sulphonyl]-2-oxo-2,3-dihydro- 1H-indol-3-yl}-4-(4-propylpiperazin-1-yl)piperidine-1-carboxamide;

N-[5-cyano-1-[(2-ethoxy-4-methoxyphenyl)sulphonyl]-3-(2-ethoxypyridin-3-yl)-2-oxo- 2,3-dihydro-1H-indol-3-yl]-4-(4-propylpiperazin-1-yl)piperidine-1-carboxamide;

N-[5-cyano-1-[(2,4-dimethoxyphenyl)sulphonyl]-3-(2-ethoxypyridin-3-yl)-2-oxo-2,3-dihydro-1H-indol-3-yl]-4-(4-isopropylpiperazin-1-yl)piperidine-1-carboxamide;

N-{5-cyano-3-(2-ethoxypyridin-3-yl)-1-[(2-methoxyphenyl)sulphonyl]-2-oxo-2,3-dihydro-1H-indol-3-yl}-4-(4-isopropylpiperazin-1-yl)piperidine-1-carboxamide;

N-[5-cyano-1-[(2-ethoxyphenyl)sulphonyl]-3-(2-ethoxypyridin-3-yl)-2-oxo-2,3-dihydro-1H-indol-3-yl]-4-(4-isopropylpiperazin-1-yl)piperidine-1-carboxamide;

N-[5-cyano-3-(2-ethoxypyridin-3-yl)-2-oxo-1-(phenylsulphonyl)-2,3-dihydro-1H-indol-3-yl]-4-(4-isopropylpiperazin-1-yl)piperidine-1-carboxamide;

N-{5-cyano-3-(2-ethoxypyridin-3-yl)-1-[(4-methoxyphenyl)sulphonyl]-2-oxo-2,3-dihydro-1H-indol-3-yl}-4-(4-isopropylpiperazin-1-yl)piperidine-1-carboxamide;

N-[5-cyano-1-[(2-ethoxy-4-methoxyphenyl)sulphonyl]-3-(2-ethoxypyridin-3-yl)-2-oxo-2,3-dihydro-1H-indol-3-yl]-4-(4-isopropylpiperazin-1-yl)piperidine-1-carboxamide;

N-[5-cyano-1-[(2,4-dimethoxyphenyl)sulphonyl]-3-(2-ethoxypyridin-3-yl)-2-oxo-2,3-dihydro-1H-indol-3-yl]-4-piperazin-1-ylpiperidine-1-carboxamide;

N-{5-cyano-3-(2-ethoxypyridin-3-yl)-1-[(2-methoxyphenyl)sulphonyl]-2-oxo-2,3-dihydro-1H-indol-3-yl}-4-piperazin-1-ylpiperidine-1-carboxamide;

N-[5-cyano-1-[(2-ethoxyphenyl)sulphonyl]-3-(2-ethoxypyridin-3-yl)-2-oxo-2,3-dihydro-1H-indol-3-yl]-4-piperazin-1-ylpiperidine-1-carboxamide;

N-[5-cyano-3-(2-ethoxypyridin-3-yl)-2-oxo-1-(phenylsulphonyl)-2,3-dihydro-1H-indol-3-yl]-4-piperazin-1-ylpiperidine-1-carboxamide;

N-{5-cyano-3-(2-ethoxypyridin-3-yl)-1-[(4-methoxyphenyl)sulphonyl]-2-oxo-2,3-dihydro-1H-indol-3-yl}-4-piperazin-1-ylpiperidine-1-carboxamide;

N-[5-cyano-1-[(2-ethoxy-4-methoxyphenyl)sulphonyl]-3-(2-ethoxypyridin-3-yl)-2-oxo-2,3-dihydro-1H-indol-3-yl]-4-piperazin-1-ylpiperidine-1-carboxamide;

N-[5-cyano-1-[(2,4-dimethoxyphenyl)sulphonyl]-3-(2-ethoxypyridin-3-yl)-2-oxo-2,3-dihydro-1H-indol-3-yl]-1'-methyl-4,4'-bipiperidine-1-carboxamide;

N-{5-cyano-3-(2-ethoxypyridin-3-yl)-1-[(2-methoxyphenyl)sulphonyl]-2-oxo-2,3-dihydro-1H-indol-3-yl}-1'-methyl-4,4'-bipipericline-1-carboxamide;

N-[5-cyano-1-[(2-ethoxyphenyl)sulphonyl]-3-(2-ethoxypyridin-3-yl)-2-oxo-2,3-dihydro-1H-indol-3-yl]-1'-methyl-4,4'-bipiperidine-1-carboxamide;

N-[5-cyano-3-(2-ethoxypyridin-3-yl)-2-oxo-1-phenylsulphonyl)-2,3-dihydro-1H-indol-3-yl]-1'-methyl-4,4'-bipiperidine-1-carboxamide;

N-{5-cyano-3-(2-ethoxypyridin-3-yl)-1-[(4-methoxyphenyl)sulphonyl]-2-oxo-2,3-dihydro-1H-indol-3-yl}-1'-methyl-4,4'-bipipericline-1-carboxamide;

N-[5-cyano-1-[(2-ethoxy-4-methoxyphenyl)sulphonyl]-3-(2-ethoxypyridin-3-yl)-2-oxo-2,3-dihydro-1H-indol-3-yl]-1'-methyl-4,4'-bipiperidine-1-carboxamide;

N-[5-cyano-1-[(2,4-dimethoxyphenyl)sulphonyl]-3-(2-ethoxypyridin-3-yl)-2-oxo-2,3-dihydro-1H-indol-3-yl]-1'-ethyl-4,4'-bipiperidine-1-carboxamide;

N-{5-cyano-3-(2-ethoxypyridin-3-yl)-1-[(2-methoxyphenyl)sulphonyl]-2-oxo-2,3-dihydro-1H-indol-3-yl}-1'-ethyl-4,4'-bipiperidine-1-carboxamide;

N-[5-cyano-1-[(2-ethoxyphenyl)sulphonyl]-3-(2-ethoxypyridin-3-yl)-2-oxo-2,3-dihydro-1H-indol-3-yl]-1'-ethyl-4,4'-bipiperidine-1-carboxamide;

N-[5-cyano-3-(2-ethoxypyridin-3-yl)-2-oxo-1-(phenylsulphonyl)-2,3-dihydro-1H-indol-3-yl]-1'-ethyl-4,4'-bipiperidine-1-carboxamide;

N-{5-cyano-3-(2-ethoxypyridin-3-yl)-1-[(4-methoxyphenyl)sulphonyl]-2-oxo-2,3-dihydro-1H-indol-3-yl}-1'-ethyl-4,4'-bipiperidine-1-carboxamide;

N-[5-cyano-1-[(2-ethoxy-4-methoxyphenyl)sulphonyl]-3-(2-ethoxypyridin-3-yl)-2-oxo-2,3-dihydro-1H-indol-3-yl]-1'-ethyl-4,4'-bipiperidine-1-carboxamide;

N-[5-cyano-1-[(2,4-dimethoxyphenyl)sulphonyl]-3-(2-ethoxypyridin-3-yl)-2-oxo-2,3-dihydro-1H-indol-3-yl]-1'-propyl-4,4'-bipiperidine-1-carboxamide;

N-{5-cyano-3-(2-ethoxypyridin-3-yl)-1-[(2-methoxyphenyl)sulphonyl]-2-oxo-2,3-dihydro-1H-indol-3-yl}-1'-propyl-4,4'-bipiperidine-1-carboxamide;

N-[5-cyano-1-[(2-ethoxyphenyl)sulphonyl]-3-(2-ethoxypyridin-3-yl)-2-oxo-2,3-dihydro-1H-indol-3-yl]-1'-propyl-4,4'-bipiperidine-1-carboxamide;

N-[5-cyano-3-(2-ethoxypyridin-3-yl)-2-oxo-1-(phenylsulphonyl)-2,3-dihydro-1H-indol-3-yl]-1'-propyl-4,4'-bipiperidine-1-carboxamide;

N-{5-cyano-3-(2-ethoxypyridin-3-yl)-1-[(4-methoxyphenyl)sulphonyl]-2-oxo-2,3-dihydro-1H-indol-3-yl}-1'-propyl-4,4'-bipiperidine-1-carboxamide;

N-[5-cyano-1-[(2-ethoxy-4-methoxyphenyl)sulphonyl]-3-(2-ethoxypyridin-3-yl)-2-oxo-2,3-dihydro-1H-indol-3-yl]-1'-propyl-4,4'-bipiperidine-1-carboxamide;

N-[5-cyano-1-[(2,4-dimethoxyphenyl)sulphonyl]-3-(2-ethoxypyridin-3-yl)-2-oxo-2,3-dihydro-1H-indol-3-yl]-1'-isopropyl-4,4'-bipiperidine-1-carboxamide;

N-{5-cyano-3-(2-ethoxypyridin-3-yl)-1-[(2-methoxyphenyl)sulphonyl]-2-oxo-2,3-dihydro-1H-indol-3-yl}-1'-isopropyl-4,4'-bipiperidine-1-carboxamide;

N-[5-cyano-1-[(2-ethoxyphenyl)sulphonyl]-3-(2-ethoxypyridin-3-yl)-2-oxo-2,3-dihydro-1H-indol-3-yl]-1'-isopropyl-4,4'-bipiperidine-1-carboxamide;

N-[5-cyano-3-(2-ethoxypyridin-3-yl)-2-oxo-1-phenylsulphonyl)-2,3-dihydro-1H-indol-3-yl]-1'-isopropyl-4,4'-bipiperidine-1-carboxamide;

N-{5-cyano-3-(2-ethoxypyridin-3-yl)-1-[(4-methoxyphenyl)sulphonyl]-2-oxo-2,3-dihydro-1H-indol-3-yl}-1'-isopropyl-4,4'-bipiperidine-1-carboxamide;

N-[5-cyano-1-[(2-ethoxy-4-methoxyphenyl)sulphonyl]-3-(2-ethoxypyridin-3-yl)-2-oxo-2,3-dihydro-1H-indol-3-yl]-1'-isopropyl-4,4'-bipiperidine-1-carboxamide;

N-[5-cyano-1-[(2,4-dimethoxyphenyl)sulphonyl]-3-(2-ethoxypyridin-3-yl)-2-oxo-2,3-dihydro-1H-indol-3-yl]-4,4'-bipiperidine-1-carboxamide;

N-{5-cyano-3-(2-ethoxypyridin-3-yl)-1-[(2-methoxyphenyl)sulphonyl]-2-oxo-2,3-dihydro-1H-indol-3-yl}-4,4'-bipiperidine-1-carboxamide;

N-[5-cyano-1-[(2-ethoxyphenyl)sulphonyl]-3-(2-ethoxypyridin-3-yl)-2-oxo-2,3-dihydro-1H-indol-3-yl]-4,4'-bipiperidine-1-carboxamide;

N-[5-cyano-3-(2-ethoxypyridin-3-yl)-2-oxo-1-phenylsulphonyl)-2,3-dihydro-1H-indol-3-yl]-4,4'-bipiperidine-1-carboxamide;

N-{5-cyano-3-(2-ethoxypyridin-3-yl)-1-[(4-methoxyphenyl)sulphonyl]-2-oxo-2,3-dihydro-1H-indol-3-yl}-4,4'-bipiperidine-1-carboxamide; and N-[5-cyano-1-[(2-ethoxy-4-methoxyphenyl)sulphonyl]-3-(2-ethoxypyridin-3-yl)-2-oxo-2,3-dihydro-1H-indol-3-yl]-4,4'-bipiperidine-1-carboxamide; or a pharmaceutically acceptable salt thereof or a tautomeric form thereof.

20. The compound according to claim 19, present in optically active form as the (laevorotatory) (−)-enantiomer, which rotates the plane of polarization of linear polarized light to the left, a pharmaceutically acceptable salt thereof or a tautomeric form thereof.

21. The compound according to claim 19, in optically active form, characterized in that the corresponding laevorotatory (−)-enantiomer is present in an optical purity (enantiomeric excess, ee) of greater than 50%, a pharmaceutically acceptable salt thereof or a tautomeric form thereof.

22. The compound according to claim 19, in optically active form, characterized in that the corresponding laevorotatory (−)-enantiomer is present in an optical purity (enantiomeric excess, ee) of greater than 90%, a pharmaceutically acceptable salt thereof or a tautomeric form thereof.

23. The compound according to claim 19, in the form of the racemate, a pharmaceutically acceptable salt thereof, or a tautomeric form thereof.

24. A pharmaceutical composition comprising at least one compound of the general formula (I) according to claim 1, or at least one pharmaceutically acceptable salt, or one tautomeric form thereof and a pharmaceutical carrier.

25. A pharmaceutical composition comprising at least one compound according to claim 19, or at least one pharmaceutically acceptable salt, or one tautomeric form thereof and a pharmaceutical carrier.

26. N-[5-cyano-1-[(2,4-dimethoxyphenyl)sulphonyl]-3-(2-ethoxypyridin-3-yl)-2- oxo-2,3-dihydro-1H-indol-3-yl]-4-(1-methylpiperidin-4-yl)piperazine-1-carboxamide, a pharmaceutically acceptable salt thereof or a tautomeric form thereof.

27. The compound according to claim 26, present in optically active form as the (laevorotatory) (−)-enantiomer, which rotates the plane of polarization of linear polarized light to the left, a pharmaceutically acceptable salt thereof or a tautomeric form thereof.

28. The compound according to claim 26, in optically active form, characterized in that the corresponding laevorotatory (−)-enantiomer is present in an optical purity (enantiomeric excess, ee) of greater than 50%, a pharmaceutically acceptable salt thereof or a tautomeric form thereof.

29. The compound according to claim 26, in optically active form, characterized in that the corresponding laevorotatory (−)-enantiomer is present in an optical purity (enantiomeric excess, ee) of greater than 90%, a pharmaceutically acceptable salt thereof or a tautomeric form thereof.

30. The compound according to claim 26, in the form of the racemate, a pharmaceutically acceptable salt thereof, or a tautomeric form thereof.

31. N-[5-cyano-1-[(2,4-dimethoxyphenyl)sulphonyl]-3-(2-ethoxypyridin-3-yl)-2- oxo-2,3-dihydro-1H-indol-3-yl]-4-(4-methylpiperazin-1-yl)piperidine-1-carboxamide, a pharmaceutically acceptable salt thereof or a tautomeric form thereof.

32. The compound according to claim 31, present in optically active form as the (laevorotatory) (−)-enantiomer, which rotates the plane of polarization of linear polarized light to the left, a pharmaceutically acceptable salt thereof or a tautomeric form thereof.

33. The compound according to claim 31, in optically active form, characterized in that the corresponding laevorotatory (-)-enantiomer is present in an optical purity (enantiomeric excess, ee) of greater than SO%, a pharmaceutically acceptable salt thereof or a tautomeric form thereof.

34. The compound according to claim 31, in optically active form, characterized in that the corresponding laevorotatory (-)-enantiomer is present in an optical purity (enantiomeric excess, ee) of greater than 9O%, a pharmaceutically acceptable salt thereof or a tautomeric form thereof.

35. The compound according to claim 31, in the form of the racemate, a pharmaceutically acceptable salt thereof, or a tautomeric form thereof.

36. N-[5-cyano-1-[(2,4-dimethoxyphenyl)sulphonyl]-3-(2-ethoxypyridin-3-yl)-2- oxo-2,3-dihydro-1H-indol-3-yl]-4-(4-ethylpiperazin-1-yl)piperidine-1-carboxamide, a pharmaceutically acceptable salt thereof or a tautomeric form thereof.

37. The compound according to claim 36, present in optically active form as the (laevorotatory) (−)-enantiomer, which rotates the plane of polarization of linear polarized light to the left, a pharmaceutically acceptable salt thereof or a tautomeric form thereof.

38. The compound according to claim 36, in optically active form, characterized in that the corresponding laevorotatory (−)-enantiomer is present in an optical purity (enantiomeric excess, ee) of greater than 50%, a pharmaceutically acceptable salt thereof or a tautomeric form thereof.

39. The compound according to claim 36, in optically active form, characterized in that the corresponding laevorotatory (−)-enantiomer is present in an optical purity (enantiomeric excess, ee) of greater than 90%, a pharmaceutically acceptable salt thereof or a tautomeric form thereof.

40. The compound according to claim 36, in the form of the racemate, a pharmaceutically acceptable salt thereof, or a tautomeric form thereof.

41. A pharmaceutical composition comprising N-[5-cyano-1-[(2,4- dimethoxyphenyl)sulphonyl]-3-(2-ethoxypyridin-3-yl)-2-oxo-2,3-dihydro-1H-indol-3-yl]-4-(1- methylpiperidin-4-yl)piperazine-1-carboxamide, a pharmaceutically acceptable salt or a tautomeric form thereof and a pharmaceutical carrier.

42. The pharmaceutical composition according to claim 41, wherein N-[5-cyano- 1-[(2,4-dimethoxyphenyl)sulphonyl]-3-(2-ethoxypyridin-3-yl)-2-oxo-2,3-dihydro-1H-indol-3-yl]- 4-(1-methylpiperidin-4-yl)piperazine-1-carboxamide is present in optically active form as the (laevorotatory) (−)-enantiomer, which rotates the plane of polarization of linear polarized light to the left, a pharmaceutically acceptable salt thereof or a tautomeric form thereof.

43. The pharmaceutical composition according to claim 41, wherein N-[5-cyano- 1-[(2,4-dimethoxyphenyl)sulphonyl]-3-(2-ethoxypyridin-3-yl)-2-oxo-2,3-dihydro-1H-indol-3-yl]- 4-(1-methylpiperidin-4-yl)piperazine-1-carboxamide is present in an optical purity (enantiomeric excess, ee) of greater than 50%, a pharmaceutically acceptable salt thereof or a tautomeric form thereof.

44. The pharmaceutical composition according to claim 41, wherein N-[5-cyano- 1-[(2,4-dimethoxyphenyl)sulphonyl]-3-(2-ethoxypyridin-3-yl)-2-oxo-2,3-dihydro-1H-indol-3-yl]- 4-(1-methylpiperidin-4-yl)piperazine-1-carboxamide is present in an optical purity (enantiomeric excess, ee) of greater than 90%, a pharmaceutically acceptable salt thereof or a tautomeric form thereof.

45. The pharmaceutical composition according to claim 41, wherein N-[5-cyano- 1-[(2,4-dimethoxyphenyl)sulphonyl]-3-(2-ethoxypyridin-3-yl)-2-oxo-2,3-dihydro-1H-indol-3-yl]- 4-(1-methylpiperidin-4-yl)piperazine-1-carboxamide is present in the form of the racemate, a pharmaceutically acceptable salt thereof, or a tautomeric form thereof.

46. A pharmaceutical composition comprising N-[5-cyano-1-[(2,4- dimethoxyphenyl)sulphonyl]-3-(2-ethoxypyridin-3-yl)-2-oxo-2,3-dihydro-1H-indol-3-yl]-4-(4- methylpiperazin-1-yl)piperidine-1-carboxamide, a pharmaceutically acceptable salt or a tautomeric form thereof and a pharmaceutical carrier.

47. The pharmaceutical composition according to claim 46, wherein N-[5-cyano- 1-[(2,4-dimethoxyphenyl)sulphonyl]-3-(2-ethoxypyridin-3-yl)-2-oxo-2,3-dihydro-1H-indol-3-yl]- 4-(4-methylpiperazin-1-yl)piperidine-1-carboxamide is present in optically active form as the (laevorotatory) (−)-enantiomer, which rotates the plane of polarization of linear polarized light to the left, a pharmaceutically acceptable salt thereof or a tautomeric form thereof.

48. The pharmaceutical composition according to claim 46, wherein N-[5-cyano- 1-[(2,4-dimethoxyphenyl)sulphonyl]-3-(2-ethoxypyridin-3-yl)-2-oxo-2,3-dihydro-1H-indol-3-yl]- 4-(4-methylpiperazin-1-yl)piperidine-1-carboxamide is present in an optical purity (enantiomeric excess, ee) of greater than 50%, a pharmaceutically acceptable salt thereof or a tautomeric form thereof.

49. The pharmaceutical composition according to claim 46, wherein N-[5-cyano- 1-[(2,4-dimethoxyphenyl)sulphonyl]-3-(2-ethoxypyridin-3-yl)-2-oxo-2,3-dihydro-1H-indol-3-yl]- 4-(4-methylpiperazin-1-yl)piperidine-1-carboxamide is present in an optical purity (enantiomeric excess, ee) of greater than 90%, a pharmaceutically acceptable salt thereof or a tautomeric form thereof.

50. The pharmaceutical composition according to claim 46, wherein N-[5-cyano- 1-[(2,4-dimethoxyphenyl)sulphonyl]-3-(2-ethoxypyridin-3-yl)-2-oxo-2,3-dihydro-1H-indol-3-yl]- 4-(4-methylpiperazin-1-yl)piperidine-1-carboxamide is present in the form of the racemate, a pharmaceutically acceptable salt thereof, or a tautomeric form thereof.

51. A pharmaceutical composition comprising N-[5-cyano-1-[(2,4- dimethoxyphenyl)sulphonyl]-3-(2-ethoxypyridin-3-yl)-2-oxo-2,3-dihydro-1H-indol-3-yl]-4-(4- ethylpiperazin-1-yl) piperidine-1-carboxamide, a pharmaceutically acceptable salt or a tautomeric form thereof and a pharmaceutical carrier.

52. The pharmaceutical composition according to claim 51, wherein N-[5-cyano- 1-[(2,4-dimethoxyphenyl)sulphonyl]-3-(2-ethoxypyridin-3-yl)-2-oxo-2,3-dihydro-1H-indol-3-yl]- 4-(4-ethylpiperazin-1-yl)piperidine-1-carboxamide is present in optically active form as the (laevorotatory) (−)-enantiomer, which rotates the plane of polarization of linear polarized light to the left, a pharmaceutically acceptable salt thereof or a tautomeric form thereof.

53. The pharmaceutical composition according to claim 51, wherein N-[5-cyano- 1-[(2,4-dimethoxyphenyl)sulphonyl]-3-(2-ethoxypyridin-3-yl)-2-oxo-2,3-dihydro-1H-indol-3-yl]- 4-(4-ethylpiperazin-1-yl)piperidine-1-carboxamide is present in an optical purity (enantiomeric excess, ee) of greater than 50%, a pharmaceutically acceptable salt thereof or a tautomeric form thereof.

54. The pharmaceutical composition according to claim 51, wherein N-[5-cyano- 1-[(2,4-dimethoxyphenyl)sulphonyl]-3-(2-ethoxypyridin-3-yl)-2-oxo-2,3-dihydro-1H-indol-3-yl]- 4-(4-ethylpiperazin-1-yl)piperidine-1-carboxamide is present in an optical purity (enantiomeric excess, ee) of greater than 90%, a pharmaceutically acceptable salt thereof or a tautomeric form thereof.

55. The pharmaceutical composition according to claim 51, wherein N-[5-cyano- 1-[(2,4-dimethoxyphenyl)sulphonyl]-3-(2-ethoxypyridin-3-yl)-2-oxo-2,3-dihydro-1H-indol-3-yl]- 4-(4-ethylpiperazin-1-yl)piperidine-1-carboxamide is present in the form of the racemate, a pharmaceutically acceptable salt thereof, or a tautomeric form thereof.

* * * * *